(12) United States Patent
Tanzer et al.

(10) Patent No.: US 11,192,899 B2
(45) Date of Patent: Dec. 7, 2021

(54) QUINOXALINE DERIVATIVES AS ADENOSINE RECEPTOR ANTAGONISTS

(71) Applicant: MERCK PATENT GMBH, Darmstadt (DE)

(72) Inventors: Eva-Maria Tanzer, Darmstadt (DE); Kai Schiemann, Seeheim-Jugenheim (DE); Markus Klein, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 21 days.

(21) Appl. No.: 16/640,526

(22) PCT Filed: Aug. 20, 2018

(86) PCT No.: PCT/EP2018/072397
§ 371 (c)(1),
(2) Date: Feb. 20, 2020

(87) PCT Pub. No.: WO2019/038214
PCT Pub. Date: Feb. 28, 2019

(65) Prior Publication Data
US 2020/0354375 A1    Nov. 12, 2020

(30) Foreign Application Priority Data
Aug. 21, 2017 (EP) .................................. 17187100

(51) Int. Cl.
| | | |
|---|---|---|
| C07D 495/10 | (2006.01) | |
| C07D 241/44 | (2006.01) | |
| C07D 401/12 | (2006.01) | |
| C07D 403/04 | (2006.01) | |
| C07D 413/14 | (2006.01) | |
| C07D 405/14 | (2006.01) | |
| C07D 405/04 | (2006.01) | |
| C07D 471/04 | (2006.01) | |
| C07D 491/107 | (2006.01) | |
| C07D 417/12 | (2006.01) | |
| C07D 403/12 | (2006.01) | |
| A61K 45/06 | (2006.01) | |

(52) U.S. Cl.
CPC ......... *C07D 495/10* (2013.01); *C07D 241/44* (2013.01); *C07D 401/12* (2013.01); *C07D 403/04* (2013.01); *C07D 403/12* (2013.01); *C07D 405/04* (2013.01); *C07D 405/14* (2013.01); *C07D 413/14* (2013.01); *C07D 417/12* (2013.01); *C07D 471/04* (2013.01); *C07D 491/107* (2013.01); *A61K 45/06* (2013.01)

(58) Field of Classification Search
CPC .. C07D 495/10; C07D 241/44; C07D 401/12; C07D 403/04; C07D 403/12; C07D 405/04; C07D 405/14; C07D 413/14; C07D 417/12; C07D 471/04; C07D 491/107; A61K 45/06
USPC ...................................................... 514/210.16
See application file for complete search history.

(56) References Cited

U.S. PATENT DOCUMENTS

| | | |
|---|---|---|
| 7,368,446 B2 | 5/2008 | Flohr et al. |
| 7,371,748 B2 | 5/2008 | Flohr et al. |
| 8,415,353 B2 | 4/2013 | Harris et al. |

FOREIGN PATENT DOCUMENTS

| | | |
|---|---|---|
| WO | 05000842 A1 | 1/2005 |
| WO | 05116026 A1 | 12/2005 |
| WO | 09111442 A1 | 9/2009 |

OTHER PUBLICATIONS

Leone R et al.—Computational and Structural Biotechnology Journal; 2015; 13; 265-273.
Office Action dated Feb. 23, 2021 in corresponding EP appln. 18753208.0 (pp. 1-2).
International search report PCT/EP2018/072397 dated Sep. 27, 2018 (pp. 1-3).

*Primary Examiner* — Kristin A Vajda
(74) *Attorney, Agent, or Firm* — Millen White Zelano and Branigan, PC; Csaba Henter

(57) ABSTRACT

The invention relates to quinoxaline derivatives of the general formula I, and the use of the compounds of the present invention for the treatment and/or prevention of hyperproliferative or infectious diseases and disorders in mammals, especially humans, and pharmaceutical compositions containing such compound.

21 Claims, No Drawings

QUINOXALINE DERIVATIVES AS ADENOSINE RECEPTOR ANTAGONISTS

The invention relates to quinoxaline derivatives of the general formula I,

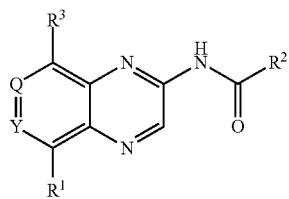

and the use of the compounds of the present invention for the treatment and/or prevention of hyperproliferative or infectious diseases and disorders in mammals, especially humans, and pharmaceutical compositions containing such compounds.

BACKGROUND OF THE INVENTION

Adenosine is an ubiquitous modulator of numerous physiological activities, particularly within the cardiovascular, nervous and immune systems. Adenosine is related both structurally and metabolically to the bioactive nucleotides adenosine triphosphate (ATP), adenosine diphosphate (ADP), adenosine monophosphate (AMP) and cyclic adenosine monophosphate (cAMP), to the biochemical methylating agent S-adenosyl-L-methione (SAM) and structurally to the coenzymes NAD, FAD and coenzyme A and to RNA.

Via cell surface receptors, adenosine modulates diverse physiological functions including induction of sedation, vasodilatation, suppression of cardiac rate and contractility, inhibition of platelet aggregability, stimulation of gluconeogenesis and inhibition of lipolysis. Studies show that adenosine is able to activate adenylate cyclases, open potassium channels, reduce flux through calcium channels, and inhibit or stimulate phosphoinositide turnover through receptor-mediated mechanisms (Muller C. E. and Stein B., Current Pharmaceutical Design, 2: 501, 1996; Muller C. E., Exp. Opin. Ther. Patents, 7(5): 419, 1997).

Adenosine receptors belong to the superfamily of G-protein-coupled receptors (GPCRs). Four major subtypes of adenosine receptors have been pharmacologically, structurally and functionally characterized (Fredholm et al., Pharm. Rev., 46: 143-156, 1994) and referred to as $A_1$, $A_{2A}$, $A_{2B}$ and $A_3$. Though the same adenosine receptor can couple to different G-proteins, adenosine $A_1$ and $A_3$ receptors usually couple to inhibitory G-proteins referred to as $G_i$ and $G_0$ which inhibit adenylate cyclase and down-regulate cellular cAMP levels. In contrast, the adenosine $A_{2A}$ and $A_{2B}$ receptors couple to stimulatory G-proteins referred to as $G_s$ that activate adenylate cyclase and increase intracellular levels of cAMP (Linden J., Annu. Rev. Pharmacol. Toxicol., 41: 775-87 2001).

According to the invention, "adenosine-receptor-selective ligands" are substances which bind selectively to one or more subtypes of the adenosine receptors, thus either mimicking the action of adenosine (adenosine agonists) or blocking its action (adenosine antagonists). According to their receptor selectivity, adenosine-receptor-selective ligands can be divided into different categories, for example ligands which bind selectively to the $A_1$ or $A_2$ receptors and in the case of the latter also, for example, those which bind selectively to the $A_{2A}$ or the $A_{2B}$ receptors. Also possible are adenosine receptor ligands which bind selectively to a plurality of subtypes of the adenosine receptors, for example ligands which bind selectively to the $A_1$ and the $A_2$, but not to the $A_3$ receptors. The abovementioned receptor selectivity can be determined by the effect of the substances on cell lines which, after stable transfection with the corresponding cDNA, express the receptor subtypes in question (Olah, M. E. et al., J. Biol. Chem., 267: 10764-10770, 1992). The effect of the substances on such cell lines can be monitored by biochemical measurement of the intracellular messenger cAMP (Klotz, K. N. et al., Naunyn Schmiedebergs Arch. Pharmacol. 357: 1-9, 1998).

It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$ and $A_3$) or increase the oxygen supply ($A_{2A}$) and so reinstate the balance of energy supply/demand within the tissue. The actions of both subtype is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity. Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

These adenosine receptors are encoded by distinct genes and are classified according to their affinities for adenosine analogues and methylxanthine antagonists (Klinger et al., Cell Signal., 14 (2): 99-108, 2002).

Concerning the role of adenosine on the nervous system, the first observations were made on the effects of the most widely used of all psychoactive drugs being caffeine. Actually, caffeine is a well-known adenosine receptor antagonist that is able to enhance the awareness and learning abilities of mammals. The adenosine $A_{2A}$ receptor pathway is responsible for these effects (Fredholm et al., Pharmacol. Rev., 51 (1): 83-133, 1999; Huang et al., Nat Neurosci., 8 (7): 858-9, 2005), and the effects of caffeine on the adenosine $A_{2A}$ receptor signaling pathway encouraged the research of highly specific and potent adenosine $A_{2A}$ antagonists.

In mammals, adenosine $A_{2A}$ receptors have a limited distribution in the brain and are found in the striatum, olfactory tubercle and nucleus acumbens (Dixon et al., Br. J. Pharmacol., 118 (6): 1461-8, 1996). High and intermediate levels of expression can be observed in immune cells, heart, lung and blood vessels. In the peripheral system, $G_s$ seems to be the major G-protein associated with adenosine $A_{2A}$ receptor but in the striatum, it has been shown that striatal adenosine $A_{2A}$ receptors mediate their effects through activation of a G-protein referred to as $G_o$if (Kull et al., Mol. Pharmacol., 58 (4): 772-7, 2000), which is similar to $G_3$ and also couples to adenylate cyclase.

To date, studies on genetically modified mice and pharmacological analysis suggest that $A_{2A}$ receptor is a promising therapeutic target for the treatment of central nervous system (CNS) disorders and diseases such as Parkinson's disease, Huntington's disease, attention deficit hyperactivity disorders (ADHD), stroke (ischemic brain injury), and Alzheimer's disease (Fredholm et al., Annu. Rev. Pharmacol. Toxicol., 45: 385-412, 2005; Higgins et al.; Behav. Brain Res. 185: 32-42, 2007; Dall' Igna et al., Exp. Neurol., 203 (1): 241-5, 2007; Arendash et al., Neuroscience, 142 (4): 941-52, 2006; Trends in Neurosci., 29 (11), 647-654, 2006; Expert Opinion Ther. Patents, 17, 979-991, 2007; Exp. Neurol., 184 (1), 285-284, 2003; Prog. Brain Res, 183, 183-208, 2010; J. Alzheimer Dis., Suppl 1, 1 17-126, 2010; J. Neurosci., 29 (47), 14741-14751, 2009; Neuroscience, 166 (2), 590-603, 2010; J. Pharmacol. Exp. Ther., 330 (1), 294-303, 2009; Frontiers Biosci., 13, 2614-2632, 2008) but also for various psychoses of organic origin (Weiss et al., Neurology, 61 (11 Suppl 6): 88-93, 2003).

The use of adenosine $A_{2A}$ receptor knockout mice has shown that adenosine $A_{2A}$ receptor inactivation protects against neuronal cell death induced by ischemia (Chen et al., J. Neurosci., 19 (21): 9192-200, 1999 and Monopoli et al., Neuroreport, 9 (17): 3955-9, 1998) and the mitochondrial toxin 3-NP (Blum et al., J. Neurosci., 23 (12): 5361-9, 2003). Those results provided a basis for treating ischasmia and Huntington's disease with adenosine $A_{2A}$ antagonists. The blockade of adenosine $A_{2A}$ receptors has also an antidepressant effect (El Yacoubi et al., Neuropharmacology, 40 (3): 424-32, 2001). Finally, this blockade prevents memory dysfunction (Cunha et al., Exp. Neurol., 210 (2): 776-81, 2008; Takahashi et al., Front. Biosci., 13: 2614-32, 2008) and this could be a promising therapeutic route for the treatment and/or prevention of Alzheimer's disease.

For reviews concerning $A_{2A}$ adenosine receptors see e.g. Moreau et al. (Brain Res. Reviews 31: 65-82, 1999) and Svenningsson et al. (Progress in Neurobiology 59: 355-396, 1999).

To date, several adenosine $A_{2A}$ receptor antagonists have shown promising potential for treatment of Parkinson's disease. As an example, KW-6002 (Istradefylline) completed a phase III clinical trial in the USA after studies demonstrated its efficacy in alleviation of symptoms of the disease (Bara-Himenez et al., Neurology, 61 (3): 293-6, 2003 and Hauser et al., Neurology, 61 (3): 297-303, 2003). SCH420814 (Preladenant), which is now in phase II clinical trial in the USA and produces an improvement in motor function in animal models of Parkinson's disease (Neustadt et al., Bioorg. Med. Chem. Lett., 17 (5): 1376-80, 2001) and also in human patients (Hunter J. C, poster Boston 2006—http://www.a2apd.org/Speaker abstracts/Hunter.pdf).

Besides the welcome utility of $A_{2A}$ receptor antagonists to treat neurodegenerative diseases, those compounds have been considered for complementary symptomatic indications. These are based on the evidence that $A_{2A}$ receptor activation may contribute to the pathophysiology of a range of neuropsychiatric disorders and dysfunctions such as depression, excessive daytime sleepiness, restless legs syndrome, attention deficit hyperactivity disorder, and cognitive fatigue (Neurology, 61 (Suppl 6), 82-87, 2003; Behav. Pharmacol., 20 (2), 134-145, 2009; CNS Drug Discov., 2 (1), 1-21, 2007).

Some authors suggest the application of $A_{2A}$ antagonists for the treatment of diabetes (WO1999035147; WO2001002400). Other studies suggest the involvement of $A_{2A}$ adenosine receptors in wound healing or atrial fibrillation (Am. J. Path., 6, 1774-1778, 2007; Arthritis & Rheumatism, 54 (8), 2632-2642, 2006).

Some of the potent adenosine $A_{2A}$ antagonists discovered in the past by the pharmaceutical companies, have advanced into clinical trials showing positive results and demonstrating the potential of this compound class for the treatment of neurodegenerative disorders like Parkinson's, Huntington's or Alzheimer's disease, but also in other CNS related diseases like depression, restless syndrome, sleep and anxiety disorders (Clin. Neuropharmacol., 33, 55-60, 2010; J. Neurosci., 30 (48), 2010), 16284-16292; Parkinson Relat. Disord., 16 (6), 423-426, 2010; Expert Opinion Ther. Patents, 20(8), 987-1005, 2010; Current Opinion in Drug Discovery & Development, 13 (4), 466-480, 2010 and references therein; Mov. Disorders, 25 (2), S305, 2010).

Known $A_{2A}$ inhibitors are Istradefylline (KW-6002), Preladenant (SCH420814), SCH58261, CGS15943, Tozadenant, Vipadenant (V-2006), V-81444 (CPI-444, HTL-1071, PBF-509, Medi-9447, PNQ-370, ZM-241385, ASO-5854, ST-1535, ST-4206, DT1133 and DT-0926, which are in most cases developed for Parkinson's disease.

Adenosine $A_{2B}$ receptors were cloned from rat hypothalamus (Rivkees and Reppert, 1992), human hippocampus (Pierce et al., 1992), and mouse mast cells (Marquardt et al., 1994), employing standard polymerase chain reaction techniques with degenerate oligonucleotide primers designed to recognize conserved regions of most G protein-coupled receptors. The human $A_{2B}$ receptor shares 86 to 87% amino acid sequence homology with the rat and mouse $A_{2B}$ receptors (Rivkees and Reppert, 1992; Pierce et al., 1992; Marquardt et al., 1994) and 45% amino acid sequence homology with human $A_1$ and $A_{2A}$ receptors. As expected for closely related species, the rat and mouse $A_{2B}$ receptors share 96% amino acid sequence homology. By comparison, the overall amino acid identity between $A_1$ receptors from various species is 87% (Palmer and Stiles, 1995). $A_{2A}$ receptors share 90% of homology between species (Ongini and Fredholm, 1996), with most differences occurring in the $2^{nd}$ extracellular loop and the long C-terminal domain (Palmer and Stiles, 1995). The lowest (72%) degree of identity between species is observed for $A_3$ receptor sequences (Palmer and Stiles, 1995).

The adenosine analog NECA remains the most potent $A_{2B}$ agonist (Bruns, 1981; Feoktistov and Biaggioni, 1993, 1997; Brackett and Daly, 1994), with a concentration producing a half-maximal effect ($EC_{50}$) for stimulation of adenyl cyclase of approximately 2 µM. It is, however, nonselective and activates other adenosine receptors with even greater affinity, with an $EC_{50}$ in the low nanomolar ($A_1$ and $A_{2A}$) or high nanomolar ($A_3$) range. The characterization of $A_{2B}$ receptors, therefore, often relies on the lack of effectiveness of compounds that are potent and selective agonists of other receptor types. $A_{2B}$ receptors have been characterized by a method of exclusion, i.e., by the lack of efficacy of agonists that are specific for other receptors. The $A_{2A}$ selective agonist CGS-21680 (Webb et al., 1992), for example, has been useful in differentiating between $A_{2A}$ and $A_{2B}$ adenosine receptors (Hide et al., 1992; Chern et al., 1993; Feoktistov and Biaggioni, 1995; van der Ploeg et al., 1996). Both receptors are positively coupled to adenyl cyclase and are activated by the nonselective agonist NECA. CGS-21680 is virtually ineffective on $A_{2B}$ receptors but is as potent as NECA in activating $A_{2A}$ receptors, with an $EC_{50}$ in the low nanomolar range for both agonists (Jarvis et al., 1989; Nakane and Chiba, 1990; Webb et al., 1992; Hide et al., 1992; Feoktistov and Biaggioni, 1993; Alexander et al., 1996). $A_{2B}$ receptors have also a very low affinity for the $A_1$ selective agonist R-PIA (Feoktistov and Biaggioni, 1993; Brackett and Daly, 1994) as well as for the $A_3$ selective agonist $N^6$-(3-iodobenzyl)-N-methyl-5'-carbamoyladenosine (IB-MECA) (Feoktistov and Biaggioni, 1997). The agonist profile NECA>R-PIA=IB-MECA>CGS-21680 was determined in human erythroleukemia (HEL) cells for $A_{2B}$-mediated cAMP accumulation. The difference between $EC_{50}$ for NECA and the rest of the agonists is approximately 2 orders of magnitude. Therefore, responses elicited by NECA at concentrations in the low micromolar range (1-10 μM), but not by R-PIA, IB-MECA or CGS-21680, are characteristic of $A_{2B}$ receptors.

Whereas $A_{2B}$ receptors have, in general, a lower affinity for agonists compared to other receptor subtypes, this is not true for antagonists. The structure activity relationship of adenosine antagonists on $A_{2B}$ receptors has not been fully characterized, but at least some xanthines are as or more potent antagonists of $A_{2B}$ receptor subtypes than of other subtypes. In particular, DPSPX (1,3-dipropyl-8-sulphophenylxanthine), DPCPX (1,3-diproyl-8c-yclopentylxanthine), DPX (1,3 diethylphenylxanthine), the antiasthmatic drug enprofylline (3-n-propylxanthine) and the non-xanthine compound 2,4-dioxobenzopteridine (alloxazine) have affinities in the mid to high nM range.

Other known $A_{2B}$ inhibitors are ATL801, PSB-605, PSB-1115, ISAM-140, GS6201, MRS1706 and MRS1754.

It is disclosed herein that adenosine receptors play a non-redundant role in downregulation of inflammation in vivo by acting as a physiological "STOP" (a termination mechanism) that can limit the immune response and thereby protect normal tissues form excessive immune damage during pathogenesis of different diseases.

$A_{2A}$ receptor antagonists provide long term enhancement of immune responses by reducing T-cell mediated tolerance to antigenic stimuli, enhancing the induction of memory T cells and enhancing the efficacy of passive antibody administration for the treatment of cancer and infectious diseases while $A_{2A}$ receptor agonists provide long term reduction of immune responses by enhancing T-cell mediated tolerance to antigenic stimuli, in particular to reduce use of immunosuppressive agents in certain conditions.

Immune modulation is a critical aspect of the treatment of a number of diseases and disorders. T cells in particularly play a vital role in fighting infections and have the capability to recognize and destroy cancer cells. Enhancing T cell mediated responses is a key component to enhancing responses to therapeutic agents. However, it is critical in immune modulation that any enhancement of an immune response is balanced against the need to prevent autoimmunity as well as chronic inflammation. Chronic inflammation and self-recognition by T cells is a major cause for the pathogenesis of systemic disorders such as rheumatoid arthritis, multiple sclerosis and systemic lupus erythematosus. Furthermore, long term immunosuppression is required in preventing rejection of transplanted organs or grafts.

Tumor-induced immunosuppression is a major hurdle to the efficacy of current cancer therapies. Because of their remarkable clinical efficacy against a broader range of cancers, recent successes with immune checkpoint blockade inhibitors such as anti-CTLA-4 and anti-PD-1/PDL1 are revolutionizing cancer treatment. Adenosine is one of the new promising immunosuppressive targets revealed in preclinical studies. This metabolite is produced by the ectoenzyme—CD73 expressed on host suppressor cells and tumor cells. Increased expression of CD73 correlates with poor prognosis in patients with a number of cancers, including colorectal cancer (Liu et al, J. Surgical Oncol, 2012), gastric cancer (Lu et al., World J. Gastroenterol., 2013), gallbladder cancer (Xiong et al., Cell and Tissue Res., 2014). Preclinical studies demonstrated that protumor effects of CD73 can be driven (at least in part) by adenosine-mediated immunosuppression. As disclosed above, adenosine binds to four known receptors $A_1$, $A_{2A}$, $A_{2B}$, and $A_3$, with the activation of $A_{2A}$ and $A_{2B}$ receptors known to suppress the effector functions of many immune cells, i.e. $A_{2A}$ and $A_{2B}$ receptors induce adenylate-cyclase-dependent accumulation of cAMP leading to immunosuppression. Since antagonizing $A_1$ and $A_3$ would counteract the desired effect and $A_1$ and $A_3$ agonists serve as potential cardioprotective agents, selectivity towards $A_1$ and $A_3$ needs to be achieved (Antonioli et al., Nat. rev. Cancer, 2013, Thiel et al., Microbes and Infection, 2003). In the microenvironment of the tumor, both $A_{2A}$ and $A_{2B}$ receptor activation has been demonstrated to suppress antitumor immunity and increase the spread of CD73 tumors. In addition, either $A_{2A}$ or $A_{2B}$ blockade with small molecule antagonists can reduce tumor metastasis. It has been found that blocking of $A_{2A}$ receptor can overcome tumor escape mechanisms including both anergy and regulatory T cell induction caused by tumor cells and cause long-term tumor susceptibility to treatment. Ohta et al. demonstrated rejection of approximately 60% of established CL8-1 melanoma tumors in $A_{2A}$ receptor-deficient mice compared to no rejection in normal mice (Ohta, et al.; PNAS 103 (35): 13132-7, 2006). In agreement, the investigators also showed improved inhibition of tumor growth, destruction of metastases and prevention of neovascularization by anti-tumor T cells after treatment with an $A_{2A}$ receptor antagonist.

Tumors have been shown to evade immune destruction by impeding T cell activation through inhibition of co-stimulatory factors in the B7-CD28 and TNF families, as well as by attracting regulatory T cells, which inhibit anti-tumor T cell responses (Wang, Cancer. Semin. Cancer. Biol. 16: 73-79, 2006; Greenwald, et al., Ann. Rev. Immunol. 23: 515-48, 2005; Watts, Ann. Rev. Immunol. 23: 23-68, 2005; Sadum et al., Clin. Canc. Res. 13 (13): 4016-4025, 2007). Because $A_{2A}$ receptor expression is increased in lymphocytes following activation, therapies that liberate lymphocyte effector responses, such as anti-CTLA-4 and anti-PD-1, may also increase the effects of $A_{2A}$-mediated immunosuppression. Immune checkpoint blockade in combination with $A_{2A}$ or dual $A_{2A/2B}$ antagonists increase the magnitude of immune responses to tumors and metastasis. Accordingly, combination of $A_{2A}$ inhibition with anti-PD-1 therapy enhances IFN-γ production by T-cells in a co-culture with MC38 tumor cells, improves mouse survival in 4T1 mammary tumor model and decreases tumor growth in AT-3ova$^{dim}$ CD73$^+$ tumors (Beavis et al., Cancer Immunol. Res., 2015; Mittal et al., Cancer Res., 2014).

Furthermore, preclinical studies demonstrated that $A_{2B}$ inhibition leads to decreased tumor growth and extended survival of mice in Lewis lung carcinoma, MB49 bladder carcinoma, ortho 4T1 mammary carcinoma models (Ryzhov et al., 2009, Cekic et al., 2012) and the combination of $A_{2B}$ inhibition with anti-PD-1 therapy reduces lung metastases of B16-F10 melanoma tumors and improves mouse survival in the 4T1 mammary tumor model.

WO 03/050241 describes the methods to increase an immune response to an antigen, increasing vaccine efficacy or increasing an immune response to a tumor antigen or immune cell-mediated tumor destruction by administering an agent that inhibits extracellular adenosine or inhibits adenosine receptors.

WO 2004/089942, WO 2005/000842 and WO 2006/008041 disclose benzothiazole derivatives, including Tozadenant, as $A_{2A}$ inhibitors for the treatment of Parkinson's disease. WO 2004/092171 and WO 2005/028484 disclose similar thiazolopyridine and pyrazolopyrimidine derivatives also as $A_{2A}$ inhibitors for the treatment of Parkinson's disease. However, these compounds do not show significant $A_{2B}$ inhibitory activity and do only show good pharmacokinetic properties in the rat, the Parkinson's disease animal model but not in the mouse, the cancer animal model. Furthermore, the compounds do not show that they are able to prevent immunosuppression and thus are able to support anti-tumor T cell induced inhibition of tumor growth, reduction or destruction of metastases and prevention of neovascularization.

Thus, there remains a need for therapies that provide long term enhancement of immune responses to specific antigens, particularly for the treatment and prevention of hyperproliferative and infectious diseases and disorders and thus the object of the present invention was to provide methods of treatment that allow simplified treatment protocols and enhance immune responses against certain antigens. It was a specific object of the invention to provide improved methods of preventing or treating hyperproliferative and infectious diseases and disorders in a host, especially to provide effective $A_{2A}$ or dual $A_{2A/2B}$ antagonists for the treatment and prevention of such diseases.

SUMMARY OF THE INVENTION

Surprisingly, it has been found that the quinoxaline derivatives according to the invention are highly effective inhibitors of the $A_{2A}$ adenosine receptor or both the $A_{2A}$ and $A_{2B}$ adenosine receptors and at the same time have high selectivity over the $A_1$ and $A_3$ adenosine receptors, and thus the compounds of the present invention can be used for the treatment of hyperproliferative diseases and disorders such as cancer and infectious diseases and disorders.

Particularly, in contrast to the known adenosine $A_{2A}$ receptor antagonist Tozadenant and similar benzothiazole derivatives, the compounds of the present invention surprisingly show an $A_{2A}/A_{2B}$ dual activity which is preferred for the treatment and/or prevention of hyperproliferative and infectious diseases and disorders as it is disclosed above or the compounds of the present invention show at least a high $A_{2A}$ inhibitory activity together with the other surprising advantages disclosed herein leading to a high efficacy in the treatment and/or prevention of hyperproliferative and infectious diseases and disorders.

Additionally, in comparison with the known adenosine $A_{2A}$ receptor antagonist Tozadenant and similar benzothiazole derivatives, the compounds of the present invention surprisingly show better pharmacokinetic properties in mouse as the animal model relevant for cancer, which is preferred for the treatment and/or prevention of hyperproliferative and infectious diseases and disorders as it is disclosed above.

Furthermore, as discussed above, adenosine in tumor microenvironment can inhibit T cell activity by signaling through $A_{2A}$ receptors and suppress cytokine secretion by T cells. $A_{2A}$ specific agonists like CGS-21680, similar to adenosine, inhibit T cell cytokine secretion in vitro and in vivo. In contrast, potential $A_{2A}$ antagonists or $A_{2A}/A_{2B}$ dual antagonists can rescue T cells from this inhibition. In contrast to the known adenosine $A_{2A}$ receptor antagonist Tozadenant, the compounds of the present invention show that they are able to rescue T cells from inhibition and are able to prevent the suppression of cytokine secretion as induced by adenosine or $A_{2A}$ specific agonists like CGS-2168, which is preferred for the treatment and/or prevention of hyperproliferative and infectious diseases and disorders as it is disclosed above. Therefore, the compounds of the present invention surprisingly are able to prevent immunosuppression and thus are able to support anti-tumor T cell induced inhibition of tumor growth, reduction or destruction of metastases and prevention of neovascularization.

The invention relates to quinoxaline derivatives of the general formula I,

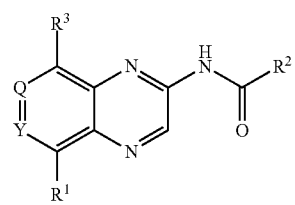

I wherein
Q, Y are independently of one another CH or N,
$R^1$ is Hal or linear or branched alkyl having 1-10 C atoms which is unsubstituted or mono-, di- or trisubstituted by $R^4$ and in which 1-4 C atoms may be replaced, independently of one another, by O, S, SO, $SO_2$, NH, $NCH_3$, —OCO—, —NHCONH—, —NHCO—, —$NR^5SO_2R^6$—, —COO—, —CONH—, —$NCH_3CO$—, —$CONCH_3$—, —C≡C— groups and/or —CH=CH— groups, and/or, in addition, 1-10 H atoms may be replaced by F and/or Cl, or mono- or bicyclic cyclic alkyl having 3-7 C atoms which is unsubstituted or mono-, di- or trisubstituted by $R^4$ and in which 1-4 C atoms may be replaced, independently of one another, by O, S, SO, $SO_2$, NH, $NCH_3$, —OCO—, —NHCONH—, —NHCO—, —$NR^5SO_2R^6$—, —COO—, —CONH—, —$NCH_3CO$—, —$CONCH_3$—, —C≡C— groups and/or by —CH=CH— groups and/or, in addition, 1-10 H atoms may be replaced by F and/or Cl, or mono- or bicyclic heteroaryl, heterocyclyl, aryl or cyclic alkylaryl, containing 3 to 14 carbon atoms and 0-4 heteroatoms, independently selected from N, O and S, which is unsubstituted or mono-, di- or trisubstituted by $R^4$,
$R^2$ is linear or branched alkyl having 1-10 C atoms which is unsubstituted or mono-, di- or trisubstituted by $R^4$ and in which 1-4 C atoms may be replaced, independently of one another, by O, S, SO, $SO_2$, NH, $NCH_3$, —OCO—, —NHCONH—, —NHCO—, —$NR^5SO_2R^6$—, —COO—, —CONH—, —$NCH_3CO$—, —$CONCH_3$—, —C≡C— groups and/or —CH=CH— groups, and/or, in addition, 1-10 H atoms may be replaced by F and/or Cl, or cyclic alkyl having 3-7 C atoms which is unsubstituted or mono-, di- or trisubstituted by $R^4$ and in which 1-4 C atoms may be replaced, independently of one another, by O, S, SO, $SO_2$, NH, $NCH_3$, —OCO—, —NHCONH—, —NHCO—, —$NR^5SO_2R^6$—, —COO—, —CONH—, —$NCH_3CO$—, —$CONCH_3$—, —C≡C— groups and/or by —CH=CH— groups and/or, in addition, 1-11 H atoms may be replaced by F and/or Cl, or mono- or bicyclic heteroaryl, heterocyclyl, aryl or cyclic alkylaryl, containing 3 to 14 carbon atoms and 0-4 heteroatoms, independently selected from N, O and S, which is unsubstituted or mono-, di- or trisubstituted by $R^4$, $R^3$ is linear or branched alkyl or O-alkyl having 1-6 C atoms or cyclic alkyl having 3-6 C atoms, which is unsubstituted or mono-, di- or trisubstituted by H, =S, =NH, =O, OH, cyclic alkyl having 3-6 C atoms, COOH, Hal, $NH_2$, $SO_2CH_3$, $SO_2NH_2$, CN, $CONH_2$, $NHCOCH_3$, $NHCONH_2$ or $NO_2$, $R^4$ is H, $R^5$, =S, =$NR^5$, =O, OH, COOH, Hal, $NH_2$, $SO_2CH_3$, $SO_2NH_2$, CN, $CONH_2$, $NHCOCH_3$, $NHCONH_2$, $NO_2$, or linear or branched alkyl having 1-10 C atoms which is unsubstituted or mono-, di- or trisubstituted by $R^5$ and in which 1-4 C atoms may be replaced, independently of one another, by O, S, SO, $SO_2$, NH, $NCH_3$, —OCO—, —NHCONH—, —NHCO—, —$NR^5SO_2R^6$—, —COO—, —CONH—, —$NCH_3CO$—, —$CONCH_3$—, —C≡C— groups and/or —CH=CH— groups, and/or, in addition, 1-10 H atoms may be replaced by F and/or Cl, or mono- or bicyclic cyclic alkyl having 3-7 C atoms which is unsubstituted or mono-, di- or trisubstituted by $R^5$ and in which 1-4 C atoms may be replaced, independently of one another, by O, S, SO, $SO_2$, NH, $NCH_3$, —OCO—, —NHCONH—, —NHCO—, —$NRSO_2R^4$—, —COO—, —CONH—, —$NCH_3CO$—, —$CONCH_3$—, —C≡C— groups and/or by —CH=CH— groups and/or, in addition, 1-10 H atoms may be replaced by F and/or Cl, or mono- or bicyclic heteroaryl, heterocyclyl, aryl or cyclic alkylaryl, containing 3 to 14 carbon atoms and 0-4 heteroatoms, independently selected from N, O and S, which is unsubstituted or mono-, di- or trisubstituted by $R^5$, $R^5$, $R^6$ are independently of one another selected from the group consisting of H, =S, =NH, =O, OH, COOH, Hal, $NH_2$, $SO_2CH_3$, $SO_2NH_2$, CN, $CONH_2$, $NHCOCH_3$, $NHCONH_2$, $NO_2$ and linear or branched alkyl having 1-10 C atoms in which 1-4 C atoms may be replaced, independently of one another, by O, S, SO, $SO_2$, NH, $NCH_3$, —COO—, —NHCONH—, —NHCO—, —COO—, —CONH—, —$NCH_3CO$—, —$CONCH_3$—, —C≡C— groups and/or —CH=CH— groups, and/or, in addition, 1-10 H atoms may be replaced by F and/or Cl, Hal is F, C, Br, or I, and physiologically acceptable salts, derivatives, solvates, prodrugs and stereoisomers thereof, including mixtures thereof in all ratios.

The invention preferably relates to a compound of formula I, wherein $R^1$ is Hal or linear or branched alkyl having 1-10 C atoms which is unsubstituted or mono-, di- or trisubstituted by $R^4$ and in which 1-4 C atoms may be replaced, independently of one another, by O, S, SO, $SO_2$, NH, $NCH_3$, —COO—, —NHCONH—, —NHCO—, —$NR^5SO_2R^6$—, —COO—, —CONH—, —$NCH_3CO$—, —$CONCH_3$—, —C≡C— groups and/or —CH=CH— groups, and/or, in addition, 1-10 H atoms may be replaced by F and/or Cl, or one of the following structures:

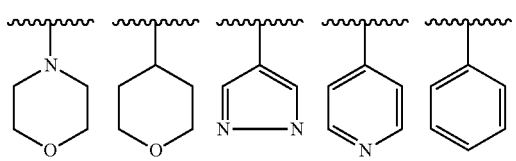

which is unsubstituted or mono-, di- or trisubstituted with $R^4$ and wherein Q, Y, $R^2$, $R^3$, $R^4$, $R^5$ and $R^6$ have the meanings as disclosed above.

The invention preferably relates to a compound of formula I, wherein

Q is CH or N

Y is CH and wherein $R^1$, $R^2$, $R^3$, $R^4$, $R^5$ and $R^6$ have the meanings as disclosed in claim 1, and physiologically acceptable salts, derivatives, solvates, prodrugs and stereoisomers thereof, including mixtures thereof in all ratios.

The invention particularly preferably relates to a compound of formula I, wherein $R^2$ is one of the following structures:

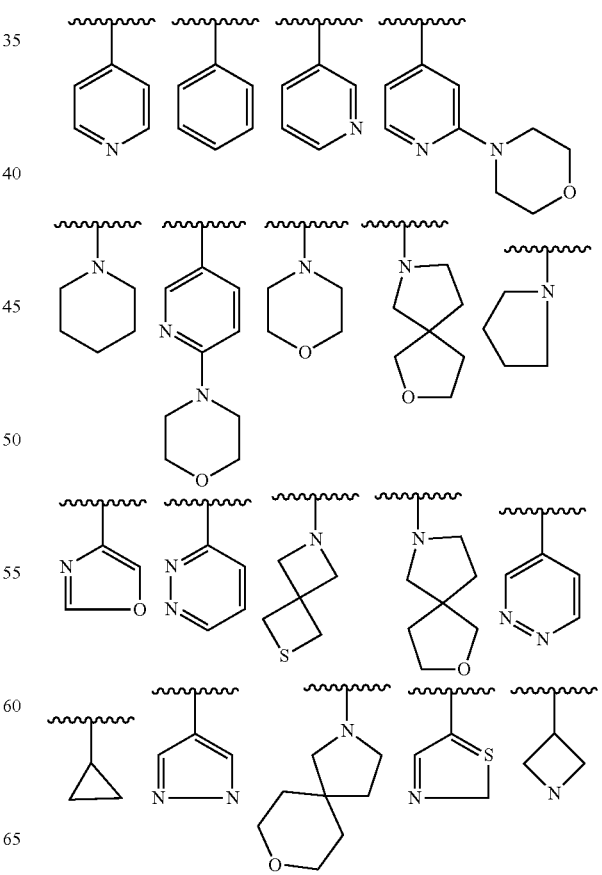

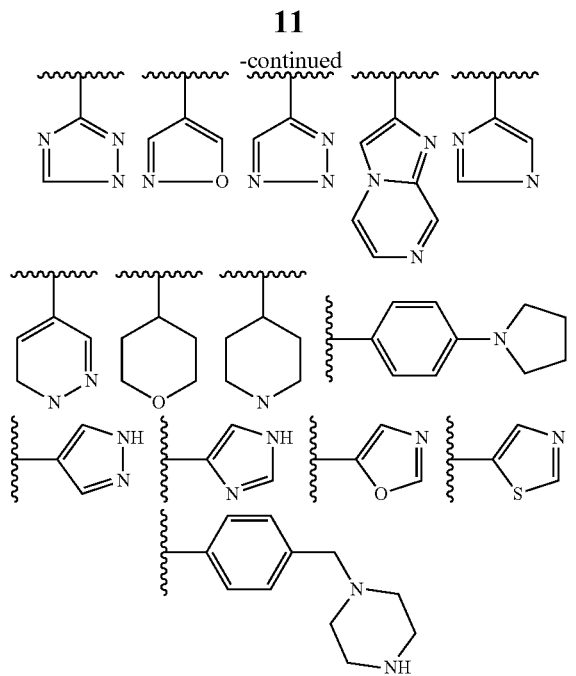

which is unsubstituted or mono-, di- or trisubstituted with R⁵ and wherein Q, Y, R¹, R³, R⁴, R⁵ and R⁶ have the meanings as disclosed above.

The invention preferably relates to a compound of formula I, wherein
R³ one of the following structures

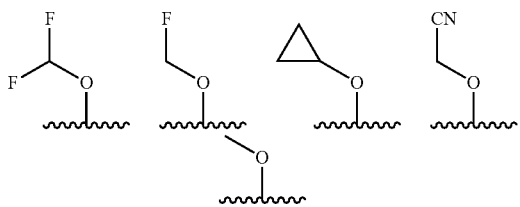

and Q, Y, R¹, R², R⁴, R⁵ and R⁶ have the meanings as disclosed above.

The invention preferably relates to a compound of formula I, wherein
R³ is O-alkyl having 1-6 C atoms, which is unsubstituted or mono-, di- or trisubstituted with F
and Q, Y, R¹, R², R⁴, R⁵ and R⁶ have the meanings as disclosed above.

The invention preferably relates to a compound of formula I, wherein
R³ is OMe
and Q, Y, R¹, R², R⁴, R⁵ and R⁶ have the meanings as disclosed above.

The invention particularly preferably relates to a compound selected from the group consisting of:

| No. | IUPAC-Name |
|---|---|
| 1 | N-[8-methoxy-5-(oxan-4-yl)quinoxalin-2-yl]-2-oxa-7-azaspiro[4.4]nonane-7-carboxamide |
| 2 | 4-hydroxy-N-[8-methoxy-5-(pyridin-4-yl)quinoxalin-2-yl]-4-methylpiperidine-1-carboxamide |
| 3 | 3-hydroxy-N-[8-methoxy-5-(oxan-4-yl)quinoxalin-2-yl]-3-methylpyrrolidine-1-carboxamide |
| 4 | N-[8-methoxy-5-(oxan-4-yl)quinoxalin-2-yl]-2-methyl-1,3-oxazole-4-carboxamide |
| 5 | 4-(hydroxymethyl)-N-[8-methoxy-5-(oxan-4-yl)quinoxalin-2-yl]-4-methylpiperidine-1-carboxamide |
| 6 | N-[8-methoxy-5-(oxan-4-yl)quinoxalin-2-yl]-2,2-dioxo-2lambda6-thia-6-azaspiro[3.3]heptane-6-carboxamide |
| 7 | 6-methoxy-N-[8-methoxy-5-(oxan-4-yl)quinoxalin-2-yl]pyridazine-3-carboxamide |
| 8 | N-[8-methoxy-5-(oxan-4-yl)quinoxalin-2-yl]-1-(2-methoxyethyl)-1H-pyrazole-4-carboxamide |
| 9 | 4-hydroxy-N-(8-methoxy-5-phenylquinoxalin-2-yl)-4-(prop-2-yn-1-yl)piperidine-1-carboxamide |
| 10 | 3-hydroxy-N-(8-methoxy-5-phenylquinoxalin-2-yl)-3-methylpyrrolidine-1-carboxamide |
| 11 | 4-(hydroxymethyl)-N-(8-methoxy-5-phenylquinoxalin-2-yl)-4-methylpiperidine-1-carboxamide |
| 12 | N-(8-methoxy-5-phenylquinoxalin-2-yl)-8-oxa-2-azaspiro[4.5]decane-2-carboxamide |
| 13 | N-(8-methoxy-5-phenylquinoxalin-2-yl)-2-oxa-7-azaspiro[4.4]nonane-7-carboxamide |
| 14 | N-(8-methoxy-5-phenylquinoxalin-2-yl)-2,2-dioxo-2lambda6-thia-6-azaspiro[3.3]heptane-6-carboxamide |
| 15 | 4-Hydroxy-4-methyl-piperidine-1-carboxylic acid (5-methoxy-8-phenyl-pyrido[3,4-b]pyrazin-3-yl)-amide |
| 16 | 3-Hydroxy-3-methyl-pyrrolidine-1-carboxylic acid (5-methoxy-8-phenyl-pyrido[3,4-b]pyrazin-3-yl)-amide |
| 17 | 4-Hydroxymethyl-4-methyl-piperidine-1-carboxylic acid (5-methoxy-8-phenyl-pyrido[3,4-b]pyrazin-3-yl)-amide |
| 18 | N-[8-methoxy-5-(oxan-4-yl)quinoxalin-2-yl]-8-oxa-2-azaspiro[4.5]decane-2-carboxamide |
| 19 | N-[8-methoxy-5-(oxan-4-yl)quinoxalin-2-yl]acetamide |
| 20 | 2,2,2-trifluoro-N-[8-methoxy-5-(oxan-4-yl)quinoxalin-2-yl]acetamide |
| 21 | 4-Dimethylaminomethyl-N-(5-methoxy-8-phenyl-pyrido[3,4-b]pyrazin-3-yl)-benzamide |
| 22 | 4-Hydroxy-4-prop-2-ynyl-piperidine-1-carboxylic acid (5-methoxy-8-phenyl-pyrido[3,4-b]pyrazin-3-yl)-amide |
| 23 | 4-Methoxymethyl-N-(5-methoxy-8-phenyl-pyrido[3,4-b]pyrazin-3-yl)-benzamide |
| 24 | 1-(2-Methoxy-ethyl)-1H-pyrazole-4-carboxylic acid (5-methoxy-8-phenyl-pyrido[3,4-b]pyrazin-3-yl)-amide |
| 25 | 6-hydroxy-N-[8-methoxy-5-(oxan-4-yl)quinoxalin-2-yl]pyridazine-4-carboxamide |
| 26 | 8-methoxy-5-(oxan-4-yl)quinoxalin-2-amine |
| 27 | (3S)-3-hydroxy-N-[8-methoxy-5-(oxan-4-yl)quinoxalin-2-yl]-3-methylpyrrolidine-1-carboxamide |
| 28 | (3R)-3-hydroxy-N-[8-methoxy-5-(oxan-4-yl)quinoxalin-2-yl]-3-methylpyrrolidine-1-carboxamide |
| 29 | 4-hydroxy-N-[8-methoxy-5-(2-methylphenyl)quinoxalin-2-yl]-4-methylpiperidine-1-carboxamide |
| 30 | N-(8-methoxy-5-phenylquinoxalin-2-yl)-1-(2-methoxyethyl)-1H-pyrazole-4-carboxamide |
| 31 | N-(8-methoxy-5-phenylquinoxalin-2-yl)-2-methyl-1,3-oxazole-4-carboxamide |
| 32 | N-(8-methoxy-5-phenylquinoxalin-2-yl)-1-methyl-1H-pyrazole-4-carboxamide |
| 33 | N-(8-methoxy-5-phenylquinoxalin-2-yl)cyclopropanecarboxamide |
| 34 | N-(8-methoxy-5-phenylquinoxalin-2-yl)-1-methyl-1H-pyrazole-5-carboxamide |
| 35 | N-(8-methoxy-5-phenylquinoxalin-2-yl)-1,3-thiazole-5-carboxamide |
| 36 | N-(8-methoxy-5-phenylquinoxalin-2-yl)-2-methyl-1,3-thiazole-5-carboxamide |
| 37 | N-(8-methoxy-5-phenylquinoxalin-2-yl)-4H-1,2,4-triazole-3-carboxamide |
| 38 | N-[5-(4-fluorophenyl)-8-methoxyquinoxalin-2-yl]-4-hydroxy-4-methylpiperidine-1-carboxamide |
| 39 | 4-Hydroxy-4-methyl-piperidine-1-carboxylic acid [5-methoxy-8-(tetrahydro-pyran-4-yl)-pyrido[3,4-b]pyrazin-3-yl]-amide |
| 40 | N-[8-methoxy-5-(oxan-4-yl)quinoxalin-2-yl]cyclopropanecarboxamide |
| 41 | 4-Hydroxy-4-methyl-piperidine-1-carboxylic acid [8-methoxy-5-(6-methyl-pyridazin-3-yl)-quinoxalin-2-yl]-amide |
| 42 | 1-(2-Methoxy-ethyl)-1H-pyrazole-4-carboxylic acid [8-methoxy-5-(6-methyl-pyridazin-3-yl)-quinoxalin-2-yl]-amide |

| No. | IUPAC-Name |
|---|---|
| 43 | 1-(2-Methoxy-ethyl)-1H-pyrazole-4-carboxylic acid (8-methoxy-5-pyridin-4-yl-quinoxalin-2-yl)-amide |
| 44 | 1-(2-Methoxy-ethyl)-1H-pyrazole-4-carboxylic acid [5-methoxy-8-(tetrahydro-pyran-4-yl)-pyrido[3,4-b]pyrazin-3-yl]-amide |
| 45 | Isoxazole-4-carboxylic acid (5-methoxy-8-phenyl-pyrido[3,4-b]pyrazin-3-yl)-amide |
| 46 | 4-Hydroxymethyl-4-methyl-piperidine-1-carboxylic acid [8-methoxy-5-(tetrahydro-pyran-4-yl)-quinoxalin-2-yl]-amide |
| 47 | 3-Hydroxy-3-methyl-pyrrolidine-1-carboxylic acid [5-methoxy-8-(tetrahydro-pyran-4-yl)-pyrido[3,4-b]pyrazin-3-yl]-amide |
| 48 | 4-Hydroxy-4-methyl-piperidine-1-carboxylic acid [5-(2-fluoro-phenyl)-8-methoxy-quinoxalin-2-yl]-amide |
| 49 | 4-Hydroxy-4-methyl-piperidine-1-carboxylic acid [5-(4-fluoro-phenyl)-8-methoxy-quinoxalin-2-yl]-amide |
| 50 | 4-Hydroxy-4-methyl-piperidine-1-carboxylic acid [5-(3-fluoro-phenyl)-8-methoxy-quinoxalin-2-yl]-amide |
| 51 | 4-Hydroxy-4-methyl-piperidine-1-carboxylic acid [8-methoxy-5-(2-oxa-7-aza-spiro[4.4]non-7-yl)-quinoxalin-2-yl]-amide |
| 52 | 4-Hydroxy-4-methyl-piperidine-1-carboxylic acid (8-methoxy-5-pyridin-3-yl-quinoxalin-2-yl)-amide |
| 53 | 4-Hydroxy-4-methyl-piperidine-1-carboxylic acid (5-azepan-1-yl-8-methoxy-quinoxalin-2-yl)-amide |
| 54 | 4-Hydroxy-4-methyl-piperidine-1-carboxylic acid (8-methoxy-5-phenyl-pyrido[3,4-b]pyrazin-2-yl)-amide |
| 55 | Isoxazole-4-carboxylic acid [5-methoxy-8-(tetrahydro-pyran-4-yl)-pyrido[3,4-b]pyrazin-3-yl]-amide |
| 56 | 1-Methyl-1H-pyrazole-4-carboxylic acid [8-methoxy-5-(tetrahydro-pyran-4-yl)-quinoxalin-2-yl]-amide |
| 57 | 5-Methyl-isoxazole-4-carboxylic acid [8-methoxy-5-(tetrahydro-pyran-4-yl)-quinoxalin-2-yl]-amide |
| 58 | 5-Cyclopropyl-isoxazole-4-carboxylic acid [8-methoxy-5-(tetrahydro-pyran-4-yl)-quinoxalin-2-yl]-amide |
| 59 | 1-(2-Methoxy-ethyl)-1H-[1,2,3]triazole-4-carboxylic acid [8-methoxy-5-(tetrahydro-pyran-4-yl)-quinoxalin-2-yl]-amide |
| 60 | 1-Methyl-1H-[1,2,3]triazole-4-carboxylic acid [8-methoxy-5-(tetrahydro-pyran-4-yl)-quinoxalin-2-yl]-amide |
| 61 | 1-Cyano-cyclopropanecarboxylic acid [8-methoxy-5-(tetrahydro-pyran-4-yl)-quinoxalin-2-yl]-amide |
| 62 | Cyclopropanesulfonic acid [8-methoxy-5-(tetrahydro-pyran-4-yl)-quinoxalin-2-yl]-amide |
| 63 | [8-Methoxy-5-(tetrahydro-pyran-4-yl)-quinoxalin-2-yl]-carbamic acid isopropyl ester |
| 64 | 2-Methyl-2H-pyrazole-3-carboxylic acid [8-methoxy-5-(tetrahydro-pyran-4-yl)-quinoxalin-2-yl]-amide |
| 65 | Thiazole-5-carboxylic acid [8-methoxy-5-(tetrahydro-pyran-4-yl)-quinoxalin-2-yl]-amide |
| 66 | 2-Methyl-thiazole-5-carboxylic acid [8-methoxy-5-(tetrahydro-pyran-4-yl)-quinoxalin-2-yl]-amide |
| 67 | 1H-[1,2,4]Triazole-3-carboxylic acid [8-methoxy-5-(tetrahydro-pyran-4-yl)-quinoxalin-2-yl]-amide |
| 68 | 2,3-Dimethyl-3H-imidazole-4-sulfonic acid [8-methoxy-5-(tetrahydro-pyran-4-yl)-quinoxalin-2-yl]-amide |
| 69 | Imidazo[1,2-a]pyrazine-2-carboxylic acid [8-methoxy-5-(tetrahydro-pyran-4-yl)-quinoxalin-2-yl]-amide |
| 70 | Azetidine-3-carboxylic acid [8-methoxy-5-(tetrahydro-pyran-4-yl)-quinoxalin-2-yl]-amide |
| 71 | Azetidine-3-carboxylic acid (8-methoxy-5-phenyl-quinoxalin-2-yl)-amide |
| 72 | Imidazo[1,2-a]pyrazine-2-carboxylic acid (8-methoxy-5-phenyl-quinoxalin-2-yl)-amide |
| 73 | 2,3-Dimethyl-3H-imidazole-4-sulfonic acid (8-methoxy-5-phenyl-quinoxalin-2-yl)-amide |
| 74 | (8-Methoxy-5-phenyl-quinoxalin-2-yl)-carbamic acid isopropyl ester |
| 75 | Cyclopropanesulfonic acid (8-methoxy-5-phenyl-quinoxalin-2-yl)-amide |
| 76 | 1-Cyano-cyclopropanecarboxylic acid (8-methoxy-5-phenyl-quinoxalin-2-yl)-amide |
| 77 | 1-Methyl-1H-[1,2,3]triazole-4-carboxylic acid (8-methoxy-5-phenyl-quinoxalin-2-yl)-amide |
| 78 | 1-(2-Methoxy-ethyl)-1H-[1,2,3]triazole-4-carboxylic acid (8-methoxy-5-phenyl-quinoxalin-2-yl)-amide |
| 79 | 5-Cyclopropyl-isoxazole-4-carboxylic acid (8-methoxy-5-phenyl-quinoxalin-2-yl)-amide |
| 80 | 5-Methyl-isoxazole-4-carboxylic acid (8-methoxy-5-phenyl-quinoxalin-2-yl)-amide |
| 81 | 1-Methyl-1H-pyrazole-4-carboxylic acid (8-methoxy-5-phenyl-quinoxalin-2-yl)-amide |
| 82 | 6-Oxo-1,6-dihydro-pyridazine-4-carboxylic acid (8-methoxy-5-phenyl-quinoxalin-2-yl)-amide |
| 83 | 4-Hydroxy-4-methyl-piperidine-1-carboxylic acid (5-butyl-8-methoxy-quinoxalin-2-yl)-amide |
| 84 | 4-Hydroxy-4-methyl-piperidine-1-carboxylic acid [8-methoxy-5-(1-propyl-cyclopropyl)-quinoxalin-2-yl]-amide |
| 85 | 4-Hydroxy-4-methyl-piperidine-1-carboxylic acid [8-methoxy-5-(1-methoxymethyl-cyclopropyl)-quinoxalin-2-yl]-amide |
| 86 | 4-Hydroxy-4-methyl-piperidine-1-carboxylic acid [5-(3-amino-phenyl)-8-methoxy-quinoxalin-2-yl]-amide |
| 87 | 4-Hydroxy-4-methyl-piperidine-1-carboxylic acid (8-methoxy-5-pyridin-2-yl-quinoxalin-2-yl)-amide |
| 88 | 4-Hydroxy-4-methyl-piperidine-1-carboxylic acid (8-methoxy-5-o-tolyl-quinoxalin-2-yl)-amide |
| 89 | 1-Cyano-cyclopropanecarboxylic acid (5-methoxy-8-phenyl-pyrido[3,4-b]pyrazin-3-yl)-amide |
| 90 | Cyclopropanecarboxylic acid (5-methoxy-8-phenyl-pyrido[3,4-b]pyrazin-3-yl)-amide |
| 91 | N-[8-methoxy-5-(oxan-4-yl)quinoxalin-2-yl]-2-oxa-7-azaspiro[4.4]nonane-7-carboxamide |
| 92 | 4-hydroxy-N-[8-methoxy-5-(pyridin-4-yl)quinoxalin-2-yl]-4-methylpiperidine-1-carboxamide |
| 93 | 3-hydroxy-N-[8-methoxy-5-(oxan-4-yl)quinoxalin-2-yl]-3-methylpyrrolidine-1-carboxamide |
| 94 | N-[8-methoxy-5-(oxan-4-yl)quinoxalin-2-yl]-2-methyl-1,3-oxazole-4-carboxamide |
| 95 | 4-(hydroxymethyl)-N-[8-methoxy-5-(oxan-4-yl)quinoxalin-2-yl]-4-methylpiperidine-1-carboxamide |
| 96 | N-[8-methoxy-5-(oxan-4-yl)quinoxalin-2-yl]-2,2-dioxo-2lambda6-thia-6-azaspiro[3.3]heptane-6-carboxamide |
| 97 | 6-methoxy-N-[8-methoxy-5-(oxan-4-yl)quinoxalin-2-yl]pyridazine-3-carboxamide |
| 98 | N-[8-methoxy-5-(oxan-4-yl)quinoxalin-2-yl]-1-(2-methoxyethyl)-1H-pyrazole-4-carboxamide |
| 99 | 4-hydroxy-N-(8-methoxy-5-phenylquinoxalin-2-yl)-4-(prop-2-yn-1-yl)piperidine-1-carboxamide |
| 100 | 3-hydroxy-N-(8-methoxy-5-phenylquinoxalin-2-yl)-3-methylpyrrolidine-1-carboxamide |
| 101 | 4-(hydroxymethyl)-N-(8-methoxy-5-phenylquinoxalin-2-yl)-4-methylpiperidine-1-carboxamide |
| 102 | N-(8-methoxy-5-phenylquinoxalin-2-yl)-8-oxa-2-azaspiro[4.5]decane-2-carboxamide |
| 103 | 4-Hydroxy-4-prop-2-ynyl-piperidine-1-carboxylic acid [5-methoxy-8-(tetrahydro-pyran-4-yl)-pyrido[3,4-b]pyrazin-3-yl]-amide |
| 104 | 4-Hydroxymethyl-4-methyl-piperidine-1-carboxylic acid [5-methoxy-8-(tetrahydro-pyran-4-yl)-pyrido[3,4-b]pyrazin-3-yl]-amide |
| 105 | N-(8-methoxy-5-phenylquinoxalin-2-yl)-2-methyl-1,3-oxazole-5-carboxamide |
| 106 | Cyclopropanecarboxylic acid [5-methoxy-8-(tetrahydro-pyran-4-yl)-pyrido[3,4-b]pyrazin-3-yl]-amide |
| 107 | N-(8-butyl-5-methoxyquinoxalin-2-yl)-4-hydroxy-4-methylpiperidine-1-carboxamide |
| 108 | N-(5-butyl-8-methoxyquinoxalin-2-yl)-4-hydroxy-4-methylpiperidine-1-carboxamide |
| 109 | N-[5-(3,6-dihydro-2H-pyran-4-yl)-8-methoxyquinoxalin-2-yl]-4-hydroxy-4-methylpiperidine-1-carboxamide |
| 110 | N-[8-(3-fluorophenyl)-5-methoxyquinoxalin-2-yl]-4-hydroxy-4-methylpiperidine-1-carboxamide |
| 111 | N-[8-(2-fluorophenyl)-5-methoxyquinoxalin-2-yl]-4-hydroxy-4-methylpiperidine-1-carboxamide |
| 112 | 4-hydroxy-N-[5-methoxy-8-(pyridin-3-yl)quinoxalin-2-yl]-4-methylpiperidine-1-carboxamide |
| 113 | 6-methoxy-N-(8-methoxy-5-phenylquinoxalin-2-yl)pyridazine-3-carboxamide |
| 114 | 4-hydroxy-N-(8-methoxy-5-{1-[(pyridin-2-yl)methyl]-1H-pyrazol-4-yl}quinoxalin-2-yl)-4-methylpiperidine-1-carboxamide |
| 115 | 4-{2-[(4-hydroxy-4-methylpiperidine-1-carbonyl)amino]-8-methoxyquinoxalin-5-yl}-N-methylpyridine-2-carboxamide |
| 116 | tert-butyl 3-(4-{2-[(4-hydroxy-4-methylpiperidine-1-carbonyl)amino]-8-methoxyquinoxalin-5-yl}-1H-pyrazol-1-yl)azetidine-1-carboxylate |

| No. | IUPAC-Name |
|---|---|
| 117 | 4-hydroxy-N-{8-methoxy-5-[3-(2-methoxyethoxy)phenyl]quinoxalin-2-yl}-4-methylpiperidine-1-carboxamide |
| 118 | 4-hydroxy-N-(8-methoxy-5-{3-[(2-methoxyethoxy)methyl]phenyl}quinoxalin-2-yl)-4-methylpiperidine-1-carboxamide |
| 119 | 4-hydroxy-N-(8-methoxy-5-{1-[2-(2-methoxyethoxy)ethyl]-1H-pyrazol-4-yl}quinoxalin-2-yl)-4-methylpiperidine-1-carboxamide |
| 120 | N-[5-(2-fluorophenyl)-8-methoxyquinoxalin-2-yl]cyclopropanecarboxamide |
| 121 | N-[8-methoxy-5-(pyridin-3-yl)quinoxalin-2-yl]cyclopropanecarboxamide |
| 122 | N-[5-(azepan-1-yl)-8-methoxyquinoxalin-2-yl]cyclopropanecarboxamide |
| 123 | N-[5-(2,3-difluorophenyl)-8-methoxyquinoxalin-2-yl]cyclopropanecarboxamide |
| 124 | N-[5-(2,5-difluorophenyl)-8-methoxyquinoxalin-2-yl]cyclopropanecarboxamide |
| 125 | N-[5-(2,3-difluorophenyl)-8-methoxyquinoxalin-2-yl]-2-methyl-1,3-oxazole-5-carboxamide |
| 126 | N-[5-(4-fluorophenyl)-8-methoxyquinoxalin-2-yl]cyclopropanecarboxamide |
| 127 | N-[8-methoxy-5-(1,2,3,6-tetrahydropyridin-4-yl)quinoxalin-2-yl]cyclopropanecarboxamide |
| 128 | N-[5-(2,5-difluorophenyl)-8-methoxyquinoxalin-2-yl]-2-methyl-1,3-oxazole-5-carboxamide |
| 129 | N-[5-(2-fluorophenyl)-8-methoxyquinoxalin-2-yl]-2-methyl-1,3-oxazole-5-carboxamide |
| 130 | N-[8-methoxy-5-(oxan-4-yl)quinoxalin-2-yl]-2-methyl-1,3-oxazole-5-carboxamide |
| 131 | N-[5-(4-fluorophenyl)-8-methoxyquinoxalin-2-yl]-2-methyl-1,3-oxazole-5-carboxamide |
| 132 | N-[5-(3,6-dihydro-2H-pyran-4-yl)-8-methoxyquinoxalin-2-yl]-2-methyl-1,3-oxazole-5-carboxamide |
| 133 | N-{5-[1-(azetidin-3-yl)-1H-pyrazol-4-yl]-8-methoxyquinoxalin-2-yl}-4-hydroxy-4-methylpiperidine-1-carboxamide |
| 134 | N-[5-(3,6-dihydro-2H-pyran-4-yl)-8-methoxyquinoxalin-2-yl]-2-methyl-1,3-thiazole-5-carboxamide |
| 135 | N-[5-(3,6-dihydro-2H-pyran-4-yl)-8-methoxyquinoxalin-2-yl]-1-methyl-1H-pyrazole-4-carboxamide |
| 136 | N-[5-(3,6-dihydro-2H-pyran-4-yl)-8-methoxyquinoxalin-2-yl]-1,2-thiazole-4-carboxamide |
| 137 | 1-amino-N-[5-(3,6-dihydro-2H-pyran-4-yl)-8-methoxyquinoxalin-2-yl]cyclopropane-1-carboxamide |
| 138 | N-[8-methoxy-5-(pyridin-3-yl)quinoxalin-2-yl]-2-methyl-1,3-oxazole-5-carboxamide |
| 139 | 2-amino-N-[5-(3,6-dihydro-2H-pyran-4-yl)-8-methoxyquinoxalin-2-yl]-1,3-thiazole-4-carboxamide |
| 140 | N-[5-(3,6-dihydro-2H-pyran-4-yl)-8-methoxyquinoxalin-2-yl]-5-(oxolan-3-yl)-1,3-thiazole-2-carboxamide |
| 141 | N-[5-(2,5-dihydrofuran-3-yl)-8-methoxyquinoxalin-2-yl]cyclopropanecarboxamide |
| 142 | 5-(aminomethyl)-N-[5-(3,6-dihydro-2H-pyran-4-yl)-8-methoxyquinoxalin-2-yl]furan-3-carboxamide |
| 143 | ethyl 5-({[5-(3,6-dihydro-2H-pyran-4-yl)-8-methoxyquinoxalin-2-yl]carbamoyl}amino)-1,3,4-thiadiazole-2-carboxylate |
| 144 | N'1-[5-(3,6-dihydro-2H-pyran-4-yl)-8-methoxyquinoxalin-2-yl]-N1,N1-dimethylcyclopropane-1,1-dicarboxamide |
| 145 | N-[5-(3,6-dihydro-2H-pyran-4-yl)-8-methoxyquinoxalin-2-yl]-1-[(dimethylamino)methyl]cyclopropane-1-carboxamide |
| 146 | N-[5-(3,6-dihydro-2H-pyran-4-yl)-8-methoxyquinoxalin-2-yl]-5-methyl-1,3,4-thiadiazole-2-carboxamide |
| 147 | N-{8-methoxy-5-[3-(2-methoxyethoxy)phenyl]quinoxalin-2-yl}cyclopropanecarboxamide |
| 148 | N-{8-methoxy-5-[3-(2-methoxyethoxy)phenyl]quinoxalin-2-yl}-2-methyl-1,3-oxazole-5-carboxamide |
| 149 | N'1-(8-methoxy-5-phenylquinoxalin-2-yl)-N1,N1-dimethylcyclopropane-1,1-dicarboxamide |
| 150 | 1-[(dimethylamino)methyl]-N-(8-methoxy-5-phenylquinoxalin-2-yl)cyclopropane-1-carboxamide |
| 151 | N-{8-methoxy-5-[3-(2-methoxyethoxy)phenyl]quinoxalin-2-yl}-2-methyl-1,3-thiazole-5-carboxamide |
| 152 | N-{8-methoxy-5-[3-(2-methoxyethoxy)phenyl]quinoxalin-2-yl}-5-methyl-1,3,4-thiadiazole-2-carboxamide |
| 153 | 4-hydroxy-N-{8-methoxy-5-[1-(pyridin-2-yl)-1H-pyrazol-4-yl]quinoxalin-2-yl}-4-methylpiperidine-1-carboxamide |
| 154 | N-[8-methoxy-5-(6-methylpyridazin-3-yl)quinoxalin-2-yl]-2-methyl-1,3-oxazole-5-carboxamide |
| 155 | N-[8-methoxy-5-(2-methoxypyrimidin-5-yl)quinoxalin-2-yl]-2-methyl-1,3-oxazole-5-carboxamide |
| 156 | N-[8-methoxy-5-(2-methoxypyrimidin-5-yl)quinoxalin-2-yl]cyclopropanecarboxamide |
| 157 | N-{5-[1-(difluoromethyl)-1H-pyrazol-4-yl]-8-methoxyquinoxalin-2-yl}-2-methyl-1,3-oxazole-5-carboxamide |
| 158 | N-{5-[1-(difluoromethyl)-1H-pyrazol-4-yl]-8-methoxyquinoxalin-2-yl}-4-hydroxy-4-methylpiperidine-1-carboxamide |
| 159 | N-[5-(3,6-dihydro-2H-pyran-4-yl)-8-methoxyquinoxalin-2-yl]-1H-imidazole-5-carboxamide |
| 160 | N-(8-methoxy-5-phenylquinoxalin-2-yl)-1H-imidazole-5-carboxamide |
| 161 | N-[8-methoxy-5-(1,4-oxazepan-4-yl)quinoxalin-2-yl]cyclopropanecarboxamide | and physiologically acceptable salts, derivatives, solvates, prodrugs and stereoisomers thereof, including mixtures thereof in all ratios.

All above-mentioned preferred, particularly preferred and very particularly preferred meanings of the above radicals of the compounds of the formula I should be understood in such a way that these preferred particularly preferred and very particularly preferred meanings or embodiments can be combined with one another in any possible combination to give compounds of the formula I and preferred, particularly preferred and very particularly preferred compounds of the formula I of this type are likewise explicitly disclosed hereby.

Hal denotes fluorine, chlorine, bromine or iodine, in particular fluorine, bromine or chlorine.

—(C=O)— or =O denotes carbonyl oxygen and stands for

or oxygen atom bonded to a carbon atom by means of a double bond.

Alkyl is a saturated unbranched (linear) or branched hydrocarbon chain and has 1, 2, 3, 4, 5, 6, 7, 8, 9 or 10 C atoms. Alkyl preferably denotes alkenyl methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, linear or branched heptyl, octyl, nonyl or decyl, further preferably, for example, trifluoromethyl.

Cyclic alkyl or cycloalkyl is a saturated cyclic hydrocarbon chain and has 3-10, preferably 3-7 C atoms and preferably denotes cyclopropyl, cyclobutyl, cyclopentyl, cyclohexyl or cycloheptyl. Cycloalkyl also denotes a partially unsaturated cyclic alkyl, such as, for example, cyclohexenyl or cyclohexynyl.

Alkenyl denotes an unsaturated unbranched (linear) or branched hydrocarbon chain and has 1, 2, 3, 4, 5, 6, 7, 8, 9 or 10 C atoms.

O-alkyl or OA denotes linear or branched alkoxyl having 1-6 C atoms, and is preferably methoxyl, furthermore also e.g. ethoxyl, n-propoxyl, isopropoxyl, n-butoxyl, isobutoxyl, sec-butoxyl or tert-butoxyl.

Alkyloxycarbonyl refers to straight or branched chain esters of a carboxylic acid derivative of the present invention, i.e. methyloxycarbonyl (MeOCO—), ethyloxycarbonyl, or butyloxycarbonyl.

Alkylcarbonyl refers to straight or branched chain alkyl and a carboxylic acid group.

Aryl, Ar or aromatic ring denotes a mono- or polycyclic aromatic or fully unsaturated cyclic hydrocarbon chain, for example unsubstituted phenyl, naphthyl or biphenyl, furthermore preferably phenyl, naphthyl or biphenyl, each of which is mono-, di- or trisubstituted, for example, by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl.

Heterocycle and heterocyclyl refer to saturated or unsaturated non-aromatic rings or ring systems containing at least one heteroatom selected from O. S and N. further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

Heteroaryl means an aromatic or partially aromatic heterocycle that contains at least one ring heteroatom selected from O. S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoxazolyl, isoindolyl, dihydrobenzothienyl, indolizinyl, cinnolinyl, phthalazinyl, quinazolinyl, naphthyridinyl, carbazolyl, benzodioxinyl, benzodioxolyl, quinoxalinyl, purinyl, furazanyl, thiophenyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

Mono- or bicyclic saturated, unsaturated or aromatic heterocycle preferably denotes unsubstituted or mono-, di- or trisubstituted 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated and also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Heterocycle furthermore denotes, for example, 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-hydroxy-6-oxopiperazin-1-yl, 2-methoxy-6-oxopiperazin-1-yl or 2-azabicyclo[2.2.2]octan-3-on-2-yl.

Heterocycloalkyl here denotes a fully hydrogenated or saturated heterocycle, heterocycloalkenyl (one or more double bonds) or heterocycloalkynyl (one or more triple bonds) denotes a partially or incompletely hydrogenated or unsaturated heterocycle, heteroaryl denotes an aromatic or fully unsaturated heterocycle.

A cyclic alkylaryl group in connection with the present invention means that and one or two aromatic rings Ar are condensed onto an unsubstituted or a mono- or disubstituted cyclic alkyl, in which one or two $CH_2$ groups and/or, in addition, 1-11 H atoms may be replaced, such as, for example, in the radicals depicted below:

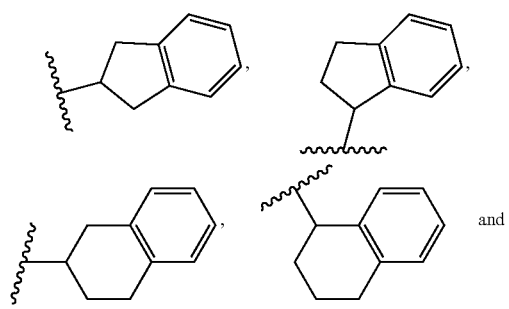

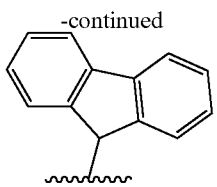

Furthermore, the abbreviations below have the following meanings:
Boc ter-butoxycarbonyl
CBZ benzyloxycarbonyl
DNP 2,4-dinitrophenyl
FMOC 9-fluorenylmethoxycarbonyl
imi-DNP 2,4-dinitrophenyl in the 1-position of the imidazole ring
OMe methyl ester
POA phenoxyacetyl
DCCI dicyclohexylcarbodiimide
HOBt 1-hydroxybenzotriazole The invention therefore relates to a pharmaceutical preparation comprising the compound according to the present invention and/or one of its physiologically acceptable salts, derivatives, solvates, prodrugs and stereoisomers, including mixtures thereof in all ratios.

The invention also relates to a pharmaceutical preparation according to the invention of this type, comprising further excipients and/or adjuvants.

In addition, the invention relates to an above pharmaceutical preparation according to the invention, comprising at least one further medicament active compound.

Pharmaceutically or physiologically acceptable derivatives are taken to mean, for example, salts of the compound of the present invention, and also so-called prodrug compounds. Prodrug compounds are taken to mean derivatives the compound of the present invention which have been modified by means of, for example, alkyl or acyl groups (see also amino- and hydroxyl-protecting groups below), sugars or oligopeptides and which are rapidly cleaved or liberated in the organism to form the effective molecules. These also include biodegradable polymer derivatives of the compound of the present invention, as described, for example, in Int. J. Pharm. 115 (1995), 61-67.

The compound of the present invention can be used in its final non-salt form. On the other hand, the present invention also encompasses the use of pepstatin in the form of its pharmaceutically acceptable salts, which can be derived from various organic and inorganic bases by procedures known in the art. Pharmaceutically acceptable salt forms of pepstatin are for the most part prepared by conventional methods. If the compound of the present invention contains a carboxyl group, one of its suitable salts can be formed by reacting the compound of the present invention with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of pepstatin are likewise included.

Furthermore, the base salts of the compound of the present invention include aluminium, ammonium, calcium, copper, iron(III), iron(II), lithium, magnesium, manganese (III), manganese(II), potassium, sodium and zinc salts, but this is not intended to represent a restriction.

Of the above-mentioned salts, preference is given to ammonium; the alkali metal salts sodium and potassium, and the alkaline-earth metal salts calcium and magnesium. Salts of the compound of the present invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

As mentioned, the pharmaceutically acceptable base-addition salts of pepstatin are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of the compound of the present invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

In view of that stated above, it can be seen that the term "pharmaceutically acceptable salt" in the present connection is taken to mean an active compound which comprises the compound of the present invention in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

Solvates of the compound of the present invention are taken to mean adductions of inert solvent molecules pepstatin which form owing to their mutual attractive force. Solvates are, for example, hydrates, such as monohydrates or dihydrates, or alcoholates, i.e. addition compounds with alcohols, such as, for example, with methanol or ethanol.

All physiologically acceptable salts, derivatives, solvates and stereoisomers of these compounds, including mixtures thereof in all ratios, are also in accordance with the invention.

Compounds of the general formula I may contain one or more centres of chirality, so that all stereoisomers, enantiomers, diastereomers, etc., of the compounds of the general formula I are also claimed in the present invention.

The invention also relates to the optically active forms (stereoisomers), the enantiomers, the racemates, the diastereomers and hydrates and solvates of these compounds.

Compounds of the formula I according to the invention may be chiral owing to their molecular structure and may accordingly occur in various enantiomeric forms. They may therefore be in racemic or optically active form. Since the pharmaceutical efficacy of the racemates or stereoisomers of the compounds according to the invention may differ, it may be desirable to use the enantiomers. In these cases, the end product, but also even the intermediates, may be separated into enantiomeric compounds by chemical or physical measures known to the person skilled in the art or already employed as such in the synthesis.

Pharmaceutically or physiologically acceptable derivatives are taken to mean, for example, salts of the compounds according to the invention and also so-called prodrug compounds. Prodrug compounds are taken to mean compounds of the formula I which have been modified with, for example, alkyl or acyl groups (see also amino- and hydroxyl-protecting groups below), sugars or oligopeptides and which are rapidly cleaved or liberated in the organism to form the effective compounds according to the invention. These also include biodegradable polymer derivatives of the compounds according to the invention, as described, for example, in Int. J. Pharm. 115 (1995), 61-67.

Suitable acid-addition salts are inorganic or organic salts of all physiologically or pharmacologically acceptable acids, for example halides, in particular hydrochlorides or hydrobromides, lactates, sulfates, citrates, tartrates, maleates, fumarates, oxalates, acetates, phosphates, methylsulfonates or p-toluenesulfonates.

Very particular preference is given to the hydrochlorides, the trifluoroacetates or the bistrifluoroacetates of the compounds according to the invention.

Solvates of the compounds of the formula I are taken to mean adductions of inert solvent molecules onto the compounds of the formula I which form owing to their mutual attractive force. Solvates are, for example, hydrates, such as monohydrates or dihydrates, or alcoholates, i.e. addition compounds with alcohols, such as, for example, with methanol or ethanol.

It is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to their simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant with a readily available isotope-labelled reactant.

In order to manipulate the oxidative metabolism of the compound by way of the primary kinetic isotope effect, deuterium ($^2H$) can also be incorporated into a compound of the formula I. The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D=2-7$ are typical. If this rate difference is successfully applied to a compound of the formula I that is susceptible to oxidation, the profile of this compound in vivo can thereby be drastically modified and result in improved pharmacokinetic properties.

When discovering and developing therapeutic agents, the person skilled in the art attempts to optimise pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of the compounds of the formula I are thereby obtained and can be expressed quantitatively in terms of increases in the in-vivo half-life (T/2), concentration at maximum therapeutic effect ($C_{max}$), area under the dose response curve (AUC), and F; and in terms of reduced clearance, dose and costs of materials.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

The replacement of hydrogen by deuterium in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al., Biochemistry 33(10), 2927-2937, 1994, and Jarman et al., Carcinogenesis 16(4), 683-688, 1993.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of two stereoisomeric compounds. However, preference is also given to mixtures of two or more compounds of the formula I.

In addition, the invention relates to a process for the preparation of the compounds of the formula I, characterized in that

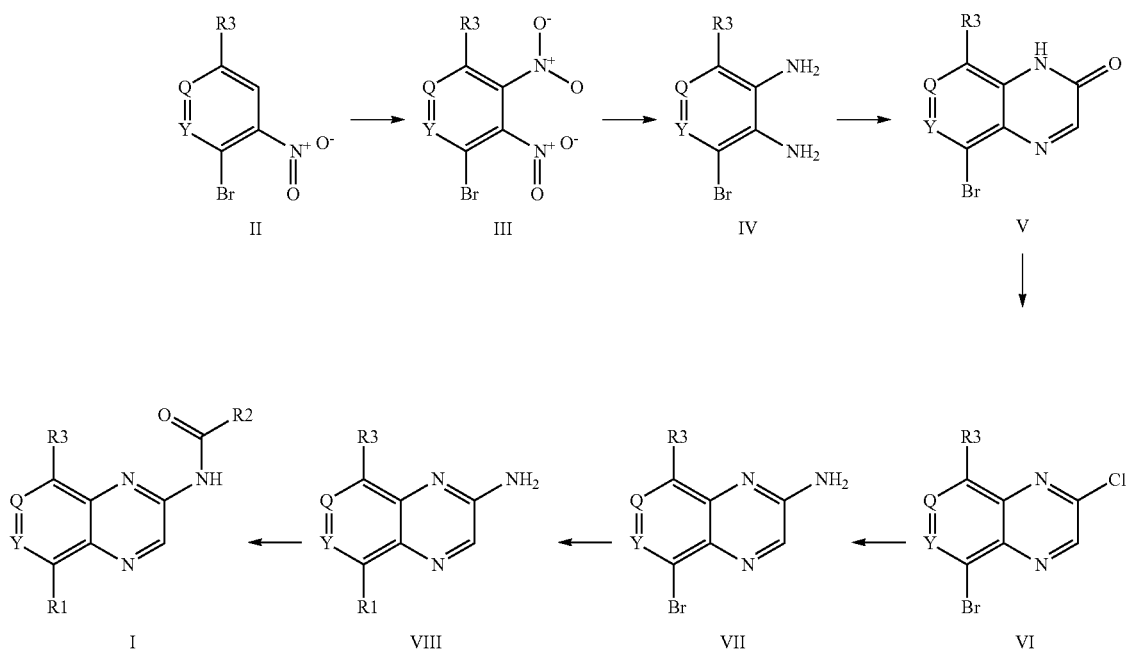

a) a compound of the formula II undergoes a nitration reaction, followed by a reduction to give a compound of formula IV, a compound of formula IV is cyclized to give a compound of formula V, a compound of formula V is chlorinated followed by a copper catalyzed amination reaction to give compound VII, a compound of formula VII is reacted in a Suzuki type reaction to a compound of formula VIII employing the use of catalyst and base, a compound of formula VIII is converted to a compound of the formula I by standard amidation or carbamide formation conditions wherein Q, Y, $R^1$, $R^2$ and $R^3$ have the meanings as disclosed above,

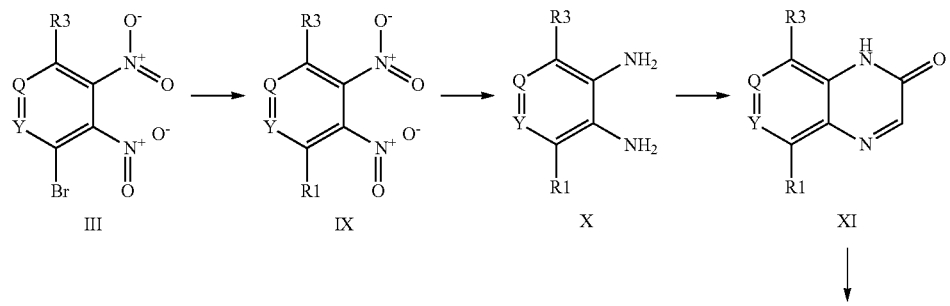

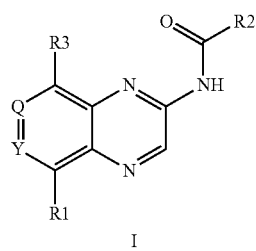
I

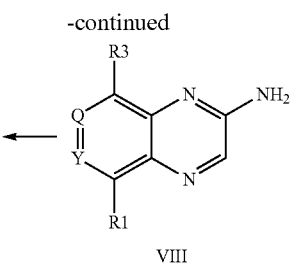
VIII

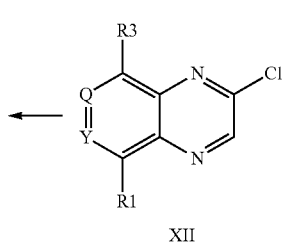
XII b) a compound of the formula III is reacted with a boronic ester or acid under Suzuki-type reaction conditions to give a compound of the formula IX or reacted with an amine in a nucleophilic substitution reaction under increased temperature to form a compound of the formula IX, a compound of formula IX is reduced to a compound of the formula X and cyclized to a compound of the formula XI, a compound of formula XI is chlorinated followed by copper catalyzed amination to give compound VIII and finally compound VIII is reacted to a compound of the formula I under standard amidation or carbamide formation conditions and wherein Q, Y, $R^1$, $R^2$ and $R^3$ have the meanings as disclosed above, It is also possible to carry out the reactions stepwise in each case and to modify the sequence of the linking reactions of the building blocks with adaptation of the protecting-group concept.

The starting materials or starting compounds are generally known. If they are novel, they can be prepared by methods known per se.

If desired, the starting materials can also be formed in situ by not isolating them from the reaction mixture, but instead immediately converting them further into the compounds of the formula I.

The compounds of the formula I are preferably obtained by liberating them from their functional derivatives by

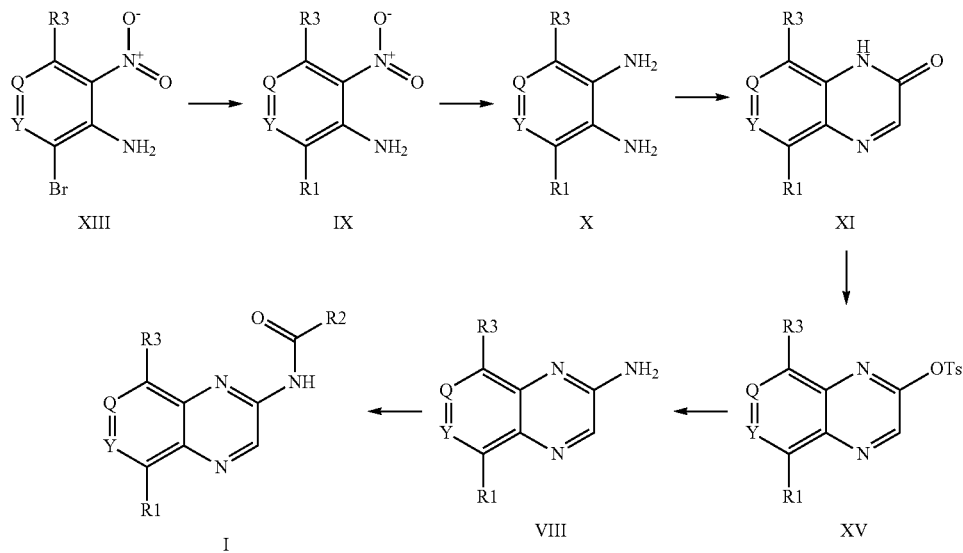

c) a compound of the formula XIII is reacted with a boronic ester or acid under Suzuki-type reaction conditions to give a compound of the formula XIV, a compound of formula XIV is reduced to a compound of the formula X and cyclized to a compound of the formula XI, a compound of formula XI is tosylated followed by metal catalyzed amination to give compound VIII and finally compound VIII is reacted to a compound of the formula I under standard amidation or carbamide formation conditions and wherein Q, Y, $R^1$, $R^2$ and $R^3$ have the meanings as disclosed above, d) the base of a compound of the formula I is converted into one of its salts by treatment with an acid, or e) an acid of a compound of the formula I is converted into one of its salts by treatment with a base.

solvolysis, in particular by hydrolysis, or by hydrogenolysis. Preferred starting materials for the solvolysis or hydrogenolysis are those which contain correspondingly protected amino, carboxyl and/or hydroxyl groups instead of one or more free amino, carboxyl and/or hydroxyl groups, preferably those which carry an amino-protecting group instead of an H atom which is connected to an N atom. Preference is furthermore given to starting materials which carry a hydroxyl-protecting group instead of the H atom of a hydroxyl group. Preference is also given to starting materials which carry a protected carboxyl group instead of a free carboxyl group. It is also possible for a plurality of identical or different protected amino, carboxyl and/or hydroxyl groups to be present in the molecule of the starting material. If the protecting groups present are different from one another, they can in many cases be cleaved off selectively.

The term "amino-protecting group" is generally known and relates to groups which are suitable for protecting (blocking) an amino group against chemical reactions, but which can easily be removed after the desired chemical reaction has been carried out elsewhere in the molecule. Typical of such groups are, in particular, unsubstituted or substituted acyl groups, furthermore unsubstituted or substituted aryl (for example 2,4-dinitrophenyl) or aralkyl groups (for example benzyl, 4-nitrobenzyl, triphenylmethyl). Since the amino-protecting groups are removed after the desired reaction or reaction sequence, their type and size is, in addition, not crucial, but preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of such acyl groups are alkanoyl, such as acetyl, propionyl, buturyl, aralkanoyl, such as phenylacetyl, aroyl, such as benzoyl or toluyl, aryoxyaklkanoyl, such as phenoxyacetyl, alkoxycarbonyl, such as methoxycarbonyl, ethoxycarbonyl, 2,2,2-trichloroethoxycarbonyl, BOC, 2-iodoethoxycaronyl, aralkoxycarbonyl. such as CBZ, 4-methoxybenzyloxycarbonyl or FMOC. Preferred acyl groups are CBZ, FMOC, benzyl and acetyl.

The term "acid-protecting group" or "carboxyl-protecting group" is likewise generally known and relates to groups which are suitable for protecting a —COOH group against chemical reactions, but which can easily be removed after the desired chemical reaction has been carried out elsewhere in the molecule. The use of esters instead of the free acids, for example of substituted and unsubstituted alkyl esters (such as methyl, ethyl, tert-butyl and substituted derivatives thereof), of substituted and unsubstituted benzyl esters or silyl esters, is typical. The type and size of the acid-protecting groups is not crucial, but preference is given to those having 1-20, in particular 1-10, C atoms.

The term "hydroxyl-protecting group" is likewise generally known and relates to groups which are suitable for protecting a hydroxyl group against chemical reactions, but which can easily be removed after the desired chemical reaction has been carried out elsewhere in the molecule. Typical of such groups are the above-mentioned unsubstituted or substituted aryl, aralkyl or acyl groups, furthermore also alkyl groups. Their type and size of the hydroxyl-protecting groups is not crucial, but preference is given to those having 1-20, in particular 1-10, C atoms. Examples of hydroxyl-protecting groups are, inter alia, benzyl, p-nitrobenzoyl, p-toluenesulfonyl and acetyl, where benzyl and acetyl are preferred.

Further typical examples of amino-, acid- and hydroxyl-protecting groups are found, for example, in "Greene's Protective Groups in Organic Synthesis", fourth edition, Wiley-Interscience, 2007.

The functional derivatives of the compounds of the formula I to be used as starting materials can be prepared by known methods of amino-acid and peptide synthesis, as described, for example, in the said standard works and patent applications.

The compounds of the formula I are liberated from their functional derivatives, depending on the protecting group used, for example, with the aid of strong acids, advantageously using trifluoroacetic acid or perchloric acid, but also using other strong inorganic acids, such as hydrochloric acid or sulfuric acid, strong organic acids, such as trichloroacetic acid, or sulfonic acids, such as benzoyl- or p-toluenesulfonic acid. The presence of an additional inert solvent and/or a catalyst is possible, but is not always necessary.

Depending on the respective synthetic route, the starting materials can optionally be reacted in the presence of an inert solvent.

Suitable inert solvents are, for example, heptane, hexane, petroleum ether, DMSO, benzene, toluene, xylene, trichloroethylene-, 1,2-dichloroethanecarbon tetrachloride, chloroform or dichloromethane; alcohols, such as methanol, ethanol, isopropanol, n-propanol, n-butanol or tert-butanol; ethers, such as diethyl ether, diisopropyl ether (preferably for substitution on the indole nitrogen), tetrahydrofuran (THF) or dioxane; glycol ethers, such as ethylene glycol monomethyl or monoethyl ether, ethylene glycol dimethy-l ether (diglyme); ketones, such as acetone or butanone; amides, such as acetamide, dimethylacetamide, N-methylpyrrolidone (NMP) or dimethylformamide (DMF); nitriles, such as acetonitrile; esters, such as ethyl acetate, carboxylic acids or acid anhydrides, such as, for example, such as acetic acid or acetic anhydride, nitro compounds, such as nitromethane or nitrobenzene, optionally also mixtures of the said solvents with one another or mixtures with water.

The amount of solvent is not crucial; 10 g to 500 g of solvent can preferably be added per g of the compound of the formula I to be reacted.

It may be advantageous to add an acid-binding agent, for example an alkali metal or alkaline-earth metal hydroxide, carbonate or bicarbonate or other alkali or alkaline-earth metal salts of weak acids, preferably a potassium, sodium or calcium salt, or to add an organic base, such as, for example, on triethylamine, dimethylamine, pyridine or quinoline, or an excess of the amine component.

The resultant compounds according to the invention can be separated from the corresponding solution in which they are prepared (for example by centrifugation and washing) and can be stored in another composition after separation, or they can remain directly in the preparation solution. The resultant compounds according to the invention can also be taken up in desired solvents for the particular use.

The reaction duration depends on the reaction conditions selected. In general, the reaction duration is 0.5 hour to 10 days, preferably 1 to 24 hours. On use of a microwave, the reaction time can be reduced to values of 1 to 60 minutes.

The compounds of the formula I and also the starting materials for their preparation are, in addition, prepared by known methods, as described in the literature (for example in standard works, such as Houben-Weyl, Methoden der organischen Chemie [Methods of Organic Chemistry], Georg-Thieme-Verlag, Stuttgart), for example under reaction conditions which are known and suitable for the said reactions. Use can also be made here of variants known per se, which are not described here in greater detail.

Conventional work-up steps, such as, for example, addition of water to the reaction mixture and extraction, enable the compounds to be obtained after removal of the solvent. It may be advantageous, for further purification of the product, to follow this with a distillation or crystallisation or to carry out a chromatographic purification.

An acid of the formula I can be converted into the associated addition salt using a base, for example by reaction of equivalent amounts of the acid and base in an inert solvent, such as ethanol, and inclusive evaporation. Suitable bases for this reaction are, in particular, those which give physiologically acceptable salts. Thus, the acid of the formula I can be converted into the corresponding metal salt, in particular alkali or alkaline-earth metal salt, using a base (for example sodium hydroxide, potassium hydroxide, sodium carbonate or potassium carbonate) or into the corresponding ammonium salt. Organic bases which give physiologically acceptable salts, such as, for example, ethanolamine, are also suitable for this reaction.

On the other hand, a base of the formula I can be converted into the associated acid-addition salt using an acid, for example by reaction of equivalent amounts of the base and acid in an inert solvent, such as ethanol, with subsequent evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic, mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxysulfonic acid, benzenesulfonic acid, p-toluenesulfonic acid, naphthalenemom- and disulfonic acids or laurylsulfuric acid. Salts with physiologically unacceptable acids, for example picrates, can be used for the isolation and/or purification of the compounds of the formula I.

It has been found that the compounds of the formula I are well tolerated and have valuable pharmacological properties.

Since adenosine receptors, such as $A_{2A}$ and $A_{2B}$, are shown to down-regulate the immune response during inflammation and protect tissues from immune damage, inhibition of signaling through adenosine receptors can be used to intensify and prolong the immune response.

Methods are provided herein to increase an immune response. In one example, the method increases desirable and targeted tissue damage, such as damage of a tumor, for example cancer. Disclosed herein are methods of inhibiting one or more processes conducive to the production of extracellular adenosine and adenosine-triggered signaling through adenosine receptors. For example, enhancement of an immune response, local tissue inflammation, and targeted tissue destruction is accomplished by: inhibiting or reducing the adenosine-producing local tissue hypoxia; by degrading (or rendering inactive) accumulated extracellular adenosine; by preventing or decreasing expression of adenosine receptors on immune cells; and or by inhibiting/antagonizing signaling by adenosine ligands through adenosine receptors. The results disclosed herein demonstrate that by in vivo administration of agents that disrupt the "hypoxia→adenosine accumulation→immunosuppressive adenosine receptor signaling to immune cells" pathway in subjects suffering from various diseases (e.g. cancer and sepsis) can result in in vivo treatment of tumors or improved immunization.

In one example, the method includes administering one or more inhibitors of extracellular adenosine and or adenosine receptor inhibitors, such as an adenosine receptor antagonist. To increase the efficacy of a vaccine, one or more adenosine receptor inhibitors and/or inhibitors of extracellular adenosine can be administered in conjunction with the vaccine. In one example, one or more adenosine receptor inhibitors or inhibitors of extracellular adenosine are administered to increase an immune response/inflammation. In another example, a method is provided to achieve targeted tissue damage, such as for tumor destruction.

The invention therefore furthermore relates to the use of compounds according to the invention for the preparation of a medicament for the treatment and/or prophylaxis of diseases which are caused, promoted and/or propagated by adenosine or other $A_{2A}$ and/or $A_{2B}$ receptor agonists.

The invention thus also relates, in particular, to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states.

Particular preference is given, in particular, to physiological and/or pathophysiological states which are connected to adenosine $A_{2A}$ and/or $A_{2B}$ receptors.

Physiological and/or pathophysiological states are taken to mean physiological and/or pathophysiological states which are medically relevant, such as, for example, diseases or illnesses and medical disorders, complaints, symptoms or complications and the like, in particular diseases.

The invention furthermore relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of hyperproliferative and infectious diseases and disorders.

The invention further relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of hyperproliferative and infectious diseases and disorders, wherein the hyperproliferative disease or disorder is cancer.

The invention thus particularly preferably relates to a medicament comprising at least one compound according to the invention and/or one of its physiologically acceptable salts, derivatives, solvates, prodrugs and stereoisomers, including mixtures thereof in all ratios, wherein the cancer is selected from the group consisting of acute and chronic lymphocytic leukemia, acute granulocytic leukemia, adrenal cortex cancer, bladder cancer, brain cancer, breast cancer, cervical cancer, cervical hyperplasia, cervical cancer, chorio cancer, chronic granulocytic leukemia, chronic lymphocytic leukemia, colon cancer, endometrial cancer, esophageal cancer, essential thrombocytosis, genitourinary carcinoma, glioma, glioblastoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell cancer, rhabdomyosarcoma, skin cancer, small-cell lung cancer, soft-tissue sarcoma, squamous cell cancer, stomach cancer, testicular cancer, thyroid cancer and Wilms' tumor.

The invention further preferably relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of hyperproliferative and infectious diseases and disorders, wherein the hyperproliferative disease or disorder is selected from the group consisting of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation and an immunoproliferative disease or disorder selected from the group consisting of inflammatory bowel disease, psoriasis, rheumatoid arthritis, systemic lupus erythematosus (SLE), vascular hyperproliferation secondary to retinal hypoxia and vasculitis.

The invention further preferably relates to a medicament comprising at least one compound according to the invention and/or one of its physiologically acceptable salts, derivatives, solvates, prodrugs and stereoisomers, including mixtures thereof in all ratios, for use in the treatment and/or prophylaxis of physiological and/or pathophysiological states selected from the group consisting of hyperproliferative and infectious diseases and disorders, wherein the infectious disease or disorder is selected from the group consisting of a) virally induced infectious diseases which are caused by retroviruses, hepadnaviruses, herpesviruses, flaviviridae and/or adenoviruses wherein the retroviruses are selected from lentiviruses or oncoretroviruses, wherein the lentivirus is selected from the group consisting of HIV-1, HIV-2, FIV, BIV, SIVs, SHIV, CAEV, VMV and EIAV and the oncoretrovirus is selected from the group consisting of HTLV-I, HTLV-II and BLV, the hepadnavirus is selected from the group consisting of HBV, GSHV and WHV, the herpesivirus is selected from the group from the group consisting of HSV I, HSV II, EBV, VZV, HCMV or HHV 8 and the flaviviridae is selected from the group consisting of HCV, West nile and Yellow Fever, b) bacterial infectious diseases which are caused by Gram-positive bacteria wherein the Gram-positive bacteria are selected from the group consisting of methicillin-susceptible and methicillin-resistant staphylococci (including *Staphylococcus aureus, Staphylococcus epidermidis, Staphylococcus haemolyticus, Staphylococcus hominis, Staphylococcus saprophyticus*, and coagulase-negative staphylococci), glycopeptides-intermediate susceptible *Staphylococcus aureus* (GISA), penicillin-susceptible and penicillin-resistant streptococci (including *Streptococcus pneumoniae, Streptococcus pyogenes, Streptococcus agalactiae, Streptococcus avium, Streptococcus bovis, Streptococcus lactis, Streptococcus sanguis* and Streptococci Group C (GCS), Streptococci Group G (GGS) and viridans streptococci), enterococci (including vancomycin susceptible and vancomycin-resistant strains such as *Enterococcus faecalis* and *Enterococcus faecium*), *Clostridium difficile, Listeria monocytogenes, Corynebacterium jeikeium, Chlamydia* spp (including *C. pneumoniae*) and *Mycobacterium tuberculosis,* c) bacterial infectious diseases which are caused by Gram-negative bacteria wherein the Gram-negative bacteria are selected from the group consisting of the Genus Enterobacteriacae, including *Escherichia* spp. (including *Escherichia coli*), *Klebsiella* spp., *Enterobacter* spp., *Citrobacter* spp., *Serratia* spp., *Proteus* spp., *Providencia* spp., *Salmonella* spp., *Shigella* spp., the genus *Pseudomonas* (including *P. aeruginosa*), *Moraxella* spp. (including *M. catarrhalis*), *Haemophilus* spp. and *Neisseria* spp., d) infectious diseases induced by intracellular active parasites selected from the group consisting of phylum Apicomplexa, or Sarcomastigophora (including *Trypanosoma, Plasmodia, Leishmania, Babesia* or *Theileria*), Cryptosporidia, Sacrocystida, Amoebia, Coccidia and Trichomonadia.

It is intended that the medicaments disclosed above include a corresponding use of the compounds according to the invention for the preparation of a medicament for the treatment and/or prophylaxis of the above physiological and/or pathophysiological states.

It is additionally intended that the medicaments disclosed above include a corresponding method for the treatment and/or prophylaxis of the above physiological and/or pathophysiological states in which at least one compound according to the invention is administered to a patient in need of such a treatment.

The compounds according to the invention preferably exhibit an advantageous biological activity which can easily be demonstrated in enzyme assays and animal experiments, as described in the examples. In such enzyme-based assays, the compounds according to the invention preferably exhibit and cause an inhibiting effect, which is usually documented by 1050 values in a suitable range, preferably in the micromolar range and more preferably in the nanomolar range.

The compounds according to the invention can be administered to humans or animals, in particular mammals, such as apes, dogs, cats, rats or mice, and can be used in the therapeutic treatment of the human or animal body and in the combating of the above-mentioned diseases. They can furthermore be used as diagnostic agents or as reagents.

Furthermore, compounds according to the invention can be used for the isolation and investigation of the activity or expression of adenosine $A_{2A}$ and/or $A_{2B}$ receptors. In addition, they are particularly suitable for use in diagnostic methods for diseases in connection with disturbed adenosine $A_{2A}$ and/or $A_{2B}$ receptor activity. The invention therefore furthermore relates to the use of the compounds according to the invention for the isolation and investigation of the activity or expression of adenosine $A_{2A}$ and/or $A_{2B}$ receptors or as binders and inhibitors of adenosine $A_{2A}$ and/or $A_{2B}$ receptors.

For diagnostic purposes, the compounds according to the invention can, for example, be radioactively labelled. Examples of radioactive labels are $^{3}H$, $^{14}C$, $^{231}I$ and $^{125}I$. A preferred labelling method is the iodogen method (Fraker et al., 1978). In addition, the compounds according to the invention can be labelled by enzymes, fluorophores and chemophores. Examples of enzymes are alkaline phosphatase, β-galactosidase and glucose oxidase, an example of a fluorophore is fluorescein, an example of a chemophore is luminol, and automated detection systems, for example for fluorescent colorations, are described, for example, in U.S. Pat. Nos. 4,125,828 and 4,207,554.

The present invention further relates to pharmaceutical compositions containing the compounds of the present invention and their use for the treatment and/or prophylaxis of diseases and disorders where the partial or total inactivation of adenosine $A_{2A}$ and/or $A_{2B}$ receptors could be beneficial.

The compounds of the formula I can be used for the preparation of pharmaceutical preparations, in particular by non-chemical methods. In this case, they are brought into a suitable dosage form together with at least one solid, liquid and/or semi-liquid excipient or adjuvant and optionally in combination with one or more further active compound(s).

The invention therefore furthermore relates to pharmaceutical preparations comprising at least one compound of the formula I and/or physiologically acceptable salts, derivatives, solvates and stereoisomers thereof, including mixtures thereof in all ratios. In particular, the invention also relates to pharmaceutical preparations which comprise further excipients and/or adjuvants, and also to pharmaceutical preparations which comprise at least one further medicament active compound.

In particular, the invention also relates to a process for the preparation of a pharmaceutical preparation, characterised in that a compound of the formula I and/or one of its physiologically acceptable salts, derivatives, solvates and stereoisomers, including mixtures thereof in all ratios, is brought into a suitable dosage form together with a solid, liquid or semi-liquid excipient or adjuvant and optionally with a further medicament active compound.

The pharmaceutical preparations according to the invention can be used as medicaments in human or veterinary medicine. The patient or host can belong to any mammal species, for example a primate species, particularly humans; rodents, including mice, rats and hamsters; rabbits; horses, cattle, dogs, cats, etc. Animal models are of interest for experimental investigations, where they provide a model for the treatment of a human disease.

Suitable carrier substances are organic or inorganic substances which are suitable for enteral (for example oral), parenteral or topical administration and do not react with the novel compounds, for example water, vegetable oils (such as sunflower oil or cod-liver oil), benzyl alcohols, polyethylene glycols, gelatine, carbohydrates, such as lactose or starch, magnesium stearate, talc, lanolin or Vaseline. Owing to his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, gel formers, tablet assistants and other active-ingredient carriers, it is also possible to use, for example, lubricants, stabilisers and/or wetting agents, emulsifiers, salts for influencing the osmotic pressure, antioxidants, dispersants, antifoams, buffer substances, flavours and/or aromas or flavour correctants, preservatives, solubilisers or dyes. If desired, preparations or medicaments according to the invention may comprise one or more further active compounds, for example one or more vitamins.

If desired, preparations or medicaments according to the invention may comprise one or more further active compounds and/or one or more action enhancers (adjuvants).

The terms "pharmaceutical formulation" and "pharmaceutical preparation" are used as synonyms for the purposes of the present invention.

As used here, "pharmaceutically tolerated" relates to medicaments, precipitation reagents, excipients, adjuvants, stabilisers, solvents and other agents which facilitate the administration of the pharmaceutical preparations obtained therefrom to a mammal without undesired physiological side effects, such as, for example, nausea, dizziness, digestion problems or the like.

In pharmaceutical preparations for parenteral administration, there is a requirement for isotonicity, euhydration and tolerability and safety of the formulation (low toxicity), of the adjuvants employed and of the primary packaging. Surprisingly, the compounds according to the invention preferably have the advantage that direct use is possible and further purification steps for the removal of toxicologically unacceptable agents, such as, for example, high concentrations of organic solvents or other toxicologically unacceptable adjuvants, are thus unnecessary before use of the compounds according to the invention in pharmaceutical formulations.

The invention particularly preferably also relates to pharmaceutical preparations comprising at least one compound according to the invention in precipitated noncrystalline, precipitated crystalline or in dissolved or suspended form, and optionally excipients and/or adjuvants and/or further pharmaceutical active compounds.

The compounds according to the invention preferably enable the preparation of highly concentrated formulations without unfavourable, undesired aggregation of the compounds according to the invention occurring. Thus, ready-to-use solutions having a high active-ingredient content can be prepared with the aid of compounds according to the invention with aqueous solvents or in aqueous media.

The compounds and/or physiologically acceptable salts and solvates thereof can also be lyophilised and the resultant lyophilisates used, for example, for the preparation of injection preparations.

Aqueous preparations can be prepared by dissolving or suspending compounds according to the invention in an aqueous solution and optionally adding adjuvants. To this end, defined volumes of stock solutions comprising the said further adjuvants in defined concentration are advantageously added to a solution or suspension having a defined concentration of compounds according to the invention, and the mixture is optionally diluted with water to the pre-calculated concentration. Alternatively, the adjuvants can be added in solid form. The amounts of stock solutions and/or water which are necessary in each case can subsequently be added to the aqueous solution or suspension obtained. Compounds according to the invention can also advantageously be dissolved or suspended directly in a solution comprising all further adjuvants.

The solutions or suspensions comprising compounds according to the invention and having a pH of 4 to 10, preferably having a pH of 5 to 9, and an osmolality of 250 to 350 mOsmol/kg can advantageously be prepared. The pharmaceutical preparation can thus be administered directly substantially without pain intravenously, intraarterially, intra-articularly, subcutaneously or percutaneously. In addition, the preparation may also be added to infusion solutions, such as, for example, glucose solution, isotonic saline solution or Ringer's solution, which may also contain further active compounds, thus also enabling relatively large amounts of active compound to be administered.

Pharmaceutical preparations according to the invention may also comprise mixtures of a plurality of compounds according to the invention.

The preparations according to the invention are physiologically well tolerated, easy to prepare, can be dispensed precisely and are preferably stable with respect to assay, decomposition products and aggregates throughout storage and transport and during multiple freezing and thawing processes. They can preferably be stored in a stable manner over a period of at least three months to two years at refrigerator temperature (2-8° C.) and at room temperature (23-27° C.) and 60% relative atmospheric humidity (R.H.).

For example, the compounds according to the invention can be stored in a stable manner by drying and when necessary converted into a ready-to-use pharmaceutical preparation by dissolution or suspension. Possible drying methods are, for example, without being restricted to these examples, nitrogen-gas drying, vacuum-oven drying, lyophilisation, washing with organic solvents and subsequent air drying, liquid-bed drying, fluidised-bed drying, spray drying, roller drying, layer drying, air drying at room temperature and further methods.

The term "effective amount" denotes the amount of a medicament or of a pharmaceutical active compound which causes in a tissue, system, animal or human a biological or medical response which is sought or desired, for example, by a researcher or physician.

In addition, the term "therapeutically effective amount" denotes an amount which, compared with a corresponding subject who has not received this amount, has the following consequence: improved treatment, healing, prevention or elimination of a disease, syndrome, disease state, complaint, disorder or prevention of side effects or also a reduction in the progress of a disease, complaint or disorder. The term "therapeutically effective amount" also encompasses the amounts which are effective for increasing normal physiological function.

On use of preparations or medicaments according to the invention, the compounds according to the invention and/or physiologically acceptable salts and solvates thereof are generally used analogously to known, commercially available preparations or preparations, preferably in dosages of between 0.1 and 500 mg, in particular 5 and 300 mg, per use unit. The daily dose is preferably between 0.001 and 250 mg/kg, in particular 0.01 and 100 mg/kg, of body weight. The preparation can be administered one or more times per day, for example two, three or four times per day. However, the individual dose for a patient depends on a large number of individual factors, such as, for example, on the efficacy of the particular compound used, on the age, body weight, general state of health, sex, nutrition, on the time and method of administration, on the excretion rate, on the combination with other medicaments and on the severity and duration of the particular disease.

A measure of the uptake of a medicament active compound in an organism is its bioavailability. If the medicament active compound is delivered to the organism intravenously in the form of an injection solution, its absolute bioavailability, i.e. the proportion of the pharmaceutical which reaches the systemic blood, i.e. the major circulation, in unchanged form, is 100%. In the case of oral administration of a therapeutic active compound, the active compound is generally in the form of a solid in the formulation and must therefore first be dissolved in order that it is able to overcome the entry barriers, for example the gastrointestinal tract, the oral mucous membrane, nasal membranes or the skin, in particular the stratum corneum, or can be absorbed by the body. Data on the pharmacokinetics, i.e. on the bioavailability, can be obtained analogously to the method of J. Shaffer et al., J. Pharm. Sciences, 88 (1999), 313-318.

Furthermore, medicaments of this type can be prepared by means of one of the processes generally known in the pharmaceutical art.

Medicaments can be adapted for administration via any desired suitable route, for example by the oral (including buccal or sublingual), rectal, pulmonary, nasal, topical (including buccal, sublingual or transdermal), vaginal or parenteral (including subcutaneous, intramuscular, intravenous, intradermal and in particular intra-articular) routes. Medicaments of this type can be prepared by means of all processes known in the pharmaceutical art by, for example, combining the active compound with the excipient(s) or adjuvant(s).

Parenteral administration is preferably suitable for administration of the medicaments according to the invention. In the case of parenteral administration, intra-articular administration is particularly preferred.

The invention thus preferably also relates to the use of a pharmaceutical preparation according to the invention for intra-articular administration in the treatment and/or prophylaxis of physiological and/or pathophysiological states selected from the group consisting of osteoarthritis, traumatic cartilage injuries, arthritis, pain, allodynia or hyperalgesia.

Intra-articular administration has the advantage that the compound according to the invention can be administered directly into the synovial fluid in the vicinity of the joint cartilage and is also able to diffuse from there into the cartilage tissue. Pharmaceutical preparations according to the invention can thus also be injected directly into the joint gap and thus develop their action directly at the site of action as intended. The compounds according to the invention are also suitable for the preparation of medicaments to be administered parenterally having slow, sustained and/or controlled release of active compound. They are thus also suitable for the preparation of delayed-release formulations, which are advantageous for the patient since administration is only necessary at relatively large time intervals.

The medicaments adapted to parenteral administration include aqueous and non-aqueous sterile injection solutions comprising antioxidants, buffers, bacteriostatics and solutes, by means of which the formulation is rendered isotonic with the blood or synovial fluid of the recipient to be treated; as well as aqueous and non-aqueous sterile suspensions, which can comprise suspension media and thickeners. The formulations can be delivered in single-dose or multi-dose containers, for example sealed ampoules and vials, and stored in the freeze-dried (lyophilised) state, so that only the addition of the sterile carrier liquid, for example water for injection purposes, immediately before use is necessary. Injection solutions and suspensions prepared in accordance with the formulation can be prepared from sterile powders, granules and tablets.

The compounds according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention can also be coupled to soluble polymers as targeted medicament excipients. Such polymers can encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds according to the invention can furthermore be coupled to a class of biodegradable polymers which are suitable for achieving slow release of a medicament, for example polylactic acid, poly-epsilon-caprolactone, polyhydroxybutyric acid, polyorthoesters, polyacetals, polydihydroxypyrans, polycyanoacrylates, polylactic-co-glycolic acid, polymers, such as conjugates between dextran and methacrylates, polyphosphoesters, various polysaccharides and polyamines and poly-ε-caprolactone, albumin, chitosan, collagen or modified gelatine and crosslinked or amphipathic block copolymers of hydrogels.

Suitable for enteral administration (oral or rectal) are, in particular, tablets, dragees, capsules, syrups, juices, drops or suppositories, and suitable for topical use are ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders. Also particularly suitable for topical uses are liposomal preparations.

In the case of formulation to give an ointment, the active compound can be employed either with a paraffinic or a water-miscible cream base. Alternatively, the active compound can be formulated to a cream with an oil-in-water cream base or a water-in-oil base.

Medicaments adapted to transdermal administration can be delivered as independent plasters for extended, close contact with the epidermis of the recipient. Thus, for example, the active compound can be supplied from the plaster by means of iontophoresis, as described in general terms in Pharmaceutical Research, 3 (6), 318 (1986).

It goes without saying that, besides the constituents particularly mentioned above, the medicaments according to the invention may also comprise other agents usual in the art with respect to the particular type of pharmaceutical formulation.

The invention also relates to a set (kit) consisting of separate packs of
a) an effective amount of a compound of the formula I and/or physiologically acceptable salts, derivatives, solvates, prodrugs and stereoisomers thereof, including mixtures thereof in all ratios, and
b) an effective amount of a further medicament active compound.

The set comprises suitable containers, such as boxes or cartons, individual bottles, bags or ampoules. The set may, for example, comprise separate ampoules each containing an effective amount of a compound of the formula I and/or pharmaceutically acceptable salts, derivatives, solvates, prodrugs and stereoisomers thereof, including mixtures thereof in all ratios, and an effective amount of a further medicament active compound in dissolved or lyophilised form.

Furthermore, the medicaments according to the invention can be used in order to provide additive or synergistic effects in certain known therapies and/or can be used in order to restore the efficacy of certain existing therapies.

Besides the compounds according to the invention, the pharmaceutical preparations according to the invention may also comprise further medicament active compounds, for example for use in the treatment of cancer, other anti-tumor medicaments. For the treatment of the other diseases mentioned, the pharmaceutical preparations according to the invention may also, besides the compounds according to the invention, comprise further medicament active compounds which are known to the person skilled in the art in the treatment thereof.

In one principal embodiment, methods are provided for enhancing an immune response in a host in need thereof. The immune response can be enhanced by reducing T cell tolerance, including by increasing IFN-γ release, by decreasing regulatory T cell production or activation, or by increasing antigen-specific memory T cell production in a host. In one embodiment, the method comprises administering a compound of the present invention to a host in combination or alternation with an antibody. In particular subembodiments, the antibody is a therapeutic antibody. In one particular embodiment, a method of enhancing efficacy of passive antibody therapy is provided comprising administering a compound of the present invention in combination or alternation with one or more passive antibodies. This method can enhance the efficacy of antibody therapy for treatment of abnormal cell proliferative disorders such as cancer, or can enhance the efficacy of therapy in the treatment or prevention of infectious diseases. The compound of the present invention can be administered in combination or alternation with antibodies such as rituximab, herceptin or erbitux, for example.

In another principal embodiment, a method of treating or preventing abnormal cell proliferation is provided comprising administering a compound of the present invention to a host in need thereof substantially in the absence of another anti-cancer agent.

In another principal embodiment, a method of treating or preventing abnormal cell proliferation in a host in need thereof is provided, comprising administering a first a compound of the present invention substantially in combination with a first anti-cancer agent to the host and subsequently administering a second $A_{2A}$ and/or $A_{2B}$ receptor antagonist. In one subembodiment, the second antagonist is administered substantially in the absence of another anti-cancer agent. In another principal embodiment, a method of treating or preventing abnormal cell proliferation in a host in need thereof is provided, comprising administering a compound of the present invention substantially in combination with a first anti-cancer agent to the host and subsequently administering a second anti-cancer agent in the absence of the antagonist.

Thus, the cancer treatment disclosed here can be carried out as therapy with a compound of the present invention or in combination with an operation, irradiation or chemotherapy. Chemotherapy of this type can include the use of one or more active compounds of the following categories of antitumour active compounds:

(i) antiproliferative/antineoplastic/DNA-damaging active compounds and combinations thereof, as used in medical oncology, such as alkylating active compounds (for example cis-platin, parboplatin, cyclophosphamide, nitrogen mustard, melphalan, chlorambucil, busulphan and nitrosoureas); antimetabolites (for example antifolates such as fluoropyrimidines such as 5-fluorouracil and tegafur, raltitrexed, methotrexate, cytosine arabinoside, hydroxyurea and gemcitabine); antitumour antibiotics (for example anthracyclines, such as adriamycin, bleomycin, doxorubicin, daunomycin, epirubicin, idarubicin, mitomycin-C, dactinomycin and mithramycin); antimitotic active compounds (for example vinca alkaloids, such as vincristine, vinblastine, vindesine and vinorelbine, and taxoids, such as taxol and taxotere); topoisomerase inhibitors (for example epipodophyllotoxins, such as etoposide and teniposide, amsacrine, topotecan, irinotecan and camptothecin) and cell-differentiating active compounds (for example all-trans-retinoic acid, 13-cis-retinoic acid and fenretinide);

(ii) cytostatic active compounds, such as anti-oestrogens (for example tamoxifen, toremifene, raloxifene, droloxifene and iodoxyfene), oestrogen receptor regulators (for example fulvestrant), anti-androgens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example anastrozole, letrozole, vorazole and exemestane) and inhibitors of 5α-reductase, such as finasteride;

(iii) active compounds which inhibit cancer invasion including for example metalloproteinase inhibitors, like marimastat, and inhibitors of urokinase plasminogen activator receptor function;

(iv) inhibitors of growth factor function, for example growth factor antibodies, growth factor receptor antibodies, for example the anti-erbb2 antibody trastuzumab [Herceptin™] and the anti-erbbI antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033), for example inhibitors of the platelet-derived growth factor family and, for example, inhibitors of the hepatocyte growth factor family;

(v) anti-angiogenic active compounds, such as bevacizumab, angiostatin, endostatin, linomide, batimastat, captopril, cartilage derived inhibitor, genistein, interleukin 12, lavendustin, medroxypregesterone acetate, recombinant human platelet factor 4, tecogalan, thrombospondin, TNP-470, anti-VEGF monoclonal antibody, soluble VEGF-receptor chimaeric protein, anti-VEGF receptor antibodies, anti-PDGF receptors, inhibitors of integrins, tyrosine kinase inhibitors, serine/threonine kinase inhibitors, antisense oligonucleotides, antisense oligodexoynucleotides, siRNAs, anti-VEGF aptamers, pigment epithelium derived factor and compounds which have been published in the international patent applications WO 97/22596, WO 97/30035, WO 97/32856 and WO 98/13354);

(vi) vessel-destroying agents, such as combretastatin A4 and compounds which have been published in the international patent applications WO 99/02166, WO 00/40529, WO 00/41669, WO 01/92224, WO 02/04434 and WO 02/08213;

(vii) antisense therapies, for example those directed to the targets mentioned above, such as ISIS 2503, an anti-Ras antisense;

(viii) gene therapy approaches, including, for example, approaches for replacement of abnormal, modified genes, such as abnormal p53 or abnormal BRCA1 or BRCA2, GDEPT approaches (gene-directed enzyme pro-drug therapy), such as those which use cytosine deaminase, thymidine kinase or a bacterial nitroreductase enzyme, and approaches which increase the tolerance of a patient to chemotherapy or radiotherapy, such as multi-drug resistance therapy; and (ix) immunotherapy approaches, including, for example, ex-vivo and in-vivo approaches for increasing the immunogenicity of tumour cells of a patient, such as transfection with cytokines, such as interleukin 2, interleukin 4 or granulocyte macrophage colony stimulating factor, approaches for decreasing T-cell anergy, approaches using transfected immune cells, such as cytokine-transfected dendritic cells, approaches for use of cytokine-transfected tumour cells and approaches for use of anti-idiotypic antibodies (x) chemotherapeutic agents including for example abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, epirubicin, epoetin alfa, estramustine, etoposide, exemestane, filgrastim, floxuridine, fludarabine, fluorouracil, fulvestrant and gemcitabine.

The medicaments from table 1 can preferably, but not exclusively, be combined with the compounds of the formula I.

TABLE 1

| | | |
|---|---|---|
| Alkylating active compounds | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum active compounds | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharrna) |
| | Methotrexate | DMDC (Hoffman-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |

TABLE 1-continued

| Category | | |
|---|---|---|
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic active compounds | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobuiin (Warner-Lambert) | Combretastatin A4 (BMS) |
| | Cemadotin (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilone B (Novartis) | AZ10992 (Asahi) |
| | T 900607 (Tularik) | !DN-5109 (Indena) |
| | T 138067 (Tularik) | AVLB (Prescient NeuroPharma) |
| | Cryptophycin 52 (Eli Lilly) | Azaepothilon B (BMS) |
| | Vinflunine (Fabre) | BNP-7787 (BioNumerik) |
| | Auristatin PE (Teikoku Hormone) | CA-4-prodrug (OXiGENE) |
| | BMS 247550 (BMS) | Dolastatin-10 (NrH) |
| | BMS 184476 (BMS) | CA-4 (OXiGENE) |
| | BMS 188797 (BMS) | |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate Synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (isotope solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Scherinq AG) | |
| Histone acetyl transferase inhibitors | Tacedinaline (Pfizer) | Pivaloyloxymethyl butyrate (Titan) |
| | SAHA (Aton Pharma) | Depsipeptide (Fujisawa) |
| | MS-275 (Schering AG) | |
| Metalloproteinase inhibitors | Neovastat (Aeterna Laboratories) | CMT-3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |

TABLE 1-continued

| | | |
|---|---|---|
| Retinoic acid receptor agonists | Fenretinide (Johnson & Johnson) LGD-1550 (ligand) | Alitretinoin (Ligand) |
| Immunomodulators | Interferon Oncophage (Antigenics) GMK (Progenies) Adenocarcinoma vaccine (Biomira) CTP-37 (AVI BioPharma) JRX-2 (Immuno-Rx) PEP-005 (Peplin Biotech) Synchrovax vaccines (CTL Immuno) Melanoma vaccines (CTL Immuno) p21-RAS vaccine (GemVax) | Dexosome therapy (Anosys Pentrix (Australian Cancer Technology) JSF-154 (Tragen) Cancer vaccine (Intercell) Norelin (Biostar) BLP-25 (Biomira) MGV (Progenies) !3-Alethin (Dovetail) CLL-Thera (Vasogen) |
| Hormonal and antihormonal active compounds | Oestrogens Conjugated oestrogens Ethynyloestradiol Chlorotrianisene Idenestrol Hydroxyprogesterone caproate Medroxyprogesterone Testosterone Testosterone propionate Fluoxymesterone Methyltestosterone Diethylstilbestrol Megestrol Tamoxifen Toremofin Dexamethasone | Prednisone Methylprednisolone Prednisolone Aminoglutethimide Leuprolide Goserelin Leuporelin Bicalutamide Flutamide Octreotide Nilutamide Mitotan P-04 (Novogen) 2-Methoxyoestradiol (En_treMed) Arzoxifen (Eli Lilly) |
| Photodynamic active compounds | Talaporfin (Light Sciences) Theralux (Theratechnologies) Motexafin-Gadolinium (Pharmacyclics) | Pd bacteriopheophorbide (Yeda) Lutetium texaphyrin (Pharmacyclics) Hypericin |
| Tyrosine kinase inhibitors | Imatinib (Novartis) Leflunomide(Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) |
| Various other active compounds | SR-27897 (CCK-A inhibitor, Sanofi-Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant, Bavarian Nordic) GCS-IOO (gal3 antagonist, GlycoGenesys) G17DT immunogen (gastrin inhibitor, Aphton) Efaproxiral (oxygenator, Alios Therapeutics) PI-88 (heparanase inhibitor, Progen) Tesmilifen (histamine antagonist, YM BioSciences) Histamine (histamine H2 receptor agonist, Maxim) Tiazofurin (IMPDH inhibitor, Ribapharm) | BCX-1777(PNP inhibitor, BioCryst) Ranpirnase (ribonuclease stimulant, Alfacell) Galarubicin (RNA synthesis inhibitor, Dong-A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, Active Biotech) Seocalcitol (vitamin D receptor agonist, Leo) 131-I-TM-601 (DNA antagonist, TransMolecular) Eflornithin (ODC inhibitor, ILEX Oncology) Minodronic acid (osteoclast inhibitor, Yamanouchi) Indisulam (p53 stimulant, Eisai) |

TABLE 1-continued

| | |
|---|---|
| Cilengitide (integrin antagonist, Merck KGaA) | Aplidin (PPT inhibitor, PharmaMar) |
| SR-31747 (IL-1 antagonist, Sanofi-Synthelabo) | Rituximab (CD20 antibody, Genentech) |
| CCI-779 (mTOR kinase inhibitor, Wyeth) | Gemtuzumab (CD33 antibody, Wyeth Ayerst) |
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | trans-Retinoic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

Even without further embodiments, it is assumed that a person skilled in the art will be able to use the above description in the broadest scope. The preferred embodiments should therefore merely be regarded as descriptive disclosure which is absolutely not limiting in any way.

The following examples are thus intended to explain the invention without limiting it. Unless indicated otherwise, percent data denote percent by weight. All temperatures are indicated in degrees Celsius. "Conventional work-up": water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation.

Rf values on silica gel; mass spectrometry: EI (electron impact ionisation): M$^+$, FAB (fast atom bombardment): (M+H)$^+$, THF (tetrahydrofuran), NMP (N-methylpyrrolidone), DMSO (dimethyl sulfoxide), EA (ethyl acetate), MeOH (methanol), TLC (thin-layer chromatography)

LIST OF ABBREVIATIONS

AUC Area under the plasma drug concentration-time curve
$C_{max}$ Maximum plasma concentration
CL Clearance
CV Coefficient of variation
CYP Cytochrome P450
DMSO Dimethyl sulfoxide
F Bioavailability
$f_a$ Fraction absorbed
iv Intravenous
LC-MS/MS Liquid chromatography tandem mass spectrometry
LLOQ Lower limit of quantification
NC Not calculated
ND Not determined
PEG Polyethylene glycol
Pgp Permeability glycoprotein
PK Pharmacokinetic(s)
po Per os (oral)
$t_{1/2}$ Half-life
$t_{max}$ Time at which maximum plasma concentration of drug is reached
UPLC Ultra performance liquid chromatography
$V_{ss}$ Volume of distribution (at steady state)
v/v Volume to volume

EXAMPLE 1: EXAMPLES OF COMPOUNDS OF THE PRESENT INVENTION

The invention especially relates to the compounds of table 2 and physiologically acceptable salts, derivatives, solvates, prodrugs and stereoisomers thereof, including mixtures thereof in all ratios.

TABLE 2 examples of compounds of the present invention

| No. | Structure | IUPAC-Name |
|---|---|---|
| 1 | 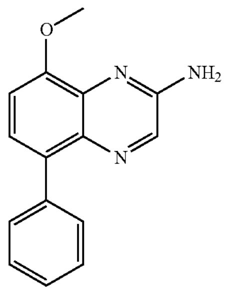 [SMILES: COc1ccc(-c2ccccc2)c2ncc(N)nc12] | N-[8-methoxy-5-(oxan-4-yl)quinoxalin-2-yl]-2-oxa-7-azaspiro[4.4]nonane-7-carboxamide |
| 2 | 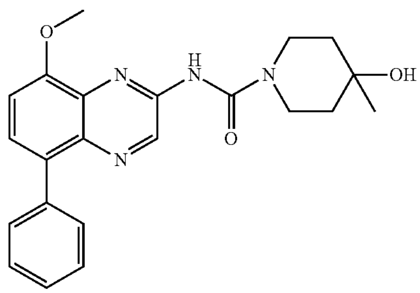 [SMILES: COc1ccc(-c2ccccc2)c2ncc(NC(=O)N3CCC(C)(O)CC3)nc12] | 4-hydroxy-N-[8-methoxy-5-(pyridin-4-yl)quinoxalin-2-yl]-4-methylpiperidine-1-carboxamide |
| 3 | 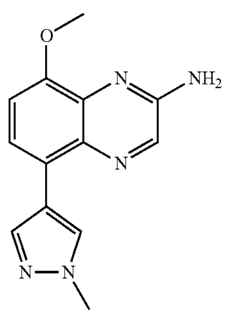 [SMILES: COc1ccc(-c2cnn(C)c2)c2ncc(N)nc12] | 3-hydroxy-N-[8-methoxy-5-(oxan-4-yl)quinoxalin-2-yl]-3-methylpyrrolidine-1-carboxamide |
| 4 | 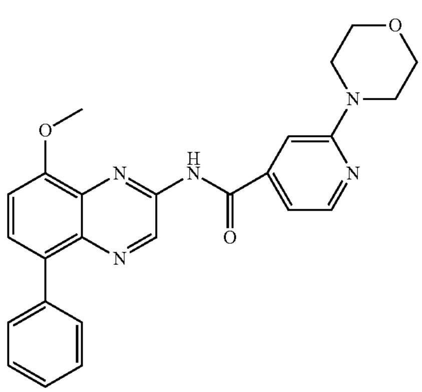 [SMILES: COc1ccc(-c2ccccc2)c2ncc(NC(=O)c3ccnc(N4CCOCC4)c3)nc12] | N-[8-methoxy-5-(oxan-4-yl)quinoxalin-2-yl]-2-methyl-1,3-oxazole-4-carboxamide |

TABLE 2-continued examples of compounds of the present invention

| No. | Structure | IUPAC-Name |
|---|---|---|
| 5 | 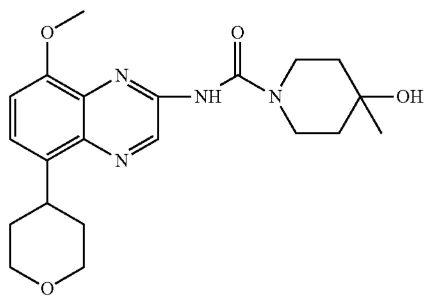 [SMILES: COc1ccc(C2CCOCC2)c2ncc(NC(=O)N3CCC(C)(O)CC3)nc12] | 4-(hydroxymethyl)-N-[8-methoxy-5-(oxan-4-yl)quinoxalin-2-yl]-4-methylpiperidine-1-carboxamide |
| 6 | 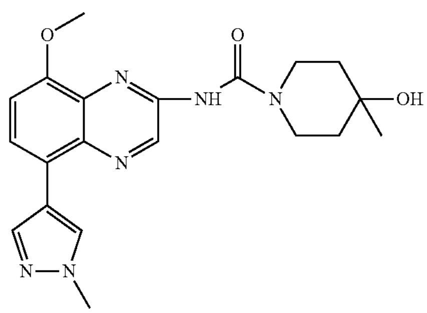 [SMILES: COc1ccc(-c2cnn(C)c2)c2ncc(NC(=O)N3CCC(C)(O)CC3)nc12] | N-[8-methoxy-5-(oxan-4-yl)quinoxalin-2-yl]-2,2-dioxo-2lambda6-thia-6-azaspiro[3.3]heptane-6-carboxamide |
| 7 | 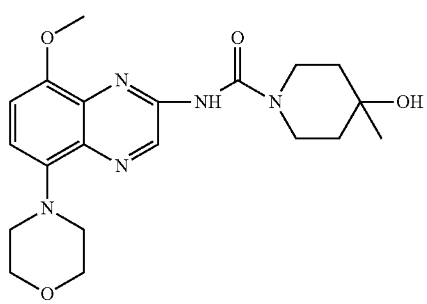 [SMILES: COc1ccc(N2CCOCC2)c2ncc(NC(=O)N3CCC(C)(O)CC3)nc12] | 6-methoxy-N-[8-methoxy-5-(oxan-4-yl)quinoxalin-2-yl]pyridazine-3-carboxamide |
| 8 | 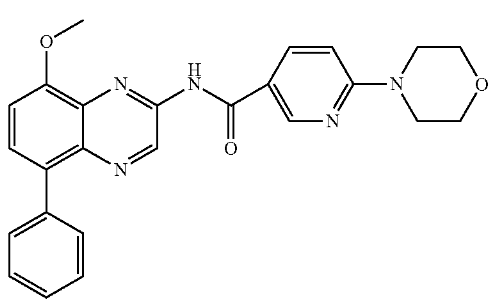 [SMILES: COc1ccc(-c2ccccc2)c2ncc(NC(=O)c3ccc(N4CCOCC4)nc3)nc12] | N-[8-methoxy-5-(oxan-4-yl)quinoxalin-2-yl]-1-(2-methoxyethyl)-1H-pyrazole-4-carboxamide |

TABLE 2-continued examples of compounds of the present invention

| No. | Structure | IUPAC-Name |
| --- | --- | --- |
| 9 | 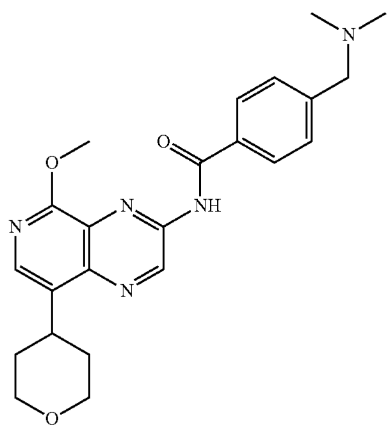 [SMILES: COc1ncc(C2CCOCC2)c2ncc(NC(=O)c3ccc(CN(C)C)cc3)nc12] | 4-hydroxy-N-(8-methoxy-5-phenylquinoxalin-2-yl)-4-(prop-2-yn-1-yl)piperidine-1-carboxamide |
| 10 | 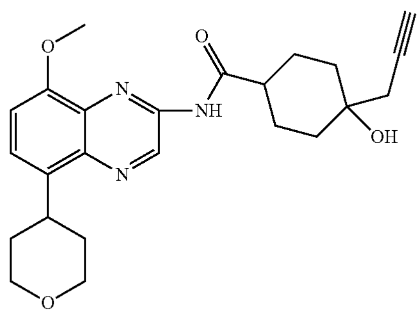 [SMILES: C#CCC1(O)CCC(C(=O)Nc2cnc3c(C4CCOCC4)ccc(OC)c3n2)CC1] | 3-hydroxy-N-(8-methoxy-5-phenylquinoxalin-2-yl)-3-methylpyrrolidine-1-carboxamide |
| 11 | 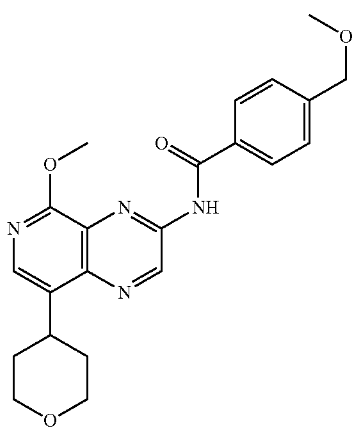 [SMILES: COCc1ccc(C(=O)Nc2cnc3c(C4CCOCC4)cnc(OC)c3n2)cc1] | 4-(hydroxymethyl)-N-(8-methoxy-5-phenylquinoxalin-2-yl)-4-methylpiperidine-1-carboxamide |
| 12 | 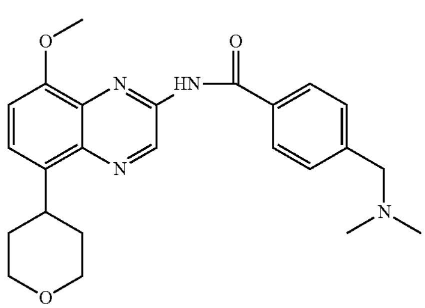 [SMILES: COc1ccc(C2CCOCC2)c2ncc(NC(=O)c3ccc(CN(C)C)cc3)nc12] | N-(8-methoxy-5-phenylquinoxalin-2-yl)-8-oxa-2-azaspiro[4.5]decane-2-carboxamide |

TABLE 2-continued examples of compounds of the present invention

| No. | Structure | IUPAC-Name |
|---|---|---|
| 13 | 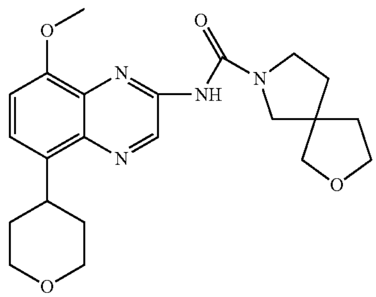 [SMILES: COc1ccc(C2CCOCC2)c2ncc(NC(=O)N3CCC4(CCOC4)C3)nc12] | N-(8-methoxy-5-phenylquinoxalin-2-yl)-2-oxa-7-azaspiro[4.4]nonane-7-carboxamide |
| 14 | 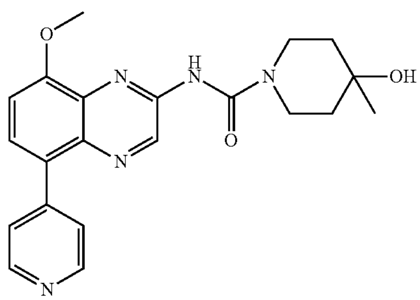 [SMILES: COc1ccc(-c2ccncc2)c2ncc(NC(=O)N3CCC(C)(O)CC3)nc12] | N-(8-methoxy-5-phenylquinoxalin-2-yl)-2,2-dioxo-2lambda6-thia-6-azaspiro[3.3]heptane-6-carboxamide |
| 15 | 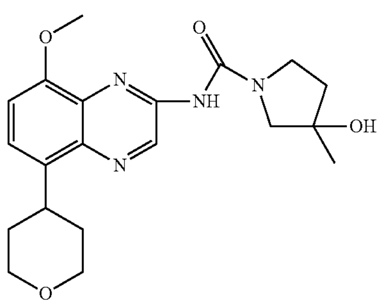 [SMILES: COc1ccc(C2CCOCC2)c2ncc(NC(=O)N3CCC(C)(O)C3)nc12] | 4-Hydroxy-4-methyl-piperidine-1-carboxylic acid (5-methoxy-8-phenyl-pyrido[3,4-b]pyrazin-3-yl)-amide |
| 16 | 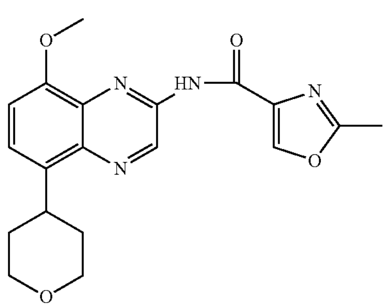 [SMILES: COc1ccc(C2CCOCC2)c2ncc(NC(=O)c3coc(C)n3)nc12] | 3-Hydroxy-3-methyl-pyrrolidine-1-carboxylic acid (5-methoxy-8-phenyl-pyrido[3,4-b]pyrazin-3-yl)-amide |
| 17 | 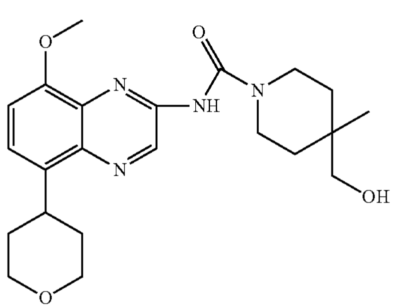 [SMILES: COc1ccc(C2CCOCC2)c2ncc(NC(=O)N3CCC(C)(CO)CC3)nc12] | 4-Hydroxymethyl-4-methyl-piperidine-1-carboxylic acid (5-methoxy-8-phenyl-pyrido[3,4-b]pyrazin-3-yl)-amide |

TABLE 2-continued examples of compounds of the present invention

| No. | Structure | IUPAC-Name |
| --- | --- | --- |
| 18 | 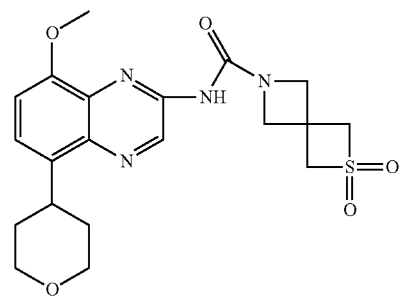 [SMILES: COc1ccc(C2CCOCC2)c2ncc(NC(=O)N3CC4(C3)CS(=O)(=O)C4)nc12] | N-[8-methoxy-5-(oxan-4-yl)quinoxalin-2-yl]-8-oxa-2-azaspiro[4.5]decane-2-carboxamide |
| 19 | 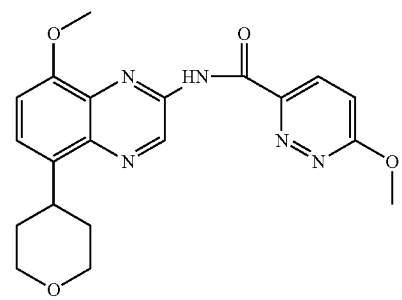 [SMILES: COc1ccc(C(=O)Nc2cnc3c(C4CCOCC4)ccc(OC)c3n2)nn1] | N-[8-methoxy-5-(oxan-4-yl)quinoxalin-2-yl]acetamide |
| 20 | 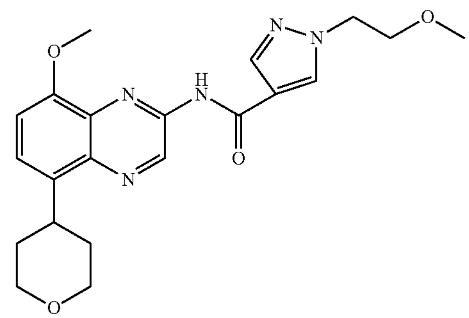 [SMILES: COCCn1cc(C(=O)Nc2cnc3c(C4CCOCC4)ccc(OC)c3n2)cn1] | 2,2,2-trifluoro-N-[8-methoxy-5-(oxan-4-yl)quinoxalin-2-yl]acetamide |
| 21 | 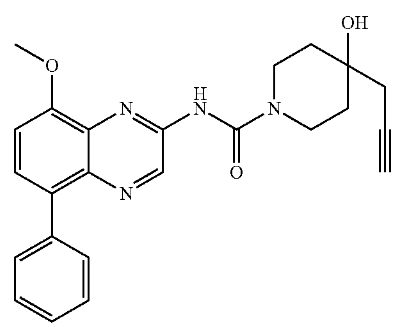 [SMILES: C#CCC1(O)CCN(C(=O)Nc2cnc3c(-c4ccccc4)ccc(OC)c3n2)CC1] | 4-Dimethylaminomethyl-N-(5-methoxy-8-phenyl-pyrido[3,4-b]pyrazin-3-yl)-benzamide |
| 22 | 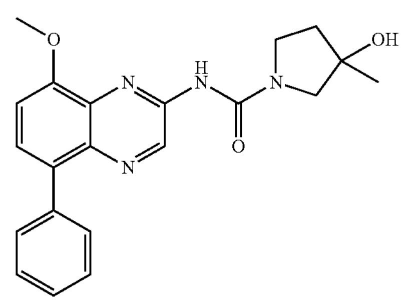 [SMILES: COc1ccc(-c2ccccc2)c2ncc(NC(=O)N3CCC(C)(O)C3)nc12] | 4-Hydroxy-4-prop-2-ynyl-piperidine-1-carboxylic acid (5-methoxy-8-phenyl-pyrido[3,4-b]pyrazin-3-yl)-amide |

TABLE 2-continued examples of compounds of the present invention

| No. | Structure | IUPAC-Name |
| --- | --- | --- |
| 23 | 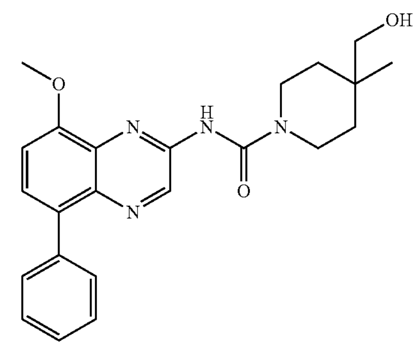 [SMILES: COc1ccc(-c2ccccc2)c2ncc(NC(=O)N3CCC(C)(CO)CC3)nc12] | 4-Methoxymethyl-N-(5-methoxy-8-phenyl-pyrido[3,4-b]pyrazin-3-yl)-benzamide |
| 24 | 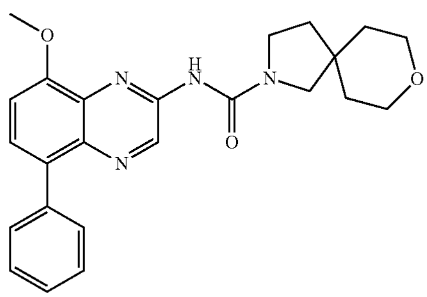 [SMILES: COc1ccc(-c2ccccc2)c2ncc(NC(=O)N3CCC4(CCOCC4)C3)nc12] | 1-(2-Methoxy-ethyl)-1H-pyrazole-4-carboxylic acid (5-methoxy-8-phenyl-pyrido[3,4-b]pyrazin-3-yl)-amide |
| 25 | 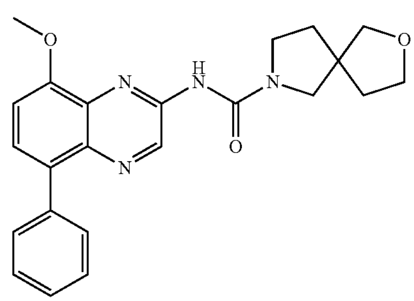 [SMILES: COc1ccc(-c2ccccc2)c2ncc(NC(=O)N3CCC4(CCOC4)C3)nc12] | 6-hydroxy-N-[8-methoxy-5-(oxan-4-yl)quinoxalin-2-yl]pyridazine-4-carboxamide |
| 26 | 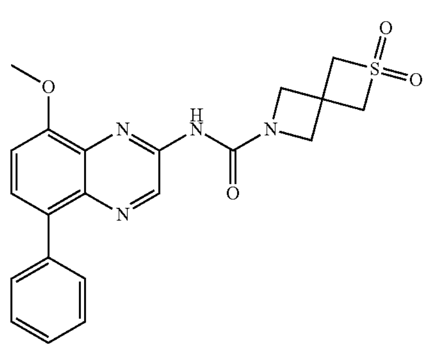 [SMILES: COc1ccc(-c2ccccc2)c2ncc(NC(=O)N3CC4(C3)CS(=O)(=O)C4)nc12] | 8-methoxy-5-(oxan-4-yl)quinoxalin-2-amine |

TABLE 2-continued examples of compounds of the present invention

| No. | Structure | IUPAC-Name |
|-----|-----------|------------|
| 27 | 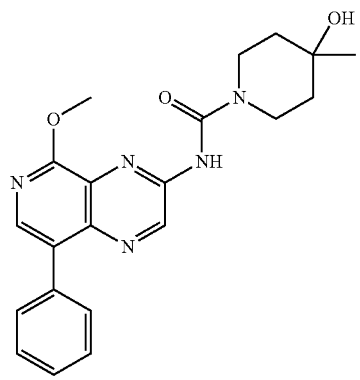 [SMILES: COc1ncc(-c2ccccc2)c2ncc(NC(=O)N3CCC(C)(O)CC3)nc12] | (3S)-3-hydroxy-N-[8-methoxy-5-(oxan-4-yl)quinoxalin-2-yl]-3-methylpyrrolidine-1-carboxamide |
| 28 | 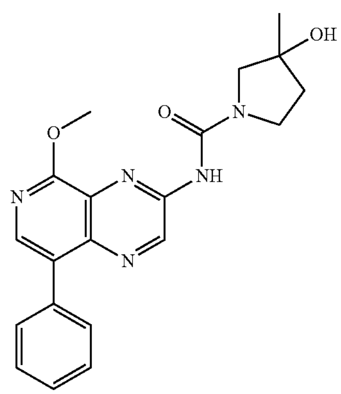 [SMILES: COc1ncc(-c2ccccc2)c2ncc(NC(=O)N3CCC(C)(O)C3)nc12] | (3R)-3-hydroxy-N-[8-methoxy-5-(oxan-4-yl)quinoxalin-2-yl]-3-methylpyrrolidine-1-carboxamide |
| 29 | 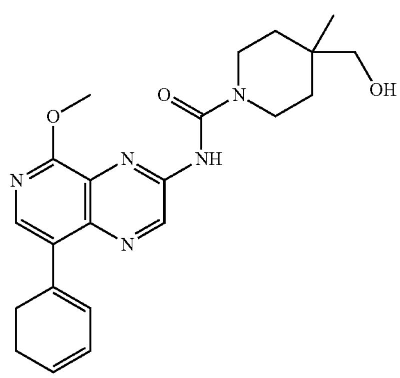 [SMILES: COc1ncc(C2=CC=CCC2)c2ncc(NC(=O)N3CCC(C)(CO)CC3)nc12] | 4-hydroxy-N-[8-methoxy-5-(2-methylphenyl)quinoxalin-2-yl]-4-methylpiperidine-1-carboxamide |
| 30 | 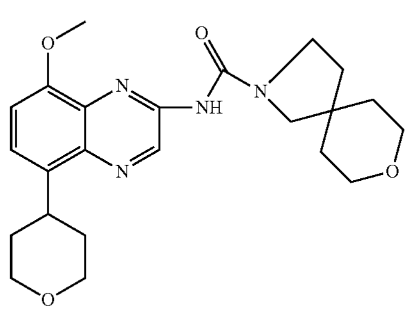 [SMILES: COc1ccc(C2CCOCC2)c2ncc(NC(=O)N3CCC4(CCOCC4)C3)nc12] | N-(8-methoxy-5-phenylquinoxalin-2-yl)-1-(2-methoxyethyl)-1H-pyrazole-4-carboxamide |

TABLE 2-continued examples of compounds of the present invention

| No. | Structure | IUPAC-Name |
|---|---|---|
| 31 | 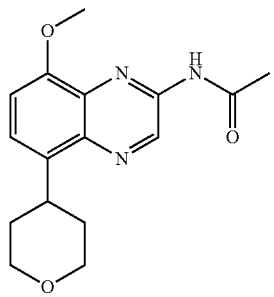 [SMILES: COc1ccc(C2CCOCC2)c2ncc(NC(C)=O)nc12] | N-(8-methoxy-5-phenylquinoxalin-2-yl)-2-methyl-1,3-oxazole-4-carboxamide |
| 32 | 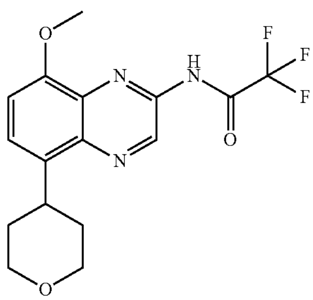 [SMILES: COc1ccc(C2CCOCC2)c2ncc(NC(=O)C(F)(F)F)nc12] | N-(8-methoxy-5-phenylquinoxalin-2-yl)-1-methyl-1H-pyrazole-4-carboxamide |
| 33 | 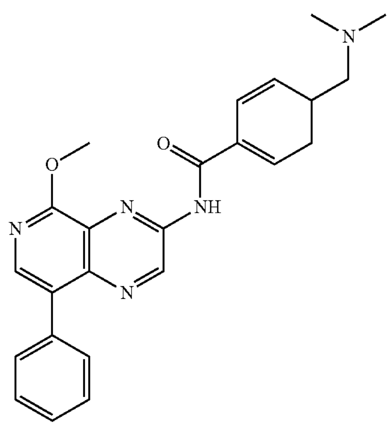 [SMILES: COc1ncc(-c2ccccc2)c2ncc(NC(=O)C3=CCC(CN(C)C)C=C3)nc12] | N-(8-methoxy-5-phenylquinoxalin-2-yl)cyclopropanecarboxamide |
| 34 | 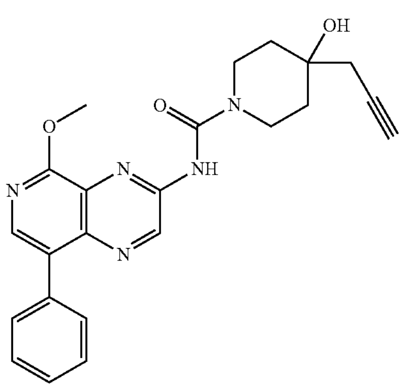 [SMILES: C#CCC1(O)CCN(C(=O)Nc2cnc3c(-c4ccccc4)cnc(OC)c3n2)CC1] | N-(8-methoxy-5-phenylquinoxalin-2-yl)-1-methyl-1H-pyrazole-5-carboxamide |

TABLE 2-continued examples of compounds of the present invention

| No. | Structure | IUPAC-Name |
|---|---|---|
| 35 | 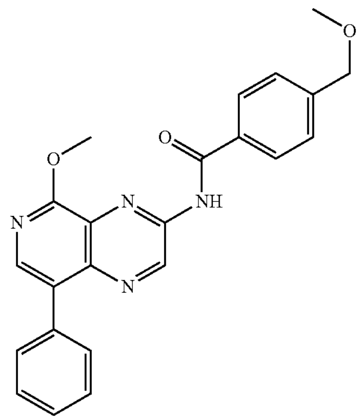 [SMILES: COCc1ccc(C(=O)Nc2cnc3c(-c4ccccc4)cnc(OC)c3n2)cc1] | N-(8-methoxy-5-phenylquinoxalin-2-yl)-13-thiazole-5-carboxamide |
| 36 | 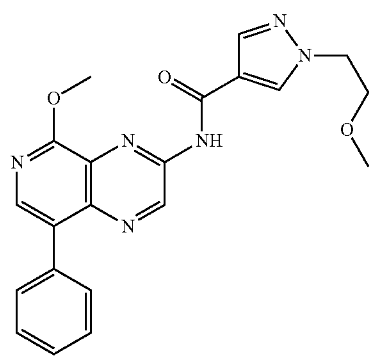 [SMILES: COCCn1cc(C(=O)Nc2cnc3c(-c4ccccc4)cnc(OC)c3n2)cn1] | N-(8-methoxy-5-phenylquinoxalin-2-yl)-2-methyl-1,3-thiazole-5-carboxamide |
| 37 | 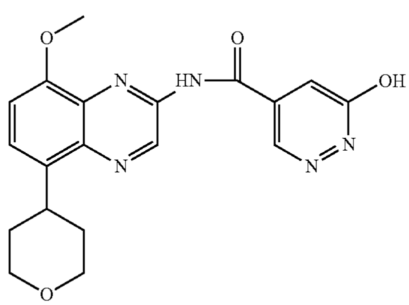 [SMILES: COc1ccc(C2CCOCC2)c2ncc(NC(=O)c3cnnc(O)c3)nc12] | N-(8-methoxy-5-phenylquinoxalin-2-yl)-4H-1,2,4-triazole-3-carboxamide |
| 38 | 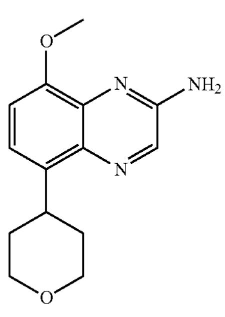 [SMILES: COc1ccc(C2CCOCC2)c2ncc(N)nc12] | N-[5-(4-fluorophenyl)-8-methoxyquinoxalin-2-yl]-4-hydroxy-4-methylpiperidine-1-carboxamide |

TABLE 2-continued examples of compounds of the present invention

| No. | Structure | IUPAC-Name |
|---|---|---|
| 39 | 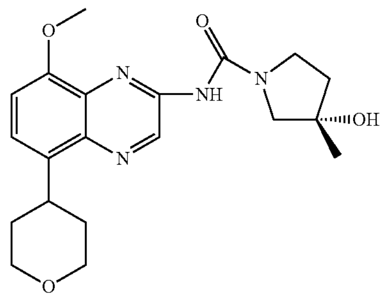 [SMILES: COc1ccc(C2CCOCC2)c2ncc(NC(=O)N3CC[C@](C)(O)C3)nc12] | 4-Hydroxy-4-methyl-piperidine-1-carboxylic acid [5-methoxy-8-(tetrahydro-pyran-4-yl)-pyrido[3,4-b]pyrazin-3-yl]-amide |
| 40 | 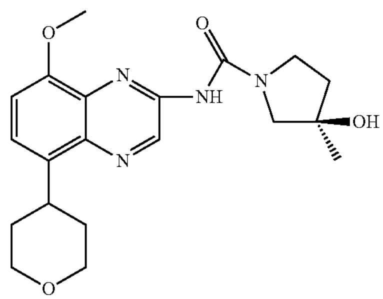 [SMILES: COc1ccc(C2CCOCC2)c2ncc(NC(=O)N3CC[C@@](C)(O)C3)nc12] | N-[8-methoxy-5-(oxan-4-yl)quinoxalin-2-yl]cyclopropanecarboxamide |
| 41 | 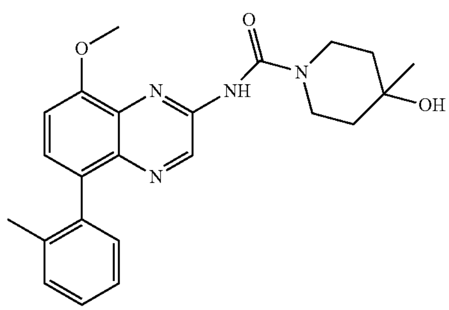 [SMILES: COc1ccc(-c2ccccc2C)c2ncc(NC(=O)N3CCC(C)(O)CC3)nc12] | 4-Hydroxy-4-methyl-piperidine-1-carboxylic acid [8-methoxy-5-(6-methyl-pyridazin-3-yl)-quinoxalin-2-yl]-amide |
| 42 | 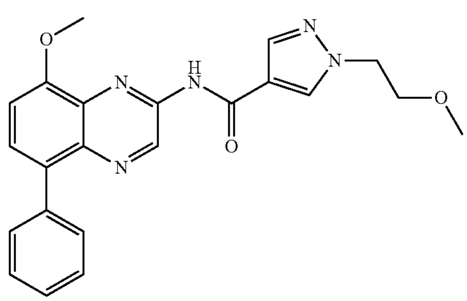 [SMILES: COCCn1cc(C(=O)Nc2cnc3c(-c4ccccc4)ccc(OC)c3n2)cn1] | 1-(2-Methoxy-ethyl)-1H-pyrazole-4-carboxylic acid [8-methoxy-5-(6-methyl-pyridazin-3-yl)-quinoxalin-2-yl]-amide |
| 43 | 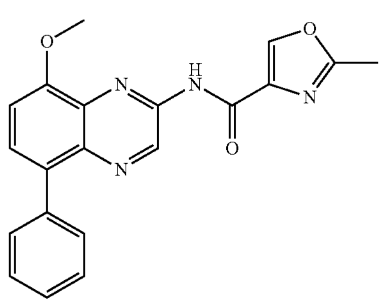 [SMILES: COc1ccc(-c2ccccc2)c2ncc(NC(=O)c3coc(C)n3)nc12] | 1-(2-Methoxy-ethyl)-1H-pyrazole-4-carboxylic acid (8-methoxy-5-pyridin-4-yl-quinoxalin-2-yl)-amide |

TABLE 2-continued examples of compounds of the present invention

| No. | Structure | IUPAC-Name |
|---|---|---|
| 44 | 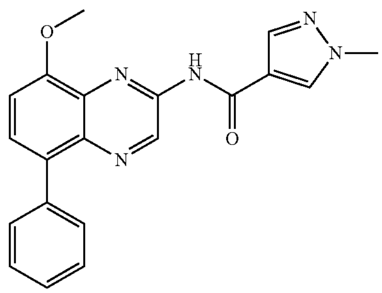 [SMILES: COc1ccc(-c2ccccc2)c2ncc(NC(=O)c3cnn(C)c3)nc12] | 1-(2-Methoxy-ethyl)-1H-pyrazole-4-carboxylic acid [5-methoxy-8-(tetrahydro-pyran-4-yl)-pyrido[3,4-b]pyrazin-3-yl]-amide |
| 45 | 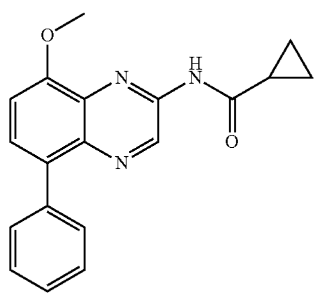 [SMILES: COc1ccc(-c2ccccc2)c2ncc(NC(=O)C3CC3)nc12] | Isoxazole-4-carboxylic acid (5-methoxy-8-phenyl-pyrido[3,4-b]pyrazin-3-yl)-amide |
| 46 | 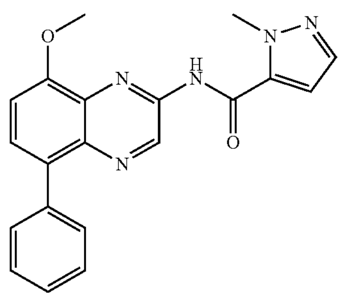 [SMILES: COc1ccc(-c2ccccc2)c2ncc(NC(=O)c3ccnn3C)nc12] | 4-Hydroxymethyl-4-methyl-piperidine-1-carboxylic acid [8-methoxy-5-(tetrahydro-pyran-4-yl)-quinoxalin-2-yl]-amide |
| 47 | 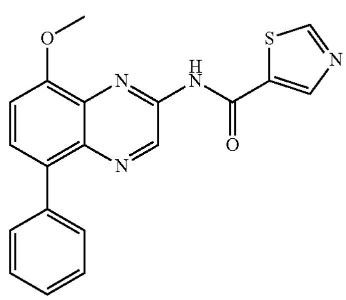 [SMILES: COc1ccc(-c2ccccc2)c2ncc(NC(=O)c3cncs3)nc12] | 3-Hydroxy-3-methyl-pyrrolidine-1-carboxylic acid [5-methoxy-8-(tetrahydro-pyran-4-yl)-pyrido[3,4-b]pyrazin-3-yl]-amide |
| 48 | 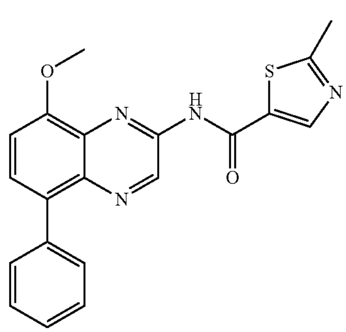 [SMILES: COc1ccc(-c2ccccc2)c2ncc(NC(=O)c3cnc(C)s3)nc12] | 4-Hydroxy-4-methyl-piperidine-1-carboxylic acid [5-(2-fluoro-phenyl)-8-methoxy-quinoxalin-2-yl]-amide |

TABLE 2-continued examples of compounds of the present invention

| No. | Structure | IUPAC-Name |
|---|---|---|
| 49 | 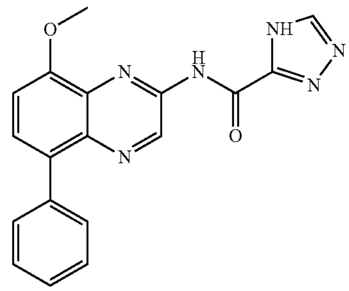 [SMILES: COc1ccc(-c2ccccc2)c2ncc(NC(=O)c3nnc[nH]3)nc12] | 4-Hydroxy-4-methyl-piperidine-1-carboxylic acid [5-(4-fluoro-phenyl)-8-methoxy-quinoxalin-2-yl]-amide |
| 50 | 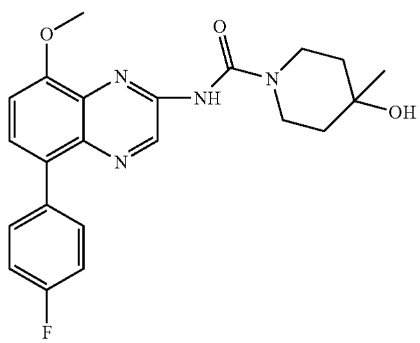 [SMILES: COc1ccc(-c2ccc(F)cc2)c2ncc(NC(=O)N3CCC(C)(O)CC3)nc12] | 4-Hydroxy-4-methyl-piperidine-1-carboxylic acid [5-(3-fluoro-phenyl)-8-methoxy-quinoxalin-2-yl]-amide |
| 51 | 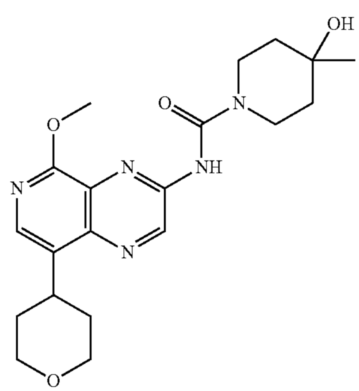 [SMILES: COc1ncc(C2CCOCC2)c2ncc(NC(=O)N3CCC(C)(O)CC3)nc12] | 4-Hydroxy-4-methyl-piperidine-1-carboxylic acid [8-methoxy-5-(2-oxa-7-aza-spiro[4.4]non-7-yl)-quinoxalin-2-yl]-amide |
| 52 | 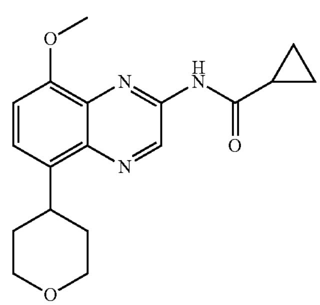 [SMILES: COc1ccc(C2CCOCC2)c2ncc(NC(=O)C3CC3)nc12] | 4-Hydroxy-4-methyl-piperidine-1-carboxylic acid (8-methoxy-5-pyridin-3-yl-quinoxalin-2-yl)-amide |

TABLE 2-continued examples of compounds of the present invention

| No. | Structure | IUPAC-Name |
|---|---|---|
| 53 | 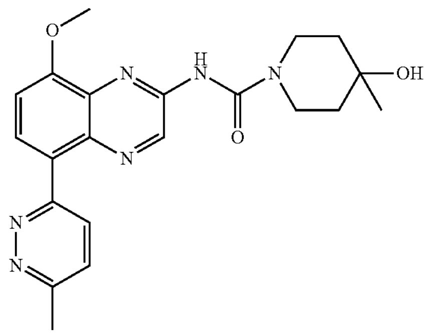 [SMILES: COc1ccc(-c2ccc(C)nn2)c2ncc(NC(=O)N3CCC(C)(O)CC3)nc12] | 4-Hydroxy-4-methyl-piperidine-1-carboxylic acid (5-azepan-1-yl-8-methoxy-quinoxalin-2-yl)-amide |
| 54 | 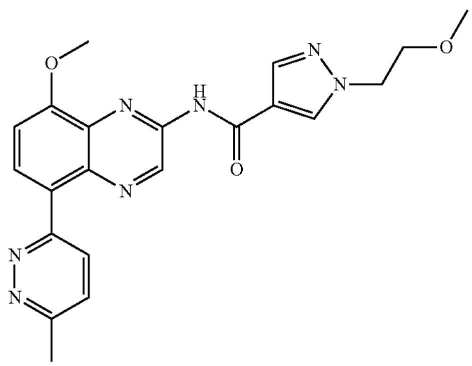 [SMILES: COCCn1cc(C(=O)Nc2cnc3c(-c4ccc(C)nn4)ccc(OC)c3n2)cn1] | 4-Hydroxy-4-methyl-piperidine-1-carboxylic acid (8-methoxy-5-phenyl-pyrido[3,4-b]pyrazin-2-yl)-amide |
| 55 | 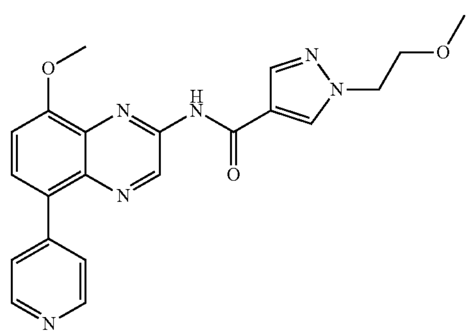 [SMILES: COCCn1cc(C(=O)Nc2cnc3c(-c4ccncc4)ccc(OC)c3n2)cn1] | Isoxazole-4-carboxylic acid [5-methoxy-8-(tetrahydro-pyran-4-yl)-pyrido[3,4-b]pyrazin-3-yl]-amide |
| 56 | 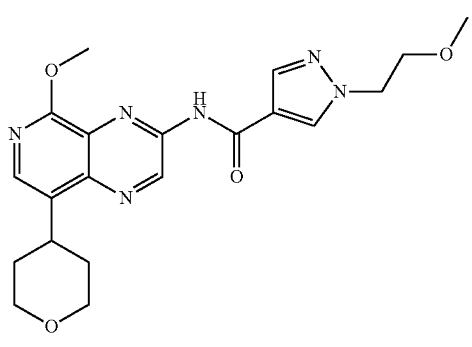 [SMILES: COCCn1cc(C(=O)Nc2cnc3c(C4CCOCC4)cnc(OC)c3n2)cn1] | 1-Methyl-1H-pyrazole-4-carboxylic acid [8-methoxy-5-(tetrahydro-pyran-4-yl)-quinoxalin-2-yl]-amide |

TABLE 2-continued examples of compounds of the present invention

| No. | Structure | IUPAC-Name |
| --- | --- | --- |
| 57 | 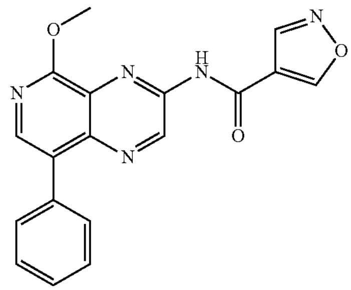 [SMILES: COc1ncc(-c2ccccc2)c2ncc(NC(=O)c3cnoc3)nc12] | 5-Methyl-isoxazole-4-carboxylic acid [8-methoxy-5-(tetrahydro-pyran-4-yl)-quinoxalin-2-yl]-amide |
| 58 | 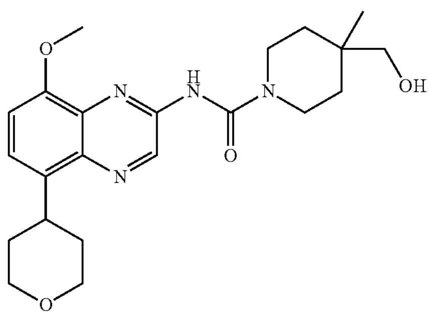 [SMILES: COc1ccc(C2CCOCC2)c2ncc(NC(=O)N3CCC(C)(CO)CC3)nc12] | 5-Cyclopropyl-isoxazole-4-carboxylic acid [8-methoxy-5-(tetrahydro-pyran-4-yl)-quinoxalin-2-yl]-amide |
| 59 | 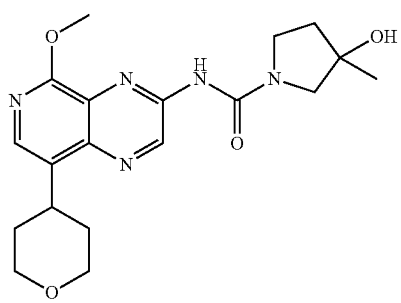 [SMILES: COc1ncc(C2CCOCC2)c2ncc(NC(=O)N3CCC(C)(O)C3)nc12] | 1-(2-Methoxy-ethyl)-1H-[1,2,3]triazole-4-carboxylic acid [8-methoxy-5-(tetrahydro-pyran-4-yl)-quinoxalin-2-yl]-amide |
| 60 | 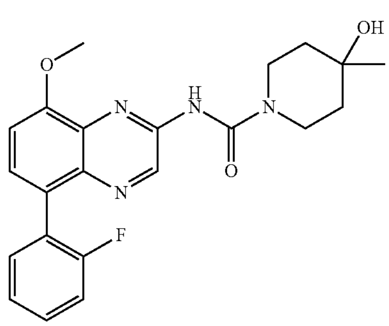 [SMILES: COc1ccc(-c2ccccc2F)c2ncc(NC(=O)N3CCC(C)(O)CC3)nc12] | 1-Methyl-1H-[1,2,3]triazole-4-carboxylic acid [8-methoxy-5-(tetrahydro-pyran-4-yl)-quinoxalin-2-yl]-amide |

TABLE 2-continued examples of compounds of the present invention

| No. | Structure | IUPAC-Name |
|---|---|---|
| 61 | 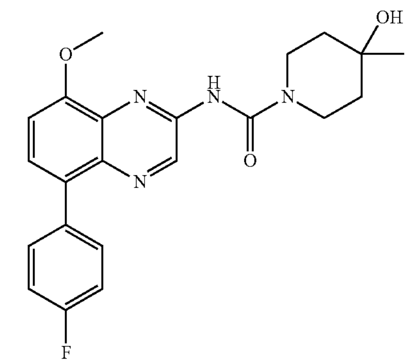 [SMILES: COc1ccc(-c2ccc(F)cc2)c2ncc(NC(=O)N3CCC(C)(O)CC3)nc12] | 1-Cyano-cyclopropanecarboxylic acid [8-methoxy-5-(tetrahydro-pyran-4-yl)-quinoxalin-2-yl]-amide |
| 62 | 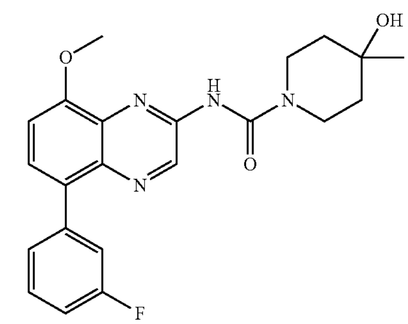 [SMILES: COc1ccc(-c2cccc(F)c2)c2ncc(NC(=O)N3CCC(C)(O)CC3)nc12] | Cyclopropanesulfonic acid [8-methoxy-5-(tetrahydro-pyran-4-yl)-quinoxalin-2-yl]-amide |
| 63 | 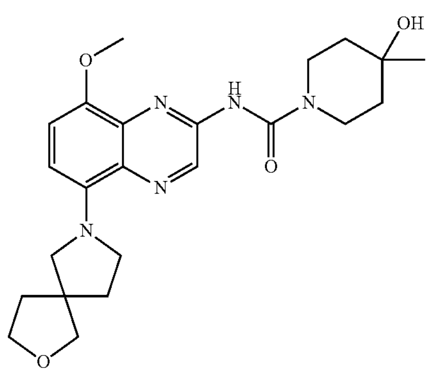 [SMILES: COc1ccc(N2CCC3(CCOC3)C2)c2ncc(NC(=O)N3CCC(C)(O)CC3)nc12] | [8-Methoxy-5-(tetrahydro-pyran-4-yl)-quinoxalin-2-yl]-carbamic acid isopropyl ester |
| 64 | 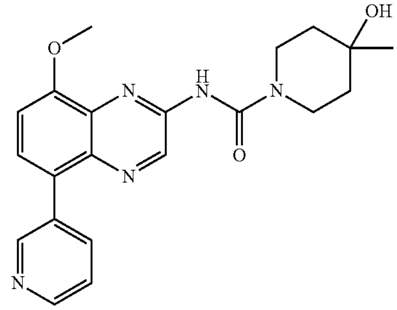 [SMILES: COc1ccc(-c2cccnc2)c2ncc(NC(=O)N3CCC(C)(O)CC3)nc12] | 2-Methyl-2H-pyrazole-3-carboxylic acid [8-methoxy-5-(tetrahydro-pyran-4-yl)-quinoxalin-2-yl]-amide |

TABLE 2-continued examples of compounds of the present invention

| No. | Structure | IUPAC-Name |
|---|---|---|
| 65 | 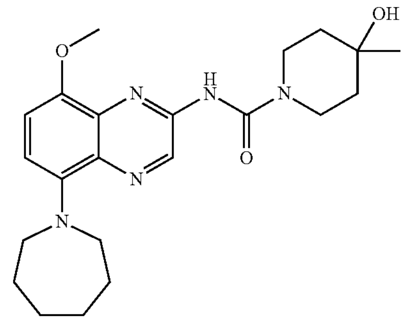 [SMILES: COc1ccc(N2CCCCCC2)c2ncc(NC(=O)N3CCC(C)(O)CC3)nc12] | Thiazole-5-carboxylic acid [8-methoxy-5-(tetrahydro-pyran-4-yl)-quinoxalin-2-yl]-amide |
| 66 | 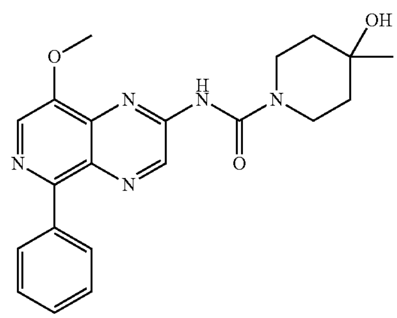 [SMILES: COc1cnc(-c2ccccc2)c2ncc(NC(=O)N3CCC(C)(O)CC3)nc12] | 2-Methyl-thiazole-5-carboxylic acid [8-methoxy-5-(tetrahydro-pyran-4-yl)-quinoxalin-2-yl]-amide |
| 67 | 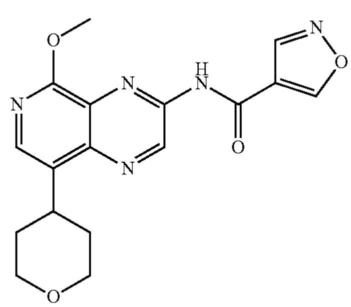 [SMILES: COc1ncc(C2CCOCC2)c2ncc(NC(=O)c3cnoc3)nc12] | 1H-[1,2,4]Triazole-3-carboxylic acid [8-methoxy-5-(tetrahydro-pyran-4-yl)-quinoxalin-2-yl]-amide |
| 68 | 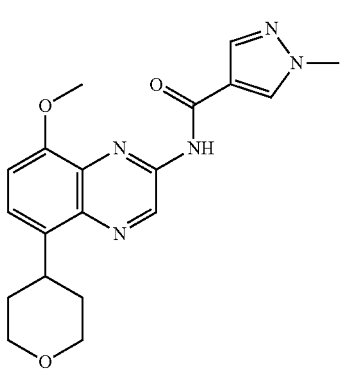 [SMILES: COc1ccc(C2CCOCC2)c2ncc(NC(=O)c3cnn(C)c3)nc12] | 2,3-Dimethyl-3H-imidazole-4-suflonic acid [8-methoxy-5-(tetrahydro-pyran-4-yl)-quinoxalin-2-yl]-amide |

TABLE 2-continued examples of compounds of the present invention

| No. | Structure | IUPAC-Name |
|---|---|---|
| 69 | 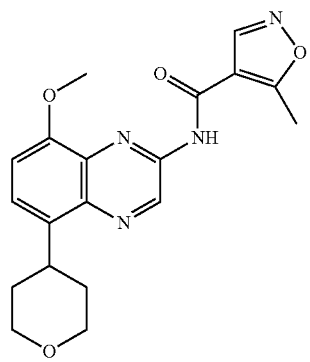 [SMILES: COc1ccc(C2CCOCC2)c2ncc(NC(=O)c3cnoc3C)nc12] | Imidazo[1,2-a]pyrazine-2-carboxylic acid [8-methoxy-5-(tetrahydro-pyran-4-yl)-quinoxalin-2-yl]-amide |
| 70 | 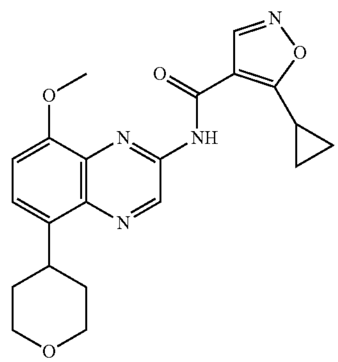 [SMILES: COc1ccc(C2CCOCC2)c2ncc(NC(=O)c3cnoc3C3CC3)nc12] | Azelidine-3-carboxylic acid [8-methoxy-5-(tetrahydro-pyran-4-yl)-quinoxalin-2-yl]-amide |
| 71 | 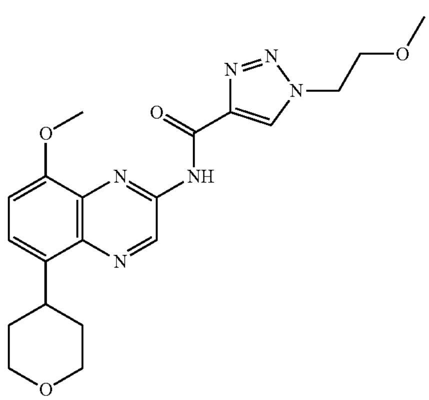 [SMILES: COCCn1cc(C(=O)Nc2cnc3c(C4CCOCC4)ccc(OC)c3n2)nn1] | Azetidine-3-carboxylic acid (8-methoxy-5-phenyl-quinoxalin-2-yl)-amide |
| 72 | 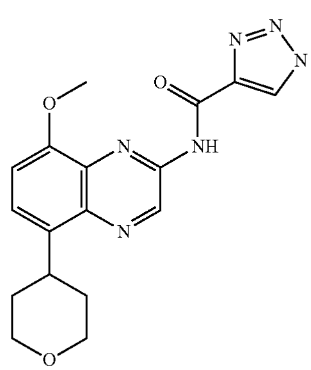 [SMILES: COc1ccc(C2CCOCC2)c2ncc(NC(=O)c3c[nH]nn3)nc12] | Imidazo[1,2-a]pyrazine-2-carboxylic acid (8-methoxy-5-phenyl-quinoxalin-2-yl)-amide |

TABLE 2-continued examples of compounds of the present invention

| No. | Structure | IUPAC-Name |
|---|---|---|
| 73 | 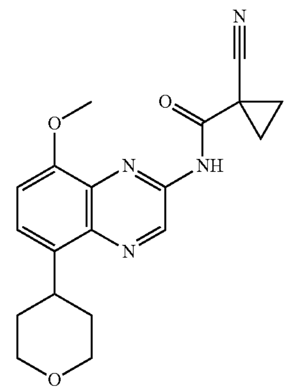 [SMILES: COc1ccc(C2CCOCC2)c2ncc(NC(=O)C3(C#N)CC3)nc12] | 2,3-Dimethyl-3H-imidazole-4-sulfonic acid (8-methoxy-5-phenyl-quinoxalin-2-yl)-amide |
| 74 | 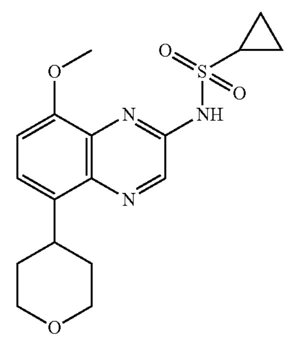 [SMILES: COc1ccc(C2CCOCC2)c2ncc(NS(=O)(=O)C3CC3)nc12] | (8-Methoxy-5-phenyl-quinoxalin-2-yl)-carbamic acid isopropyl ester |
| 75 | 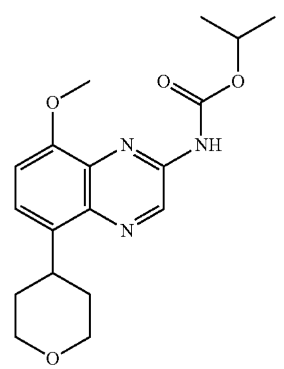 [SMILES: COc1ccc(C2CCOCC2)c2ncc(NC(=O)OC(C)C)nc12] | Cyclopropanesulfonic acid (8-methoxy-5-phenyl-quinoxalin-2-yl)-amide |
| 76 | 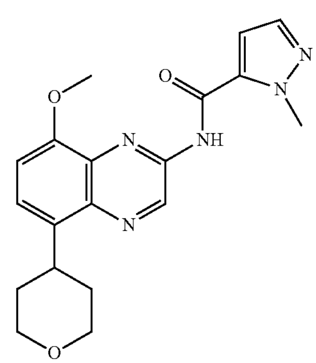 [SMILES: COc1ccc(C2CCOCC2)c2ncc(NC(=O)c3ccnn3C)nc12] | 1-Cyano-cyclopropanecarboxylic acid (8-methoxy-5-phenyl-quinoxalin-2-yl)-amide |

TABLE 2-continued examples of compounds of the present invention

| No. | Structure | IUPAC-Name |
|---|---|---|
| 77 | 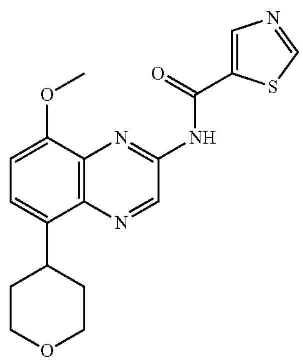 [SMILES: COc1ccc(C2CCOCC2)c2ncc(NC(=O)c3cncs3)nc12] | 1-Methyl-1H-[1,2,3]triazole-4-carboxylic acid (8-methoxy-5-phenyl-quinoxalin-2-yl)-amide |
| 78 | 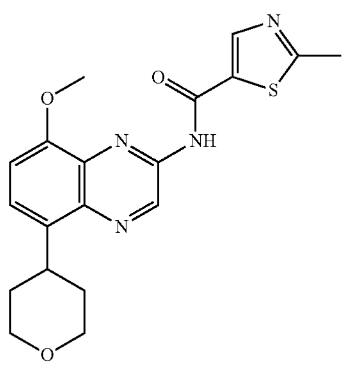 [SMILES: COc1ccc(C2CCOCC2)c2ncc(NC(=O)c3cnc(C)s3)nc12] | 1-(2-Methoxy-ethyl)-1H-[1,2,3]triazole-4-carboxylic acid (8-methoxy-5-phenyl-quinoxalin-2-yl)-amide |
| 79 | 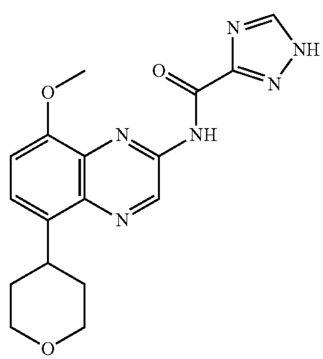 [SMILES: COc1ccc(C2CCOCC2)c2ncc(NC(=O)c3nc[nH]n3)nc12] | 5-Cyclopropyl-isoxazole-4-carboxylic acid (8-methoxy-5-phenyl-quinoxalin-2-yl)-amide |
| 80 | 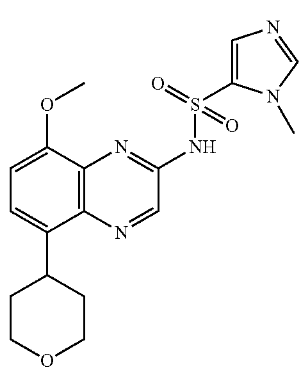 [SMILES: COc1ccc(C2CCOCC2)c2ncc(NS(=O)(=O)c3cncn3C)nc12] | 5-Methyl-isoxazole-4-carboxylic acid (8-methoxy-5-phenyl-quinoxalin-2-yl)-amide |

TABLE 2-continued examples of compounds of the present invention

| No. | Structure | IUPAC-Name |
|---|---|---|
| 81 | 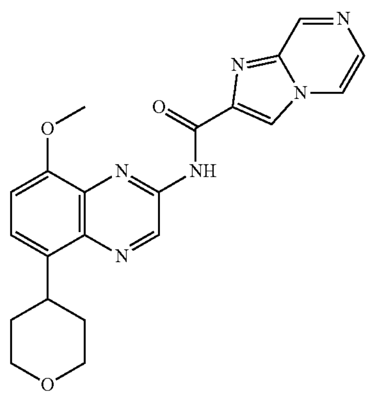 [SMILES: COc1ccc(C2CCOCC2)c2ncc(NC(=O)c3cn4ccncc4n3)nc12] | 1-Methyl-1H-pyrazole-4-carboxylic acid (8-methoxy-5-phenyl-quinoxalin-2-yl)-amide |
| 82 | 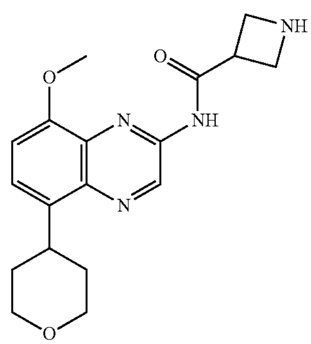 [SMILES: COc1ccc(C2CCOCC2)c2ncc(NC(=O)C3CNC3)nc12] | 6-Oxo-1,6-dihydro-pyridazine-4-carboxylic acid (8-methoxy-5-phenyl-quinoxalin-2-yl)-amide |
| 83 | 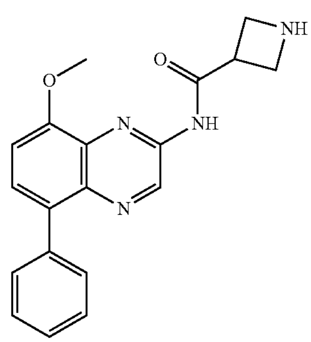 [SMILES: COc1ccc(-c2ccccc2)c2ncc(NC(=O)C3CNC3)nc12] | 4-Hydroxy-4-methyl-piperidine-1-carboxylic acid (5-butyl-8-methoxy-quinoxalin-2-yl)-amide |
| 84 | 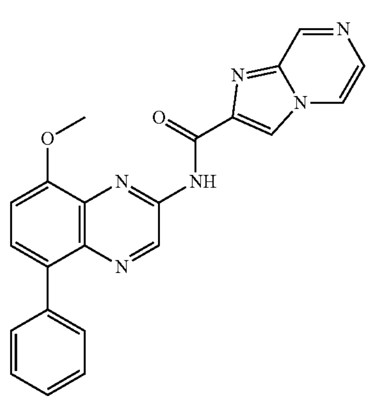 [SMILES: COc1ccc(-c2ccccc2)c2ncc(NC(=O)c3cn4ccncc4n3)nc12] | 4-Hydroxy-4-methyl-piperidine-1-carboxylic acid [8-methoxy-5-(1-propyl-cyclopropyl)-quinoxalin-2-yl]-amide |

TABLE 2-continued examples of compounds of the present invention

| No. | Structure | IUPAC-Name |
| --- | --- | --- |
| 85 | 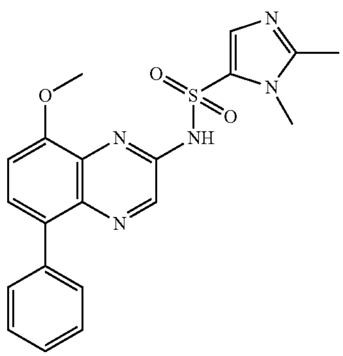 [SMILES: COc1ccc(-c2ccccc2)c2ncc(NS(=O)(=O)c3cnc(C)n3C)nc12] | 4-Hydroxy-4-methyl-piperidine-1-carboxylic acid [8-methoxy-5-(1-methoxymethyl-cyclopropyl)-quinoxalin-2-yl]-amide |
| 86 | 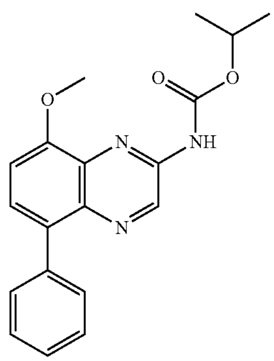 [SMILES: COc1ccc(-c2ccccc2)c2ncc(NC(=O)OC(C)C)nc12] | 4-Hydroxy-4-methyl-piperidine-1-carboxylic acid [5-(3-amino-phenyl)-8-methoxy-quinoxalin-2-yl]-amide |
| 87 | 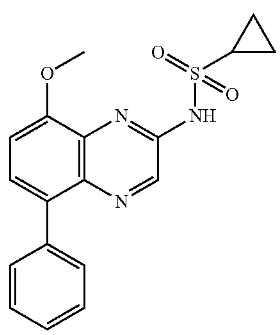 [SMILES: COc1ccc(-c2ccccc2)c2ncc(NS(=O)(=O)C3CC3)nc12] | 4-Hydroxy-4-methyl-piperidine-1-carboxylic acid (8-methoxy-5-pyridin-2-yl-quinoxalin-2-yl)-amide |
| 88 | 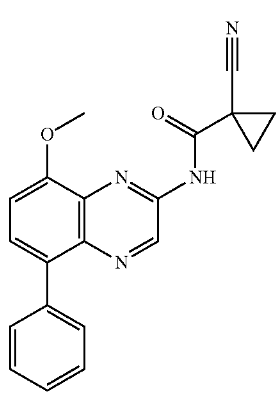 [SMILES: COc1ccc(-c2ccccc2)c2ncc(NC(=O)C3(C#N)CC3)nc12] | 4-Hydroxy-4-methyl-piperidine-1-carboxylic acid (8-methoxy-5-o-tolyl-quinoxalin-2-yl)-amide |

TABLE 2-continued examples of compounds of the present invention

| No. | Structure | IUPAC-Name |
|---|---|---|
| 89 | 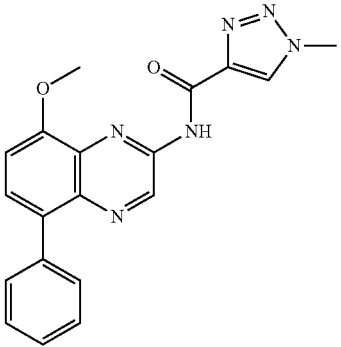 [SMILES: COc1ccc(-c2ccccc2)c2ncc(NC(=O)c3cn(C)nn3)nc12] | 1-Cyano-cyclopropanecarboxylic acid (5-methoxy-8-phenyl-pyrido[3,4-b]pyrazin-3-yl)-amide |
| 90 | 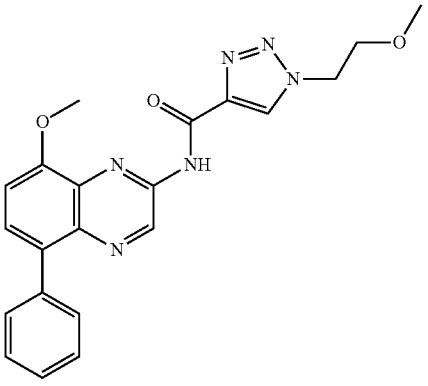 [SMILES: COCCn1cc(C(=O)Nc2cnc3c(-c4ccccc4)ccc(OC)c3n2)nn1] | Cyclopropanecarboxylic acid (5-methoxy-8-phenyl-pyrido[3,4-b]pyrazin-3-yl)-amide |
| 91 | 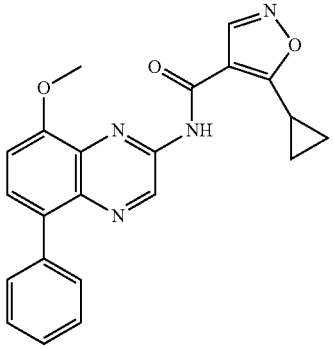 [SMILES: COc1ccc(-c2ccccc2)c2ncc(NC(=O)c3cnoc3C3CC3)nc12] | N-[8-methoxy-5-(oxan-4-yl)quinoxalin-2-yl]-2-oxa-7-azaspiro[4.4]nonane-7-carboxamide |
| 92 | 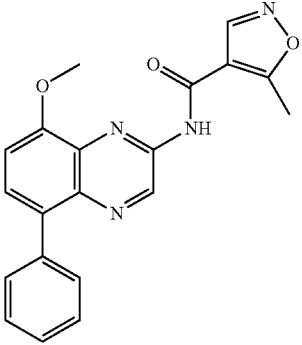 [SMILES: COc1ccc(-c2ccccc2)c2ncc(NC(=O)c3cnoc3C)nc12] | 4-hydroxy-N-[8-methoxy-5-(pyridin-4-yl)quinoxalin-2-yl]-4-methylpiperidine-1-carboxamide |

TABLE 2-continued examples of compounds of the present invention

| No. | Structure | IUPAC-Name |
|---|---|---|
| 93 | 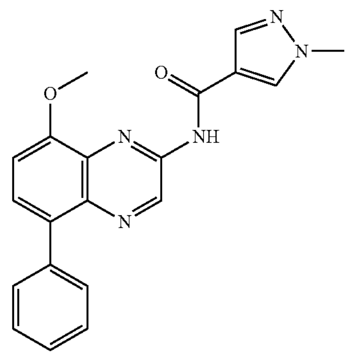 [SMILES: COc1ccc(-c2ccccc2)c2ncc(NC(=O)c3cnn(C)c3)nc12] | 3-hydroxy-N-[8-methoxy-5-(oxan-4-yl)quinoxalin-2-yl]-3-methylpyrrolidine-1-carboxamide |
| 94 | 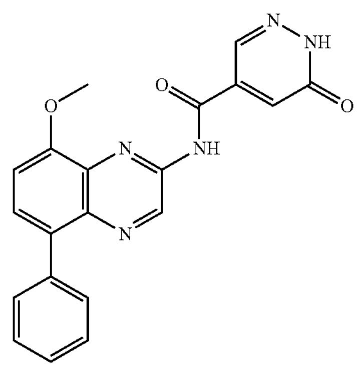 [SMILES: COc1ccc(-c2ccccc2)c2ncc(NC(=O)c3cn[nH]c(=O)c3)nc12] | N-[8-methoxy-5-(oxan-4-yl)quinoxalin-2-yl]-2-methyl-1,3-oxazole-4-carboxamide |
| 95 | 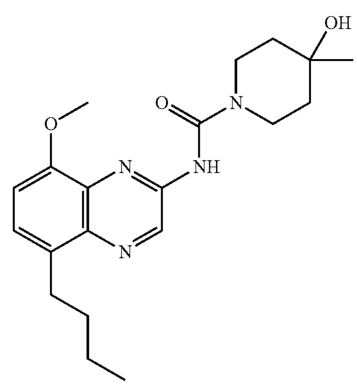 [SMILES: CCCCc1ccc(OC)c2nc(NC(=O)N3CCC(C)(O)CC3)cnc12] | 4-(hydroxymethyl)-N-[8-methoxy-5-(oxan-4-yl)quinoxalin-2-yl]-4-methylpiperidine-1-carboxamide |
| 96 | 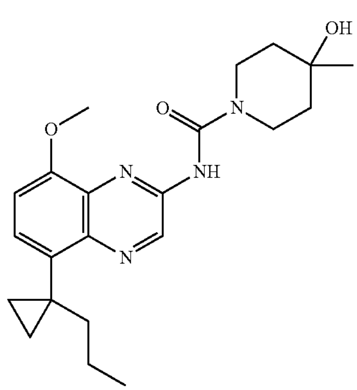 [SMILES: CCCC1(c2ccc(OC)c3nc(NC(=O)N4CCC(C)(O)CC4)cnc23)CC1] | N-[8-methoxy-5-(oxan-4-yl)quinoxalin-2-yl]-2,2-dioxo-2lambda6-thia-6-azaspiro[3.3]heptane-6-carboxamide |

TABLE 2-continued examples of compounds of the present invention

| No. | Structure | IUPAC-Name |
|---|---|---|
| 97 | 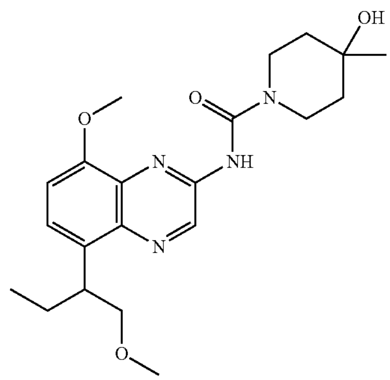 [SMILES: CCC(COC)c1ccc(OC)c2nc(NC(=O)N3CCC(C)(O)CC3)cnc12] | 6-methoxy-N-[8-methoxy-5-(oxan-4-yl)quinoxalin-2-yl]pyridazine-3-carboxamide |
| 98 | 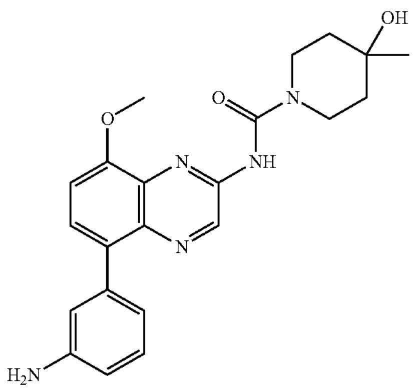 [SMILES: COc1ccc(-c2cccc(N)c2)c2ncc(NC(=O)N3CCC(C)(O)CC3)nc12] | N-[8-methoxy-5-(oxan-4-yl)quinoxalin-2-yl]-1-(2-methoxyethyl)-1H-pyrazole-4-carboxamide |
| 99 | 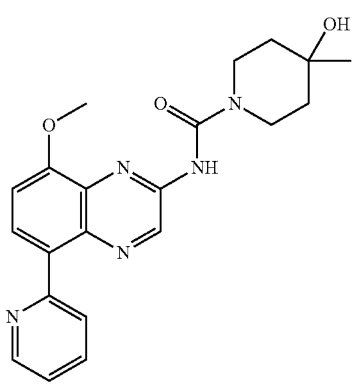 [SMILES: COc1ccc(-c2ccccn2)c2ncc(NC(=O)N3CCC(C)(O)CC3)nc12] | 4-hydroxy-N-(8-methoxy-5-phenylquinoxalin-2-yl)-4-(prop-2-yn-1-yl)piperidine-1-carboxamide |
| 100 | 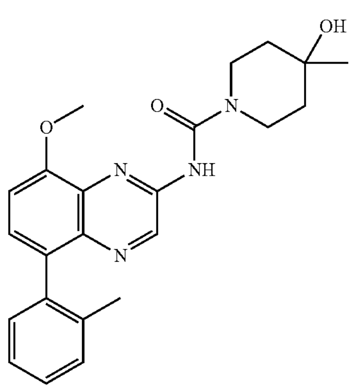 [SMILES: COc1ccc(-c2ccccc2C)c2ncc(NC(=O)N3CCC(C)(O)CC3)nc12] | 3-hydroxy-N-(8-methoxy-5-phenylquinoxalin-2-yl)-3-methylpyrrolidine-1-carboxamide |

TABLE 2-continued examples of compounds of the present invention

| No. | Structure | IUPAC-Name |
|---|---|---|
| 101 | 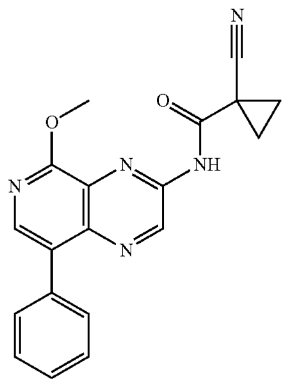 [SMILES: COc1ncc(-c2ccccc2)c2ncc(NC(=O)C3(C#N)CC3)nc12] | 4-(hydroxymethyl)-N-(8-methoxy-5-phenylquinoxalin-2-yl)-4-methylpiperidine-1-carboxamide |
| 102 | 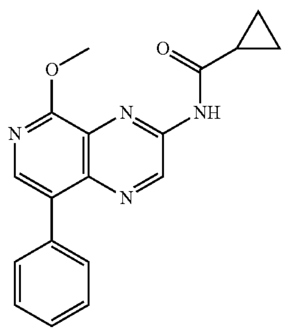 [SMILES: COc1ncc(-c2ccccc2)c2ncc(NC(=O)C3CC3)nc12] | N-(8-methoxy-5-phenylquinoxalin-2-yl)-8-oxa-2-azaspiro[4.5]decane-2-carboxamide |
| 103 | 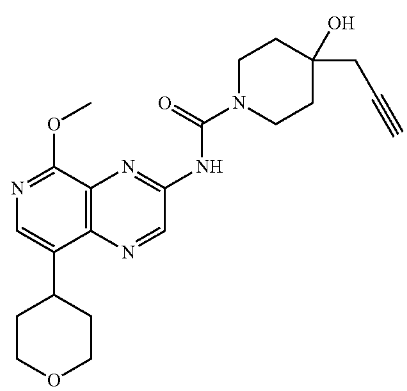 [SMILES: C#CCC1(O)CCN(C(=O)Nc2cnc3c(C4CCOCC4)cnc(OC)c3n2)CC1] | 4-Hydroxy-4-prop-2-ynyl-piperidine-1-carboxylic acid [5-methoxy-8-(tetrahydro-pyran-4-yl)-pyrido[3,4-b]pyrazin-3-yl]-amide |
| 104 | 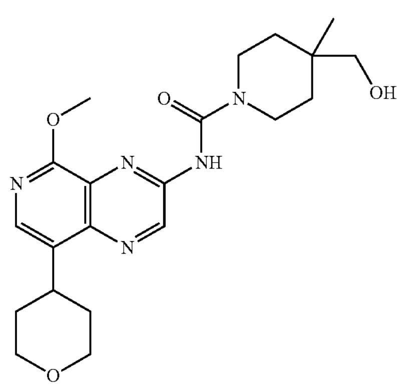 [SMILES: COc1ncc(C2CCOCC2)c2ncc(NC(=O)N3CCC(C)(CO)CC3)nc12] | 4-Hydroxymethyl-4-methyl-piperidine-1-carboxylic acid [5-methoxy-8-(tetrahydro-pyran-4-yl)-pyrido[3,4-b]pyrazin-3-yl]-amide |

TABLE 2-continued examples of compounds of the present invention

| No. | Structure | IUPAC-Name |
|---|---|---|
| 105 | 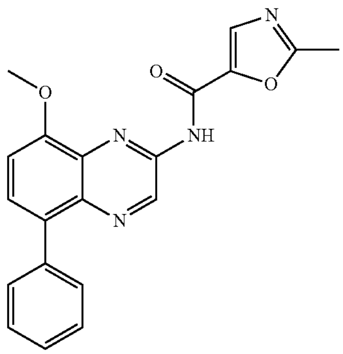 [SMILES: COc1ccc(-c2ccccc2)c2ncc(NC(=O)c3cnc(C)o3)nc12] | N-(8-methoxy-5-phenylquinoxalin-2-yl)-2-methyl-1,3-oxazole-5-carboxamide |
| 106 | 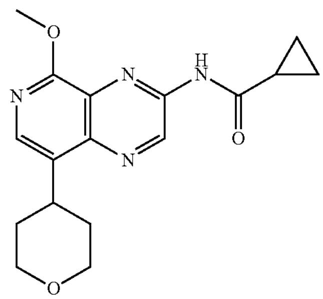 [SMILES: COc1ncc(C2CCOCC2)c2ncc(NC(=O)C3CC3)nc12] | Cyclopropanecarboxylic acid [5-methoxy-8-(tetrahydro-pyran-4-yl)-pyrido[3,4-b]pyrazin-3-yl]-amide |
| 107 | 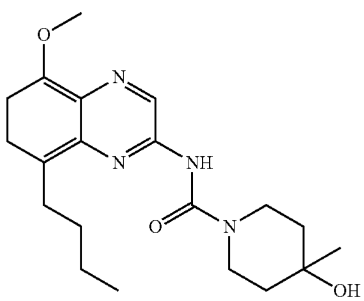 [SMILES: CCCCC1=c2nc(NC(=O)N3CCC(C)(O)CC3)cnc2=C(OC)CC1] | N-(8-butyl-5-methoxyquinoxalin-2-yl)-4-hydroxy-4-methylpiperidine-1-carboxamide |
| 108 | 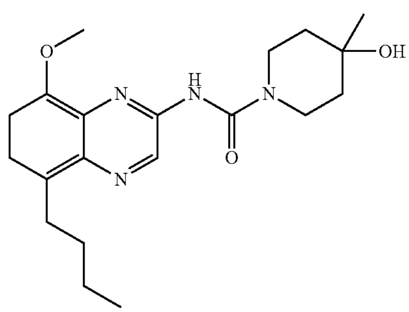 [SMILES: CCCCC1=c2ncc(NC(=O)N3CCC(C)(O)CC3)nc2=C(OC)CC1] | N-(5-butyl-8-methoxyquinoxalin-2-yl)-4-hydroxy-4-methylpiperidine-1-carboxamide |
| 109 | 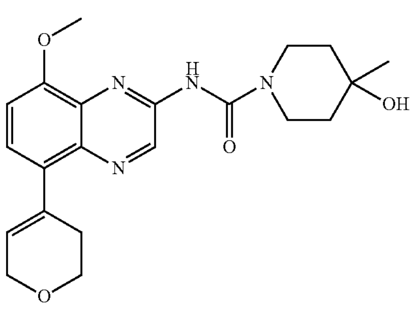 [SMILES: COc1ccc(C2=CCOCC2)c2ncc(NC(=O)N3CCC(C)(O)CC3)nc12] | N-[5-(3,6-dihydro-2H-pyran-4-yl)-8-methoxyquinoxalin-2-yl]-4-hydroxy-4-methylpiperidine-1-carboxamide |

TABLE 2-continued examples of compounds of the present invention

| No. | Structure | IUPAC-Name |
|---|---|---|
| 110 | 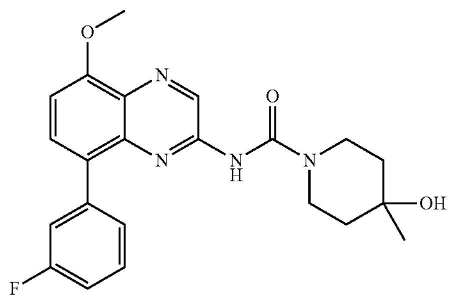 [SMILES: COc1ccc(-c2cccc(F)c2)c2nc(NC(=O)N3CCC(C)(O)CC3)cnc12] | N-[8-(3-fluorophenyl)-5-methoxyquinoxalin-2-yl]-4-hydroxy-4-methylplperidine-1-carboxamide |
| 111 | 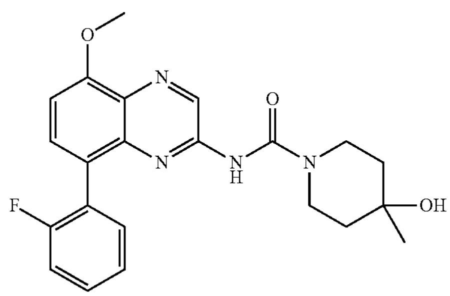 [SMILES: COc1ccc(-c2ccccc2F)c2nc(NC(=O)N3CCC(C)(O)CC3)cnc12] | N-[8-(2-fluorophenyl)-5-methoxyquinoxalin-2-yl]-4-hydroxy-4-methylpiperidine-1-carboxamide |
| 112 | 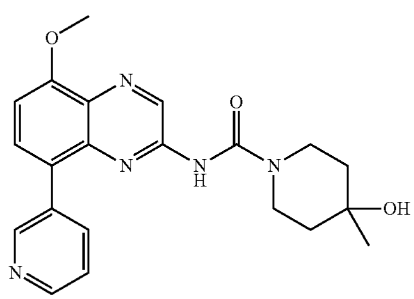 [SMILES: COc1ccc(-c2cccnc2)c2nc(NC(=O)N3CCC(C)(O)CC3)cnc12] | 4-hydroxy-N-[5-methoxy-8-(pyridin-3-yl)quinoxalin-2-yl)-4-methylpiperidine-1-carboxamide |
| 113 | 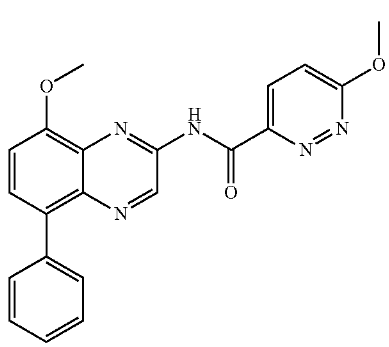 [SMILES: COc1ccc(C(=O)Nc2cnc3c(-c4ccccc4)ccc(OC)c3n2)nn1] | 6-methoxy-N-(8-methoxy-5-phenylquinoxalin-2-yl)pyridazine-3-carboxamide |

TABLE 2-continued examples of compounds of the present invention

| No. | Structure | IUPAC-Name |
|---|---|---|
| 114 | 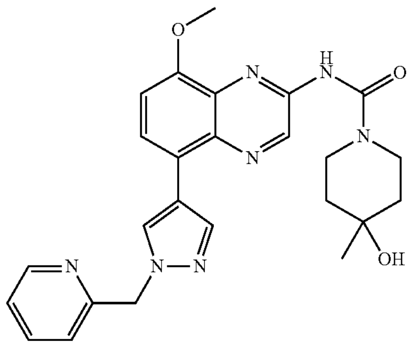 [SMILES: COc1ccc(-c2cnn(Cc3ccccn3)c2)c2ncc(NC(=O)N3CCC(C)(O)CC3)nc12] | 4-hydroxy-N-(8-methoxy-5-{1-[(pyridin-2-yl)methyl]-1H-pyrazol-4-yl}quinoxalin-2-yl)-4-methylpiperidine-1-carboxamide |
| 115 | 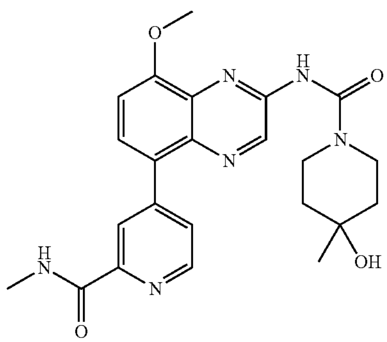 [SMILES: CNC(=O)c1cc(-c2ccc(OC)c3nc(NC(=O)N4CCC(C)(O)CC4)cnc23)ccn1] | 4-{2-[(4-hydroxy-4-methylpiperidine-1-carbonyl)amino]-8-methoxyquinoxalin-5-yl}-N-methylpyridine-2-carboxamide |
| 116 | 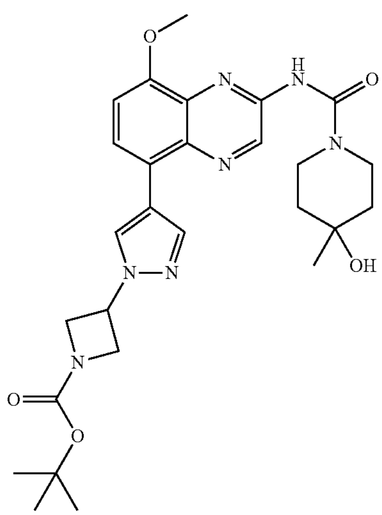 [SMILES: COc1ccc(-c2cnn(C3CN(C(=O)OC(C)(C)C)C3)c2)c2ncc(NC(=O)N3CCC(C)(O)CC3)nc12] | tert-butyl 3-(4-{2-[(4-hydroxy-4-methylpiperidine-1-carbonyl)amino]-8-methoxyquinoxalin-5-yl}-1H-pyrazol-1-yl)azetidine-1-carboxylate |
| 117 | 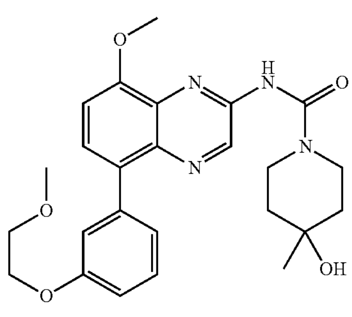 [SMILES: COCCOc1cccc(-c2ccc(OC)c3nc(NC(=O)N4CCC(C)(O)CC4)cnc23)c1] | 4-hydroxy-N-{8-methoxy-5-[3-(2-methoxyethoxy)phenyl]-quinoxalin-2-yl}-4-methylpiperidine-1-carboxamide |

TABLE 2-continued examples of compounds of the present invention

| No. | Structure | IUPAC-Name |
|---|---|---|
| 118 | 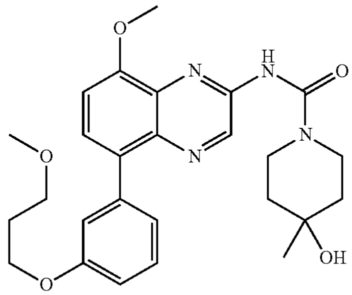 [SMILES: COCCCOc1cccc(-c2ccc(OC)c3nc(NC(=O)N4CCC(C)(O)CC4)cnc23)c1] | 4-hydroxy-N-(8-methoxy-5-{3-[(2-methoxyethoxy)methyl-]phenyl}quinoxalin-2-yl)-4-methylpiperidine-1-carboxamide |
| 119 | 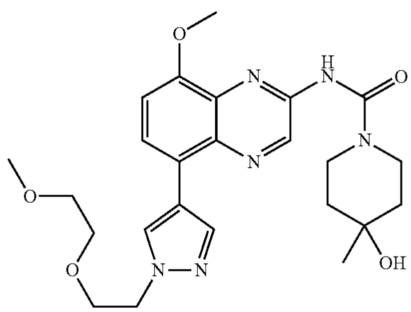 [SMILES: COCCOCCn1cc(-c2ccc(OC)c3nc(NC(=O)N4CCC(C)(O)CC4)cnc23)cn1] | 4-hydroxy-N-(8-methoxy-5-{1-[2-(2-methoxyethoxy)ethyl]-1H-pyrazol-4-yl}quinoxalin-2-yl)-4-methylpiperidine-1-carboxamide |
| 120 | 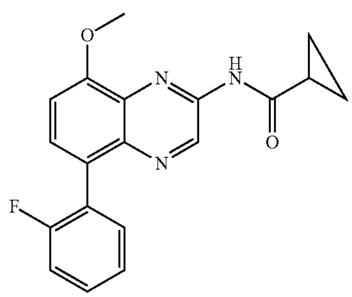 [SMILES: COc1ccc(-c2ccccc2F)c2ncc(NC(=O)C3CC3)nc12] | N-[5-(2-fluorophenyl)-8-methoxyquinoxalin-2-yl]cyclopropanecarboxamide |
| 121 | 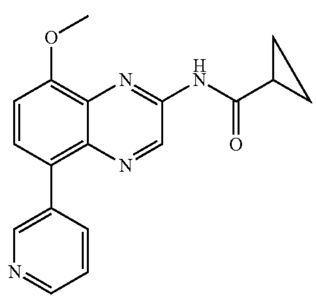 [SMILES: COc1ccc(-c2cccnc2)c2ncc(NC(=O)C3CC3)nc12] | N-[8-methoxy-5-(pyridin-3-yl)quinoxalin-2-yl]cyclopropanecarboxamide |
| 122 | 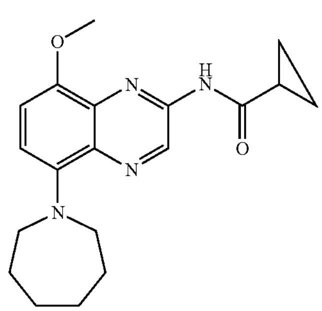 [SMILES: COc1ccc(N2CCCCCC2)c2ncc(NC(=O)C3CC3)nc12] | N-[5-(azepan-1-yl)-8-methoxyquinoxalin-2-yl]cyclopropanecarboxamide |

TABLE 2-continued examples of compounds of the present invention

| No. | Structure | IUPAC-Name |
|---|---|---|
| 123 | 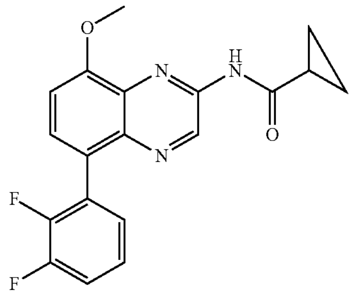 [SMILES: COc1ccc(-c2cccc(F)c2F)c2ncc(NC(=O)C3CC3)nc12] | N-[5-(2,3-difluorophenyl)-8-methoxyquinoxalin-2-yl]cyclopropanecarboxamide |
| 124 | 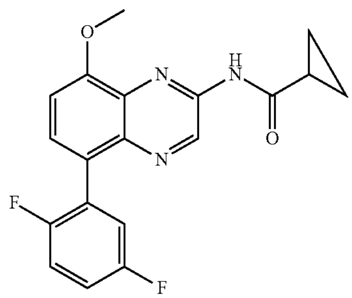 [SMILES: COc1ccc(-c2cc(F)ccc2F)c2ncc(NC(=O)C3CC3)nc12] | N-[5-(2,5-difluorophenyl)-8-methoxyquinoxalin-2-yl]cyclopropanecarboxamide |
| 125 | 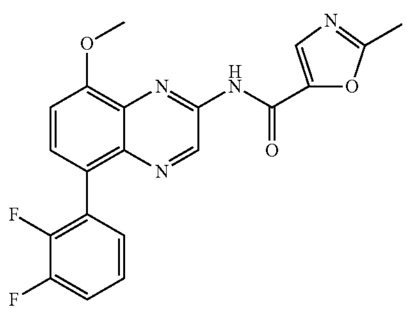 [SMILES: COc1ccc(-c2cccc(F)c2F)c2ncc(NC(=O)c3cnc(C)o3)nc12] | N-[5-(2,3-difluorophenyl)-8-methoxyquinoxalin-2-yl]-2-methyl-1,3-oxazole-5-carboxamide |
| 126 | 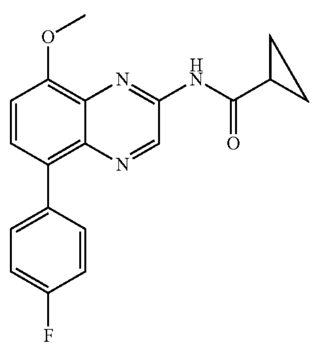 [SMILES: COc1ccc(-c2ccc(F)cc2)c2ncc(NC(=O)C3CC3)nc12] | N-[5-(4-fluorophenyl)-8-methoxyquinoxalin-2-yl]cyclopropanecarboxamide |
| 127 | 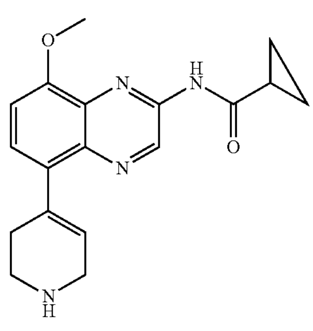 [SMILES: COc1ccc(C2=CCNCC2)c2ncc(NC(=O)C3CC3)nc12] | N-[8-methoxy-5-(1,2,3,6-tetrahydropyridin-4-yl)quinoxalin-2-yl]cyclopropanecarboxamide |

TABLE 2-continued examples of compounds of the present invention

| No. | Structure | IUPAC-Name |
|---|---|---|
| 128 | 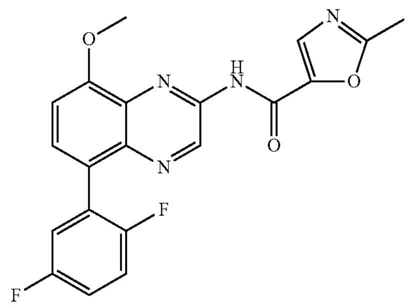 [SMILES: COc1ccc(-c2cc(F)ccc2F)c2ncc(NC(=O)c3cnc(C)o3)nc12] | N-[5-(2,5-difluorophenyl)-8-methoxyquinoxalin-2-yl]-2-methyl-1,3-oxazole-5-carboxamide |
| 129 | 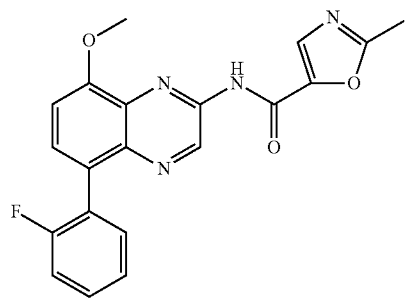 [SMILES: COc1ccc(-c2ccccc2F)c2ncc(NC(=O)c3cnc(C)o3)nc12] | N-[5-(2-fluorophenyl)-8-methoxyquinoxalin-2-yl]-2-methyl-1,3-oxazole-5-carboxamide |
| 130 | 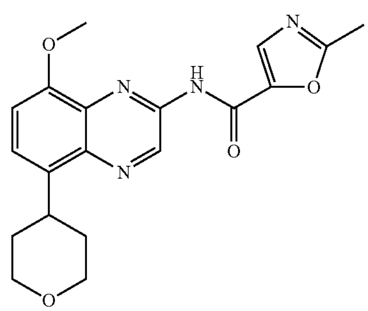 [SMILES: COc1ccc(C2CCOCC2)c2ncc(NC(=O)c3cnc(C)o3)nc12] | N-[8-methoxy-5-(oxan-4-yl)quinoxalin-2-yl]-2-methyl-1,3-oxazole-5-carboxamide |
| 131 | 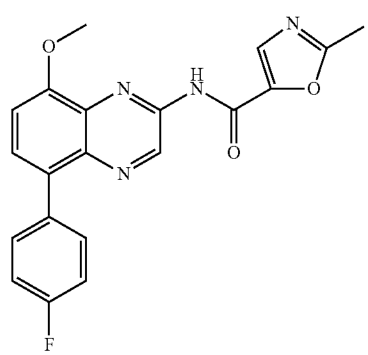 [SMILES: COc1ccc(-c2ccc(F)cc2)c2ncc(NC(=O)c3cnc(C)o3)nc12] | N-[5-(4-fluorophenyl)-8-methoxyquinoxalin-2-yl]-2-methyl-1,3-oxazole-5-carboxamide |

TABLE 2-continued examples of compounds of the present invention

| No. | Structure | IUPAC-Name |
| --- | --- | --- |
| 132 | 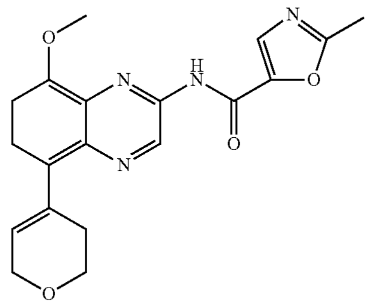 [SMILES: COC1=c2nc(NC(=O)c3cnc(C)o3)cnc2=C(C2=CCOCC2)CC1] | N-[5-(3,6-dihydro-2H-pyran-4-yl)-8-methoxyquinoxalin-2-yl]-2-methyl-1,3-oxazole-5-carboxamide |
| 133 | 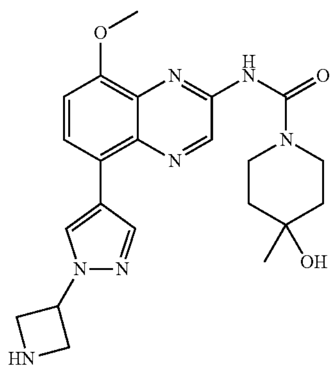 [SMILES: COc1ccc(-c2cnn(C3CNC3)c2)c2ncc(NC(=O)N3CCC(C)(O)CC3)nc12] | N-{5-[1-(azetidin-3-yl)-1H-pyrazol-4-yl]-8-methoxyquinoxalin-2-yl}-4-hydroxy-4-methylpiperidine-1-carboxamide |
| 134 | 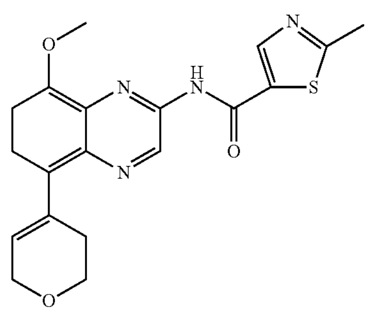 [SMILES: COC1=c2nc(NC(=O)c3cnc(C)s3)cnc2=C(C2=CCOCC2)CC1] | N-[5-(3,6-dihydro-2H-pyran-4-yl)-8-methoxyquinoxalin-2-yl]-2-methyl-1,3-thiazole-5-carboxamide |
| 135 | 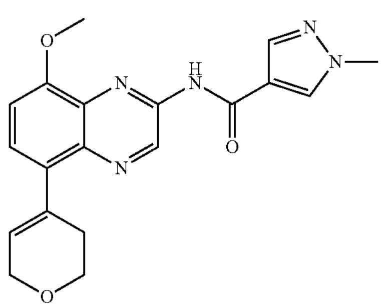 [SMILES: COc1ccc(C2=CCOCC2)c2ncc(NC(=O)c3cnn(C)c3)nc12] | N-[5-(3,6-dihydro-2H-pyran-4-yl)-8-methoxyquinoxalin-2-yl]-1-methyl-1H-pyrazole-4-carboxamide |

TABLE 2-continued examples of compounds of the present invention

| No. | Structure | IUPAC-Name |
|---|---|---|
| 136 | 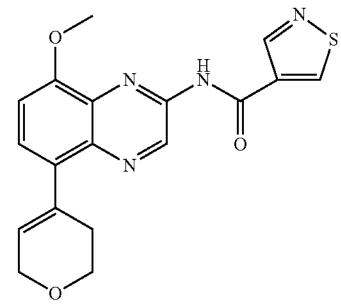 [SMILES: COc1ccc(C2=CCOCC2)c2ncc(NC(=O)c3cnsc3)nc12] | N-[5-(3,6-dihydro-2H-pyran-4-yl)-8-methoxyquinoxalin-2-yl]-1,2-thiazole-4-carboxamide |
| 137 | 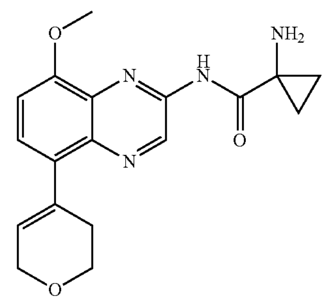 [SMILES: COc1ccc(C2=CCOCC2)c2ncc(NC(=O)C3(N)CC3)nc12] | 1-amino-N-[5-(3,6-dihydro-2H-pyran-4-yl)-8-methoxyquinoxalin-2-yl]cyclopropane-1-carboxamide |
| 138 | 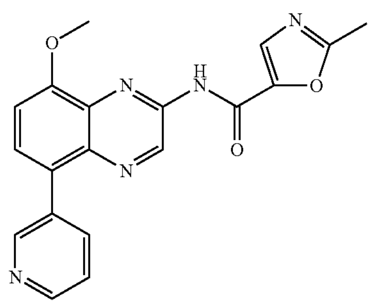 [SMILES: COc1ccc(-c2cccnc2)c2ncc(NC(=O)c3cnc(C)o3)nc12] | N-[8-methoxy-5-(pyridin-3-yl)quinoxalin-2-yl]-2-methyl-1,3-oxazole-5-carboxamide |
| 139 | 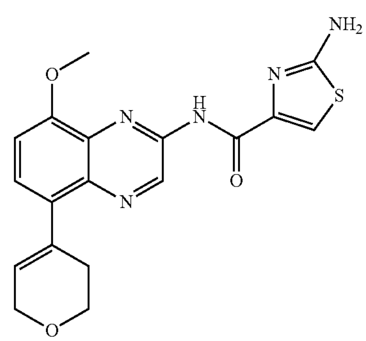 [SMILES: COc1ccc(C2=CCOCC2)c2ncc(NC(=O)c3csc(N)n3)nc12] | 2-amino-N-[5-(3,6-dihydro-2H-pyran-4-yl)-8-methoxyquinoxalin-2-yl]-1,3-thiazole-4-carboxamide |
| 140 | 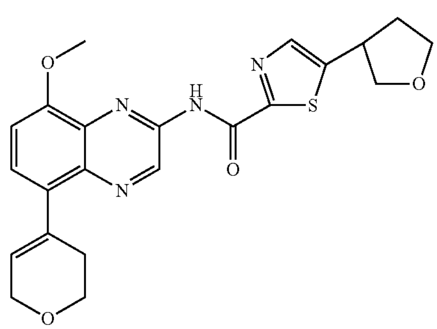 [SMILES: COc1ccc(C2=CCOCC2)c2ncc(NC(=O)c3ncc(C4CCOC4)s3)nc12] | N-[5-(3,6-dihydro-2H-pyran-4-yl)-8-methoxyquinoxalin-2-yl]-5-(oxolan-3-yl)-1,3-thiazole-2-carboxamlde |

TABLE 2-continued examples of compounds of the present invention

| No. | Structure | IUPAC-Name |
| --- | --- | --- |
| 141 | 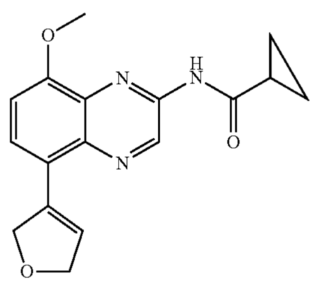 [SMILES: COc1ccc(C2=CCOC2)c2ncc(NC(=O)C3CC3)nc12] | N-[5-(2,5-dihydrofuran-3-yl)-8-methoxyquinoxalin-2-yl]cyclopropanecarboxamide |
| 142 | 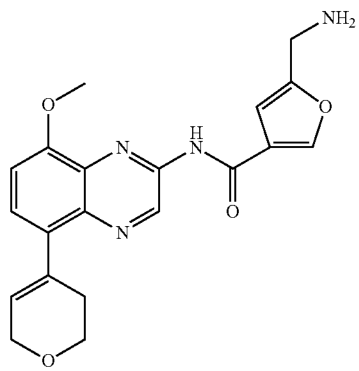 [SMILES: COc1ccc(C2=CCOCC2)c2ncc(NC(=O)c3coc(CN)c3)nc12] | 5-(aminomethyl)-N-[5-(3,6-dihydro-2H-pyran-4-yl)-8-methoxyquinoxalin-2-yl]furan-3-carboxamide |
| 143 | 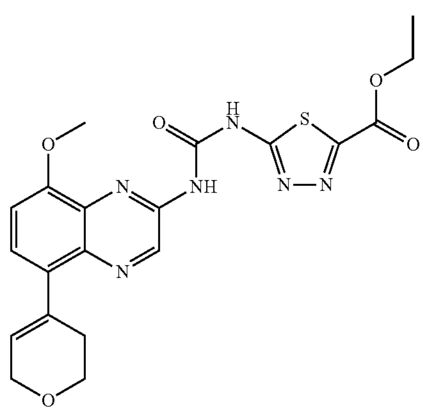 [SMILES: CCOC(=O)c1nnc(NC(=O)Nc2cnc3c(C4=CCOCC4)ccc(OC)c3n2)s1] | ethyl 5-({[5-(3,6-dihydro-2H-pyran-4-yl)-8-methoxyquinoxalin-2-yl]carbamoyl}amino)-1,3,4-thiadiazole-2-carboxylate |
| 144 | 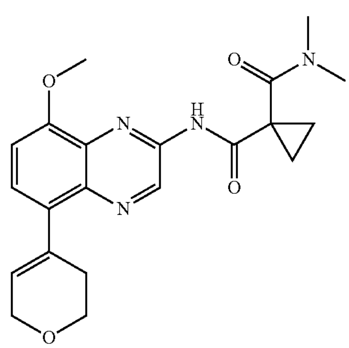 [SMILES: COc1ccc(C2=CCOCC2)c2ncc(NC(=O)C3(C(=O)N(C)C)CC3)nc12] | N'1-[5-(3,6-dihydro-2H-pyran-4-yl)-8-methoxyquinoxalin-2-yl]-N1,N1-dimethylcyclopropane-1,1-dicarboxamide |

TABLE 2-continued examples of compounds of the present invention

| No. | Structure | IUPAC-Name |
|---|---|---|
| 145 | 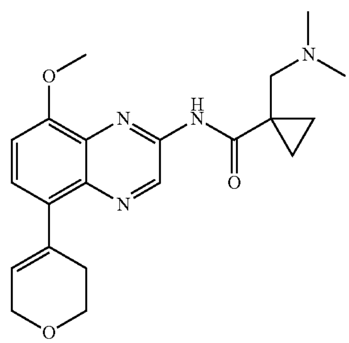 [SMILES: COc1ccc(C2=CCOCC2)c2ncc(NC(=O)C3(CN(C)C)CC3)nc12] | N-[5-(3,6-dihydro-2H-pyran-4-yl)-8-methoxyquinoxalin-2-yl]-1-[(dimethylamino)methyl]-cyclopropane-1-carboxamide |
| 146 | 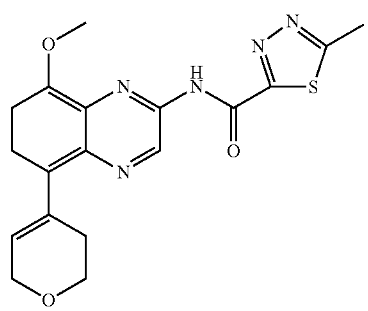 [SMILES: COC1=c2nc(NC(=O)c3nnc(C)s3)cnc2=C(C2=CCOCC2)CC1] | N-[5-(3,6-dihydro-2H-pyran-4-yl)-8-methoxyquinoxalin-2-yl]-5-methyl-1,3,4-thiadiazole-2-carboxamide |
| 147 | 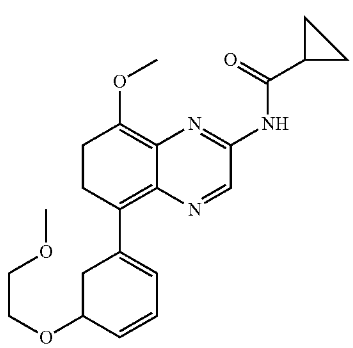 [SMILES: COCCOC1C=CC=C(C2=c3ncc(NC(=O)C4CC4)nc3=C(OC)CC2)C1] | N-{8-methoxy-5-[3-(2-methoxyethoxy)phenyl]quinoxalin-2-yl}cyclopropanecarboxamide |
| 148 | 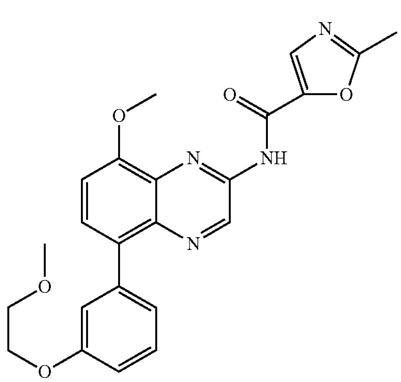 | N-{8-methoxy-5-[3-(2-methoxyethoxy)phenyl]quinoxalin-2-yl}-2-methyl-1,3-oxazole-5-carboxamide |

TABLE 2-continued examples of compounds of the present invention

| No. | Structure | IUPAC-Name |
|---|---|---|
| 149 | 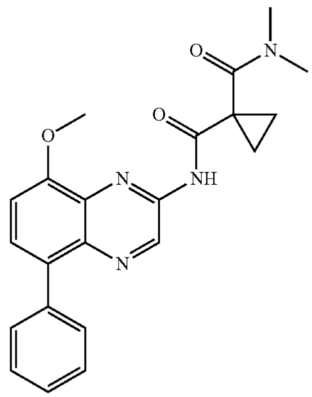 [SMILES: COc1ccc(-c2ccccc2)c2ncc(NC(=O)C3(C(=O)N(C)C)CC3)nc12] | N'1-(8-methoxy-5-phenylquinoxalin-2-yl)-N1,N1-dimethylcyclopropane-1,1-dicarboxamide |
| 150 | 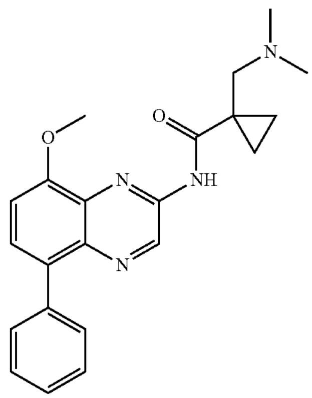 [SMILES: COc1ccc(-c2ccccc2)c2ncc(NC(=O)C3(CN(C)C)CC3)nc12] | 1-[(dimethylamino)methyl]-N-(8-methoxy-5-phenylquinoxalin-2-yl)cyclopropane-1-carboxamide |
| 151 | 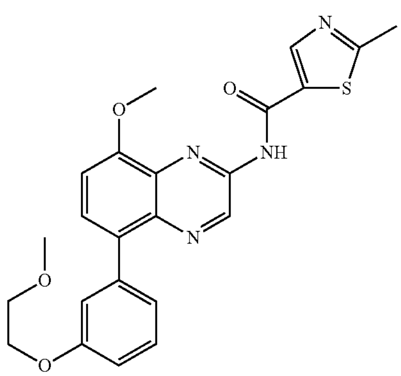 [SMILES: COCCOc1cccc(-c2ccc(OC)c3nc(NC(=O)c4cnc(C)s4)cnc23)c1] | N-{8-methoxy-5-[3-(2-methoxyethoxy)phenyl]quinoxalin-2-yl}-2-methyl-1,3-thiazole-5-carboxamide |
| 152 | 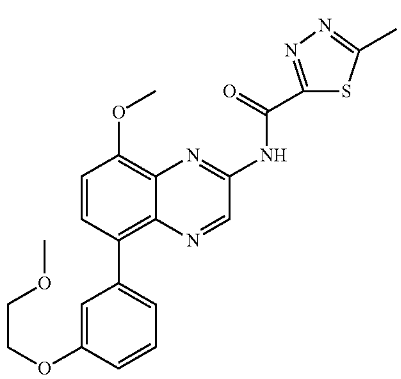 [SMILES: COCCOc1cccc(-c2ccc(OC)c3nc(NC(=O)c4nnc(C)s4)cnc23)c1] | N-{8-methoxy-5-[3-(2-methoxyethoxy)phenyl]quinoxalin-2-yl}-5-methyl-1,3,4-thiadiazole-2-carboxamide |

TABLE 2-continued examples of compounds of the present invention

| No. | Structure | IUPAC-Name |
|---|---|---|
| 153 | 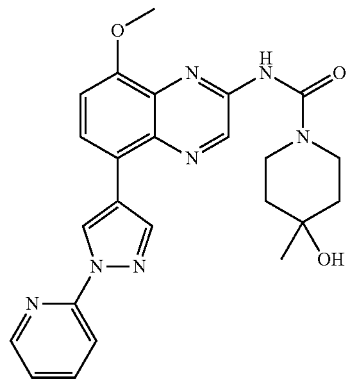 [SMILES: COc1ccc(-c2cnn(-c3ccccn3)c2)c2ncc(NC(=O)N3CCC(C)(O)CC3)nc12] | 4-hydroxy-N-{8-methoxy-5-[1-(pyridin-2-yl)-1H-pyrazol-4-yl]quinoxalin-2-yl}-4-methylpiperidine-1-carboxamide |
| 154 | 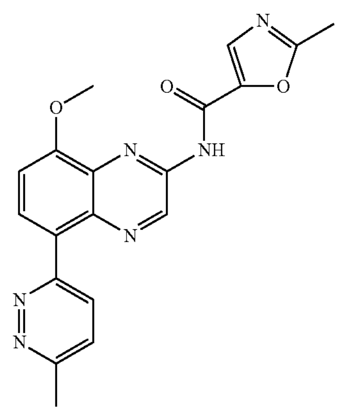 [SMILES: COc1ccc(-c2ccc(C)nn2)c2ncc(NC(=O)c3cnc(C)o3)nc12] | N-[8-methoxy-5-(6-methylpyridazin-3-yl)quinoxalin-2-yl]-2-methyl-1,3-oxazole-5-carboxamide |
| 155 | 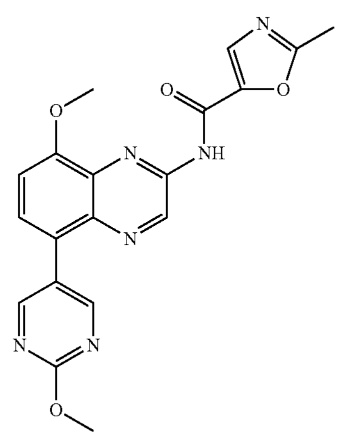 [SMILES: COc1ncc(-c2ccc(OC)c3nc(NC(=O)c4cnc(C)o4)cnc23)cn1] | N-[8-methoxy-5-(2-methoxypyrimidin-5-yl)quinoxalin-2-yl]-2-methyl-1,3-oxazole-5-carboxamide |

TABLE 2-continued examples of compounds of the present invention

| No. | Structure | IUPAC-Name |
| --- | --- | --- |
| 156 | 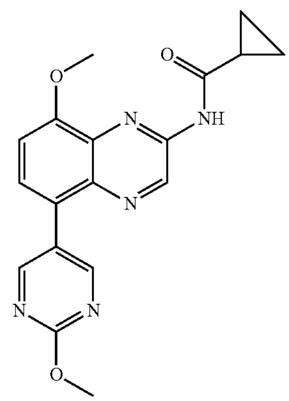 [SMILES: COc1ncc(-c2ccc(OC)c3nc(NC(=O)C4CC4)cnc23)cn1] | N-[8-methoxy-5-(2-methoxypyrimidin-5-yl)quinoxalin-2-yl]cyclopropanecarboxamide |
| 157 | 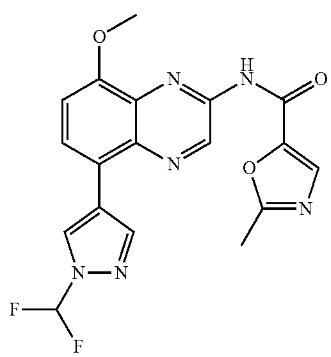 [SMILES: COc1ccc(-c2cnn(C(F)F)c2)c2ncc(NC(=O)c3cnc(C)o3)nc12] | N-{5-[1-(difluoromethyl)-1H-pyrazol-4-yl]-8-methoxyquinoxalin-2-yl}-2-methyl-1,3-oxazole-5-carboxamide |
| 158 | 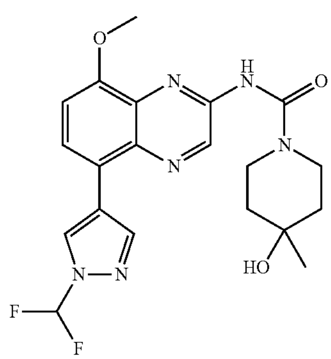 [SMILES: COc1ccc(-c2cnn(C(F)F)c2)c2ncc(NC(=O)N3CCC(C)(O)CC3)nc12] | N-{5-[1-(difluoromethyl)-1H-pyrazol-4-yl]-8-methoxyquinoxalin-2-yl}-4-hydroxy-4-methylpiperidine-1-carboxamide |
| 159 | 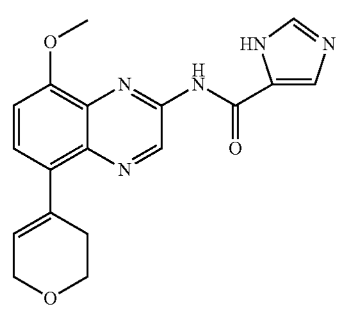 [SMILES: COc1ccc(C2=CCOCC2)c2ncc(NC(=O)c3cnc[nH]3)nc12] | N-[5-(3,6-dihydro-2H-pyran-4-yl)-8-methoxyquinoxalin-2-yl]-1H-imidazole-5-carboxamide |

TABLE 2-continued examples of compounds of the present invention

| No. | Structure | IUPAC-Name |
|---|---|---|
| 160 | 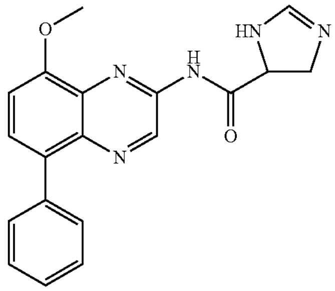 [SMILES: COc1ccc(-c2ccccc2)c2ncc(NC(=O)C3CN=CN3)nc12] | N-(8-methoxy-5-phenylquinoxalin-2-yl)-1H-imidazole-5-carboxamide |
| 161 | 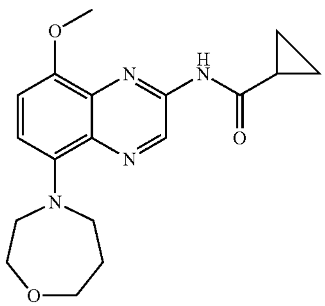 [SMILES: COc1ccc(N2CCCOCC2)c2ncc(NC(=O)C3CC3)nc12] | N-[8-methoxy-5-(1,4-oxazepan-4-yl)quinoxalin-2-yl]cyclopropanecarboxamide |

TABLE 3

NMR profiles of the compounds of the present invention

| No. | MW | [M + H] + 1 |
|---|---|---|
| 1 | 251.29 | 252 |
| 2 | 392.46 | 393 |
| 3 | 255.28 | 256 |
| 4 | 441.49 | 442 |
| 5 | 400.48 | 401 |
| 6 | 396.45 | 397 |
| 7 | 401.46 | 402 |
| 8 | 441.49 | 442 |
| 9 | 421.50 | 422 |
| 10 | 424.50 | 425 |
| 11 | 408.46 | 409 |
| 12 | 420.51 | 422 |
| 13 | 412.49 | 413 |
| 14 | 393.44 | 394 |
| 15 | 386.45 | 387 |
| 16 | 368.39 | 369 |
| 17 | 414.50 | 416 |
| 18 | 432.50 | 433 |
| 19 | 395.42 | 396 |
| 20 | 411.46 | 412 |
| 21 | 416.48 | 417 |
| 22 | 378.43 | 379 |
| 23 | 406.48 | 407 |
| 24 | 418.49 | 419 |
| 25 | 404.47 | 405 |
| 26 | 424.48 | 425 |
| 27 | 393.44 | 394 |
| 28 | 379.42 | 380 |
| 29 | 407.47 | 408 |
| 30 | 426.51 | 428 |
| 31 | 301.34 | 302 |
| 32 | 355.31 | 356 |
| 33 | 413.48 | 414 |
| 34 | 417.47 | 418 |
| 35 | 400.44 | 401 |
| 36 | 404.43 | 405 |
| 37 | 381.39 | 382 |
| 38 | 259.31 | 260 |
| 39 | 386.45 | 387 |
| 40 | 386.45 | 387 |
| 41 | 406.48 | 407 |
| 42 | 403.44 | 404 |
| 43 | 360.37 | 361 |
| 44 | 359.39 | 360 |
| 45 | 319.36 | 320 |
| 46 | 359.39 | 360 |
| 47 | 362.41 | 363 |
| 48 | 376.44 | 377 |
| 49 | 346.35 | 347 |
| 50 | 410.45 | 411 |
| 51 | 401.46 | 402 |
| 52 | 327.38 | 328 |
| 53 | 408.46 | 409 |
| 54 | 419.44 | 420 |
| 55 | 404.43 | 405 |
| 56 | 412.45 | 413 |
| 57 | 347.33 | 348 |
| 58 | 414.51 | 416 |
| 59 | 387.44 | 388 |
| 60 | 410.45 | 411 |
| 61 | 410.45 | 411 |
| 62 | 410.45 | 411 |
| 63 | 441.53 | 443 |
| 64 | 393.45 | 394 |
| 65 | 413.52 | 415 |
| 66 | 393.45 | 394 |
| 67 | 355.35 | 356 |
| 68 | 367.41 | 368 |
| 69 | 368.39 | 369 |
| 70 | 394.43 | 395 |
| 71 | 412.45 | 413 |
| 72 | 368.40 | 369 |
| 73 | 352.39 | 353 |
| 74 | 363.44 | 364 |

TABLE 3-continued

NMR profiles of the compounds of the present invention

| No. | MW | [M + H] + 1 |
|---|---|---|
| 75 | 345.40 | 346 |
| 76 | 367.41 | 368 |
| 77 | 370.43 | 371 |
| 78 | 384.46 | 385 |
| 79 | 354.37 | 355 |
| 80 | 417.49 | 418 |
| 81 | 404.43 | 405 |
| 82 | 342.40 | 343 |
| 83 | 334.38 | 335 |
| 84 | 396.41 | 397 |
| 85 | 409.47 | 410 |
| 86 | 337.38 | 338 |
| 87 | 355.42 | 356 |
| 88 | 344.37 | 345 |
| 89 | 360.38 | 361 |
| 90 | 404.43 | 405 |
| 91 | 386.41 | 387 |
| 92 | 360.37 | 361 |
| 93 | 359.39 | 360 |
| 94 | 373.37 | 374 |
| 95 | 372.47 | 373 |
| 96 | 398.51 | 400 |
| 97 | 400.48 | 401 |
| 98 | 407.47 | 408 |
| 99 | 393.45 | 394 |
| 100 | 406.49 | 407 |
| 101 | 345.36 | 346 |
| 102 | 320.35 | 321 |
| 103 | 425.49 | 426 |
| 104 | 415.49 | 416 |
| 105 | 360.37 | 361 |
| 106 | 328.37 | 329 |
| 107 | 372.47 | 373 |
| 108 | 372.47 | 373 |
| 109 | 398.46 | 399 |
| 110 | 410.45 | 411 |
| 111 | 410.45 | 411 |
| 112 | 393.44 | 394 |
| 113 | 387.40 | 388 |
| 114 | 473.53 | 475 |
| 115 | 450.50 | 451 |
| 116 | 537.62 | 539 |
| 117 | 466.54 | 468 |
| 118 | 480.56 | 482 |
| 119 | 484.55 | 486 |
| 120 | 337.35 | 338 |
| 121 | 320.35 | 321 |
| 122 | 340.42 | 341 |
| 123 | 355.34 | 356 |
| 124 | 355.34 | 356 |
| 125 | 396.35 | 397 |
| 126 | 337.35 | 338 |
| 127 | 324.38 | 325 |
| 128 | 396.35 | 397 |
| 129 | 378.36 | 379 |
| 130 | 368.39 | 369 |
| 131 | 378.36 | 379 |
| 132 | 366.38 | 367 |
| 133 | 437.50 | 439 |
| 134 | 382.44 | 383 |
| 135 | 365.39 | 366 |
| 136 | 368.42 | 369 |
| 137 | 340.38 | 341 |
| 138 | 361.36 | 362 |
| 139 | 383.43 | 384 |
| 140 | 438.51 | 440 |
| 141 | 311.34 | 312 |
| 142 | 380.40 | 381 |
| 143 | 456.48 | 457 |
| 144 | 396.44 | 397 |
| 145 | 382.46 | 383 |
| 146 | 383.43 | 384 |
| 147 | 393.44 | 394 |
| 148 | 434.45 | 435 |
| 149 | 390.44 | 391 |
| 150 | 376.46 | 377 |
| 151 | 450.52 | 452 |
| 152 | 451.50 | 453 |
| 153 | 459.51 | 461 |
| 154 | 376.37 | 377 |
| 155 | 392.37 | 393 |
| 156 | 351.36 | 352 |
| 157 | 400.34 | 401 |
| 158 | 432.43 | 433 |
| 159 | 351.36 | 352 |
| 160 | 345.36 | 346 |
| 161 | 342.40 | 343 |

The Nos. recited herein corresponds to the numbering of the compounds disclosed in table 2

| No. | NMR |
|---|---|
| 2 | 1H NMR (400 MHz, DMSO-d6) ppm = 9.94 (s, 1H), 9.19 (s, 1H), 7.61-7.55 (m, 3H), 7.49-7.33 (m, 3H), 7.31-7.26 (m, 1H), 4.33 (s, 1H), 3.99 (s, 3H), 3.85-3.77 (m, 2H), 3.35-3.23 (m, 2H), 1.54-1.45 (m, 4H), 1.16 (s, 3H). |
| 4 | 1H NMR (500 MHz, DMSO-d6) ppm = 11.79 (s, 1H), 9.61 (s, 1H), 8.27-8.25 (m, 1H), 7.72 (d, J = 8.2 Hz, 1H), 7.67-7.64 (m, 1H), 7.64-7.61 (m, 2H), 7.50-7.46 (m, 2H), 7.41-7.37 (m, 2H), 7.27 (dd, J = 5.5, 1.4 Hz, 1H), 4.03 (s, 3H), 3.78-3.74 (m, 4H), 3.67-3.63 (m, 4H). |
| 6 | 1H NMR (500 MHz, DMSO-d6) ppm = 10.28-9.85 (m, 1H), 9.29 (s, 1H), 8.42 (s, 1H), 8.06 (s, 1H), 7.78 (d, J = 8.3 Hz, 1H), 7.23 (d, J = 8.4 Hz, 1H), 3.96 (s, 3H), 3.92 (s, 3H), 3.86-3.80 (m, 2H), 3.34-3.24 (m, 2H), 1.53-1.44 (m, 4H), 1.16 (s, 3H). |
| 7 | 1H NMR (400 MHz, DMSO-d6) ppm = 10.15-9.94 (m, 1H), 9.25 (s, 1H), 7.46-7.35 (m, 1H), 7.22-7.16 (m, 1H), 4.00-3.89 (m, 7H), 3.87-3.76 (m, 2H), 3.53-3.36 (m, 4H), 3.35-3.23 (m, 2H), 1.54-1.43 (m, 4H), 1.16 (s, 3H). |
| 8 | 1H NMR (500 MHz, DMSO-d6) ppm = 11.48 (s, 1H), 9.58 (s, 1H), 8.88-8.87 (m, 1H), 8.28 (dd, J = 9.2, 2.5 Hz, 1H), 7.69 (d, J = 8.2 Hz, 1H), 7.64-7.61 (m, 2H), 7.50-7.46 (m, 2H), 7.42-7.36 (m, 2H), 7.01 (d, J = 9.2 Hz, 1H), 4.03 (s, 3H), 3.74-3.71 (m, 4H), 3.69-3.65 (m, 4H). |
| 9 | 1H NMR (300 MHz, DMSO-d6) 11.65 (s, 1H), 9.75 (s, 1H), 8.38-7.92 (m, 3H), 7.42 (d, J = 7.9 Hz, 2H), 4.03 (s, 3H), 4.01-3.88 (m, 2H), 3.76-3.61 (m, 1H), 3.57-3.41 (m, 4H), 2.14 (s, 6H), 1.98-1.64 (m, 4H). |
| 10 | 1H NMR (500 MHz, DMSO-d6) ppm = 9.98-9.85 (m, 1H), 9.21 (s, 1H), 7.41 (d, J = 8.2 Hz, 1H), 7.17 (d, J = 8.2 Hz, 1H), 4.00-3.94 (m, 2H), 3.93 (s, 3H), 3.92-3.85 (m, 3H), 3.55 (td, J = 11.5, 2.4 Hz, 2H), 3.23-3.15 (m, 2H), 2.82 (t, J = 2.6 Hz, 1H), 2.33 (d, J = 2.7 Hz, 2H), 1.84-1.71 (m, 4H), 1.66 (td, J = 12.8, 4.5 Hz, 2H), 1.57-1.51 (m, 2H). |
| 12 | 1H NMR (500 MHz, DMSO-d6) ppm = 11.61 (s, 1H), 10.49-10.42 (m, 1H), 9.62 (s, 1H), 8.22-8.19 (m, 2H), 7.73-7.70 (m, 2H), 7.55 (d, J = 8.2 Hz, 1H), 7.26 (d, J = 8.3 Hz, 1H), 4.38 (d, J = 5.4 Hz, 2H), 4.03-3.98 (m, 2H), 3.97 (s, 3H), 3.98-3.91 (m, 1H), 3.61-3.54 (m, 2H), 2.74 (d, J = 4.8 Hz, 6H), 1.89-1.75 (m, 4H). |
| 13 | 1H NMR (400 MHz, DMSO-d6) ppm = 9.64-9.44 (m, 1H), 9.36 (s, 1H), 7.42 (d, J = 8.1 Hz, 1H), 7.18 (d, J = 8.2 Hz, 1H), 4.01-3.95 (m, 2H), 3.93 (s, 3H), 3.92-3.84 (m, 1H), 3.83-3.77 (m, 2H), 3.61-3.46 (m, 8H), 1.95-1.70 (m, 8H). |
| 14 | 1H NMR (500 MHz, DMSO-d6) ppm = 10.14 (s, 1H), 9.30 (s, 1H), 8.97-8.94 (m, 2H), 8.42-8.39 (m, 2H), |

| No. | NMR |
|---|---|
|  | 7.97 (d, J = 8.3 Hz, 1H), 7.43 (d, J = 8.4 Hz, 1H), 4.06 (s, 3H), 3.82 (dt, J = 13.4, 4.3 Hz, 2H), 3.34-3.26 (m, 2H), 1.54-1.44 (m, 4H), 1.16 (s, 3H). |
| 15 | 1H NMR (400 MHz, DMSO-d6) ppm = 9.55-9.45 (m, 1H), 9.36 (s, 1H), 8.53-8.36 (m, 1H), 7.41 (d, J = 8.1 Hz, 1H), 7.17 (d, J = 8.2 Hz, 1H), 4.01-3.95 (m, 2H), 3.93 (s, 3H), 3.92-3.85 (m, 1H), 3.59-3.40 (m, 6H), 1.88-1.71 (m, 6H), 1.31 (s, 3H). |
| 16 | 1H NMR (400 MHz, DMSO-d6) ppm = 10.57 (s, 1H), 9.63 (s, 1H), 8.87 (s, 1H), 7.54 (d, J = 8.2 Hz, 1H), 7.25 (d, J = 8.3 Hz, 1H), 4.02-3.96 (m, 2H), 3.96 (s, 3H), 3.95-3.88 (m, 1H), 3.56 (td, J = 11.3, 2.6 Hz, 2H), 2.52 (s, 3H), 1.88-1.72 (m, 4H). |
| 17 | 1H NMR (700 MHz, DMSO-d6) ppm = 9.95-9.86 (m, 1H), 9.21 (s, 1H), 7.41 (d, J = 8.1 Hz, 1H), 7.17 (d, J = 8.3 Hz, 1H), 3.99-3.96 (m, 2H), 3.92 (s, 3H), 3.91-3.86 (m, 1H), 3.77-3.73 (m, 2H), 3.56-3.52 (m, 2H), 3.30-3.25 (m, 2H), 3.19 (s, 2H), 1.83-1.76 (m, 2H), 1.77-1.71 (m, 2H), 1.50-1.45 (m, 2H), 1.25-1.21 (m, 2H), 0.92 (m, 3H). |
| 18 | 1H NMR (500 MHz, DMSO-d6) ppm = 10.13 (s, 1H), 9.46 (s, 1H), 7.42 (d, J = 8.1 Hz, 1H), 7.18 (d, J = 8.2 Hz, 1H), 4.47 (s, 4H), 4.33-4.28 (m, 4H), 4.00-3.96 (m, 2H), 3.93 (s, 3H), 3.92-3.86 (m, 1H), 3.55 (td, J = 11.5, 2.4 Hz, 2H), 1.84-1.71 (m, 4H). |
| 19 | 1H NMR (400 MHz, DMSO-d6) ppm = 11.06 (s, 1H), 9.70 (s, 1H), 8.30 (d, J = 9.1 Hz, 1H), 7.57 (d, J = 8.2 Hz, 1H), 7.49 (d, J = 9.2 Hz, 1H), 7.28 (d, J = 8.3 Hz, 1H), 4.18 (s, 3H), 4.03-3.98 (m, 2H), 3.98 (s, 3H), 3.97-3.90 (m, 1H), 3.61-3.53 (m, 2H), 1.89-1.74 (m, 4H). |
| 20 | 1H NMR (500 MHz, DMSO-d6) ppm = 11.20 (s, 1H), 9.65 (s, 1H), 8.58-8.57 (m, 1H), 8.24-8.23 (m, 1H), 7.51 (d, J = 8.2 Hz, 1H), 7.24 (d, J = 8.2 Hz, 1H), 4.33 (t, J = 5.2 Hz, 2H), 4.02-3.97 (m, 2H), 3.96 (s, 3H), 3.96-3.90 (m, 1H), 3.72 (t, J = 5.2 Hz, 2H), 3.56 (td, J = 11.5, 2.5 Hz, 2H), 3.26 (s, 3H), 1.87-1.73 (m, 4H). |
| 21 | 1H NMR (400 MHz, DMSO-d6) ppm = 9.98 (s, 1H), 9.20 (s, 1H), 7.61-7.56 (m, 3H), 7.48-7.43 (m, 2H), 7.39-7.34 (m, 1H), 7.29 (d, J = 8.3 Hz, 1H), 4.64 (s, 1H), 3.99 (s, 3H), 4.00-3.92 (m, 1H), 3.24-3.14 (m, 2H), 2.82 (t, J = 2.6 Hz, 1H), 2.33 (d, J = 2.7 Hz, 2H), 1.67 (td, J = 12.7, 4.4 Hz, 2H), 1.57-1.51 (m, 2H). |
| 22 | 1H NMR (400 MHz, DMSO-d6) ppm = 9.55 (s, 1H), 9.34 (s, 1H), 7.60-7.55 (m, 3H), 7.48-7.42 (m, 2H), 7.39-7.34 (m, 1H), 7.29 (d, J = 8.2 Hz, 1H), 4.80 (s, 1H), 3.99 (s, 3H), 3.79-3.29 (m, 4H), 1.91-1.75 (m, 2H), 1.31 (s, 3H). |
| 23 | 1H NMR (400 MHz, DMSO-d6) ppm = 9.92 (s, 1H), 9.20 (s, 1H), 7.61-7.55 (m, 3H), 7.48-7.42 (m, 2H), 7.39-7.34 (m, 1H), 7.29 (d, J = 8.3 Hz, 1H), 4.59-4.46 (m, 1H), 3.99 (s, 3H), 3.75 (dt, J = 13.5, 4.8 Hz, 2H), 3.33-3.24 (m, 2H), 3.19 (s, 2H), 1.52-1.43 (m, 2H), 1.27-1.20 (m, 2H), 0.92 (s, 3H). |
| 24 | 1H NMR (500 MHz, DMSO-d6) ppm = 9.62 (s, 1H), 9.35 (s, 1H), 7.60-7.57 (m, 3H), 7.48-7.43 (m, 2H), 7.39-7.35 (m, 1H), 7.30 (d, J = 8.3 Hz, 1H), 3.99 (s, 3H), 3.68-3.41 (m, 8H), 1.87-1.73 (m, 2H), 1.54-1.49 (m, 4H). |
| 25 | 1H NMR (500 MHz, DMSO-d6) ppm = 9.69 (s, 1H), 9.33 (s, 1H), 7.60-7.57 (m, 3H), 7.48-7.43 (m, 2H), 7.39-7.35 (m, 1H), 7.30 (d, J = 8.2 Hz, 1H), 3.99 (s, 3H), 3.84-3.76 (m, 3H), 3.74-3.40 (m, 6H), 1.97-1.82 (m, 4H). |
| 26 | 1H NMR (500 MHz, DMSO-d6) ppm = 10.27 (s, 1H), 9.44 (s, 1H) 7.61-7.57 (m, 3H), 7.48-7.44 (m, 2H), 7.39-7.35 (m, 1H), 7.31 (d, J = 8.2 Hz, 1H), 4.48 (s, 4H), 4.37-4.24 (m, 4H), 3.99 (s, 3H). |
| 27 | 1H NMR (400 MHz, DMSO-d6)10.23 (s, 1H), 9.38 (s, 1H), 8.19 (s, 1H), 7.66-7.60 (m, 2H), 7.53-7.46 (m, 2H), 7.45-7.39 (m, 1H), 4.37 (s, 1H), 4.10 (s, 3H), 3.90-3.75 (m, 2H), 3.31-3.22 (m, 2H), 1.54-1.43 (m, 4H), 1.16 (s, 3H). |
| 28 | 1H NMR (400 MHz, DMSO-d6) 9.88 (s, 1H), 9.53 (s, 1H), 8.20 (s, 1H), 7.68-7.62 (m, 2H), 7.53-7.47 (m, 2H), 7.46-7.39 (m, 1H), 4.84 (s, 1H), 4.11 (s, 3H), 3.83-3.36 (m, 4H), 2.01-1.73 (m, 2H), 1.32 (s, 3H). |
| 29 | 1H NMR (400 MHz, DMSO-d6)10.24 (s, 1H), 9.39 (s, 1H), 8.20 (s, 1H), 7.70-7.61 (m, 2H), 7.53-7.47 (m, 2H), 7.45-7.39 (m, 1H), 4.57 (t, J = 5.4 Hz, 1H), 4.10 (s, 3H), 3.76 (dt, J = 13.5, 4.9 Hz, 2H), 3.31-3.24 (m, 1H), 3.20 (d, J = 5.5 Hz, 2H), 1.57-1.37 (m, 2H), 1.28-1.12 (m, 2H), 0.93 (s, 3H). |
| 30 | 1H NMR (400 MHz, DMSO-d6) ppm = 9.65-9.51 (m, 1H), 9.38 (s, 1H), 7.42 (d, J = 8.2 Hz, 1H), 7.18 (d, J = 8.1 Hz, 1H), 4.01-3.96 (m, 2H), 3.93 (s, 3H), 3.89 (tt, J = 11.8, 3.9 Hz, 1H), 3.66-3.62 (m, 2H), 3.57-3.52 (m, 4H), 3.67-3.27 (m, 4H), 1.87-1.76 (m, 4H), 1.76-1.71 (m, 2H), 1.55-1.49 (m, 4H). |
| 31 | 1H NMR (400 MHz, DMSO-d6) ppm = 11.24 (s, 1H), 9.62 (s, 1H), 7.48 (d, J = 8.2 Hz, 1H), 7.21 (d, J = 8.2 Hz, 1H), 4.01-3.96 (m, 2H), 3.94 (s, 3H), 3.93-3.86 (m, 1H), 3.55 (td, J = 11.4, 2.7 Hz, 2H), 2.18 (s, 3H), 1.86-1.71 (m, 4H). |
| 32 | 1H NMR (400 MHz, DMSO-d6) ppm = 8.52 (s, 1H), 8.08-7.69 (m, 1H), 7.27 (d, J = 8.3 Hz, 1H), 7.21 (d, J = 8.3 Hz, 1H), 4.00-3.95 (m, 2H), 3.94 (s, 3H), 3.84-3.75 (m, 1H), 3.51 (td, J = 11.6, 2.2 Hz, 2H), 1.84-1.73 (m, 2H), 1.72-1.65 (m, 2H). |
| 33 | 1H NMR (400 MHz, DMSO-d6) ppm = 11.44 (s, 1H), 9.61 (s, 1H), 8.34 (s, 1H), 8.05-8.00 (m, 2H), 7.76-7.72 (m, 2H), 7.52-7.39 (m, 6H), 4.15 (s, 3H), 3.52 (d, J = 5.1 Hz, 2H), 2.20 (s, 6H). |
| 34 | 1H NMR (400 MHz, DMSO-d6) ppm = 9.39 (s, 1H), 8.20 (s, 1H), 7.67-7.60 (m, 2H), 7.53-7.46 (m, 2H), 7.46-7.38 (m, 1H), 4.67 (s, 1H), 4.11 (s, 3H), 4.05-3.87 (m, 2H), 3.20 (t, J = 12.4 Hz, 2H), 2.85 (t, J = 2.6 Hz, 1H), 2.33 (d, J = 2.7 Hz, 2H), 1.67 (td, J = 12.4, 11.4, 4.0 Hz, 2H), 1.55 (d, J = 13.2 Hz, 2H). |
| 35 | 1H NMR (400 MHz, DMSO-d6) ppm = 11.77 (d, J = 1.6 Hz, 1H), 9.78 (d, J = 0.8 Hz, 1H), 8.30 (d, J = 1.6 Hz, 1H), 8.12 (d, J = 8.0 Hz, 2H), 7.68 (dt, J = 8.2, 1.2 Hz, 2H), 7.54-7.42 (m, 5H), 4.53 (s, 2H), 4.14 (d, J = 1.1 Hz, 3H), 3.36 (s, 3H). |
| 36 | 1H NMR (400 MHz, DMSO-d6) 11.47 (s, 1H), 9.82 (s, 1H), 8.60 (s, 1H), 8.26 (d, J = 5.5 Hz, 2H), 7.69-7.64 (m, 2H), 7.51 (t, J = 7.4 Hz, 2H), 7.46-7.41 (m, 1H), 4.34 (t, J = 5.2 Hz, 2H), 4.14 (s, 3H), 3.73 (t, J = 5.2 Hz, 2H), 3.27 (s, 3H). |
| 37 | 1H NMR (500 MHz, DMSO-d6) ppm = 13.38 â€" 13.34 (m, 1H), 11.96 (s, 1H), 9.60 (s, 1H), 8.23 (d, J = 2.0 Hz, 1H), 7.57 (d, J = 8.2 Hz, 1H), 7.48 (t, J = 2.1 Hz, 1H), 7.27 (d, J = 8.3 Hz, 1H), 4.02 â€" 3.97 (m, 2H), 3.97 (s, 3H), 3.96 â€" 3.90 (m, 1H), 3.57 (td, J = 11.5, 2.4 Hz, 2H), 1.87 â€" 1.74 (m, 4H). |
| 41 | 1H NMR (400 MHz, DMSO-d6) ppm = 10.02-9.90 (m, 1H), 9.10 (s, 1H), 7.37 (d, J = 8.0 Hz, 1H), 7.31-7.21 (m, 4H), 7.19-7.15 (m, 1H), 3.99 (s, 3H), 3.79 (dt, J = 13.2, 4.2 Hz, 2H), 3.33-3.23 (m, 2H), 1.95 (s, 3H), 1.51-1.45 (m, 4H), 1.15 (s, 3H). |
| 42 | 1H NMR (400 MHz, DMSO-d6) ppm = 11.24 (s, 1H), 9.62 (s, 1H), 8.59-8.57 (m, 1H), 8.25-8.23 (m, 1H), 7.67 (d, J = 8.2 Hz, 1H), 7.64-7.60 (m, 2H), 7.50-7.44 (m, 2H), 7.41-7.34 (m, 2H), 4.33 (t, J = 5.2 Hz, 2H), 4.03 (s, 3H), 3.73 (t, J = 5.2 Hz, 2H), 3.26 (s, 3H). |
| 43 | 1H NMR (400 MHz, DMSO-d6) ppm = 10.64 (s, 1H), 9.61 (s, 1H), 8.89 (s, 1H), 7.70 (d, J = 8.1 Hz, 1H), 7.64-7.60 (m, 2H), 7.50-7.45 (m, 2H), 7.42-7.36 (m, 2H), 4.04 (s, 3H), 2.53 (s, 3H). |
| 44 | 1H NMR (400 MHz, DMSO-d6) ppm = 11.23-11.21 (m, 1H), 9.62 (s, 1H), 8.55-8.53 (m, 1H), 8.22-8.21 (m, 1H), 7.67 (d, J = 8.1 Hz, 1H), 7.63-7.60 (m, 2H), 7.50-7.44 (m, 2H), 7.41-7.34 (m, 2H), 4.03 (s, 3H), 3.91 (s, 3H). |
| 45 | 1H NMR (400 MHz, DMSO-d6) ppm = 11.59 (s, 1H), 9.62 (s, 1H), 7.64 (d, J = 8.2 Hz, 1H), 7.61-7.58 (m, 2H), 7.48-7.43 (m, 2H), 7.40-7.35 (m, 1H), 7.34 (d, J =8.3 Hz, 1H), 4.02 (s, 3H), 2.17-2.10 (m, 1H), 0.94-0.85 (m, 4H). |
| 46 | 1H NMR (400 MHz, DMSO-d6) ppm = 11.54 (s, 1H), 9.56 (s, 1H), 7.71 (d, J = 8.2 Hz, 1H), 7.64-7.61 (m, 2H), 7.57 (d, J = 2.1 Hz, 1H), 7.50-7.45 (m, 2H), 7.42-7.36 (m, 3H), 4.14 (s, 3H), 4.03 (s, 3H). |

| No. | NMR |
|---|---|
| 47 | 1H NMR (400 MHz, DMSO-d6) ppm = 11.92 (s, 1H), 9.58 (s, 1H), 9.39-9.37 (m, 1H), 9.03-9.00 (m, 1H), 7.71 (d, J = 8.2 Hz, 1H), 7.64-7.60 (m, 2H), 7.51-7.45 (m, 2H), 7.42-7.37 (m, 2H), 4.04 (s, 3H). |
| 48 | 1H NMR (400 MHz, DMSO-d6) ppm = 11.79 (s, 1H), 9.56 (s, 1H), 8.76 (s, 1H), 7.70 (d, J = 8.2 Hz, 1H), 7.64-7.60 (m, 2H), 7.50-7.45 (m, 2H), 7.41-7.36 (m, 2H), 4.04 (s, 3H), 2.73 (s, 3H). |
| 49 | 1H NMR (400 MHz, DMSO-d6) ppm = 14.99-14.73 (m, 1H), 10.75-10.59 (m, 1H), 9.62 (s, 1H), 8.85-8.72 (m, 1H), 7.72 (d, J = 8.1 Hz, 1H), 7.65-7.61 (m, 2H), 7.51-7.45 (m, 2H), 7.42-7.37 (m, 2H), 4.04 (s, 3H). |
| 50 | 1H NMR (400 MHz, DMSO-d6) d 10.03-9.90 (m, 1H), 9.19 (s, 1H), 7.65-7.59 (m, 2H), 7.57 (d, J = 8.2 Hz, 1H), 7.31-7.24 (m, 3H), 3.99 (s, 3H), 3.81 (dt, J = 13.1, 4.2 Hz, 2H), 3.36-3.22 (m, 2H), 1.53-1.45 (m, 4H), 1.16 (s, 3H). |
| 51 | 1H NMR (400MHz, DMSO, ppm): 10.1 (s, 1H), 9.39 (s, 1H), 8.03 (s, 1H), 4.36 (s, 1H), 4.04 (s, 3H), 3.99-3.96 (m, 2H), 3.82-3.79 (m, 2H), 3.70-3.64 (m, 1H), 3.55-3.50 (m, 2H), 3.29-3.25 (m, 2H), 1.91-1.73 (m, 4H), 1.55-1.45 (m, 4H), 1.15 (s, 3H). |
| 52 | 1H NMR (400 MHz, DMSO-d6) d 11.54 (s, 1H), 9.65 (s, 1H), 7.48 (d, J = 8.2 Hz, 1H), 7.21 (d, J = 8.2 Hz, 1H), 4.01-3.95 (m, 2H), 3.95 (s, 3H), 3.94-3.86 (m, 1H), 3.55 (td, J = 11.4, 2.7 Hz, 2H), 2.16-2.09 (m, 1H), 1.86-1.70 (m, 4H), 0.94-0.85 (m, 4H). |
| 56 | 1H NMR (400MHz, DMSO, ppm): 11.41 (s, 1H), 9.83 (s, 1H), 8.58 (s, 1H), 8.24 (s, 1H), 8.11 (s, 1H), 4.35 (t, J = 5.2, 2H), 4.06-3.97 (m, 5H), 3.74-3.68 (m, 3H), 3.57-3.52 (m, 2H), 3.26 (s, 3H), 1.95-1.75 (m, 4H). |
| 60 | 1H NMR (700 MHz, DMSO-d6) d 10.13-9.88 (m, 1H), 9.13 (s, 1H), 7.53 (d, J = 8.0 Hz, 1H), 7.48-7.43 (m, 2H), 7.31-7.26 (m, 3H), 4.00 (s, 3H), 3.84-3.77 (m, 2H), 3.31-3.25 (m, 2H), 1.51-1.44 (m, 4H), 1.15 (s, 3H). |
| 62 | 1H NMR (500 MHz, DMSO-d6) d 10.15-9.91 (m, 1H), 9.21 (s, 1H), 7.62 (d, J = 8.2 Hz, 1H), 7.52-7.47 (m, 1H), 7.45-7.41 (m, 2H), 7.30 (d, J = 8.3 Hz, 1H), 7.23-7.18 (m, 1H), 4.00 (s, 3H), 3.85-3.79 (m, 2H), 3.33-3.26 (m, 2H), 1.53-1.44 (m, 4H), 1.16 (s, 3H). |
| 64 | 1H NMR (700 MHz, DMSO-d6) d 10.13 (s, 1H), 9.26 (s, 1H), 9.22-9.20 (m, 1H), 8.91-8.88 (m, 1H), 8.84-8.81 (m, 1H), 8.14 (dd, J = 8.0, 5.6 Hz, 1H), 7.87 (d, J = 8.2 Hz, 1H), 7.41 (d, J = 8.3 Hz, 1H), 4.04 (s, 3H), 3.84-3.79 (m, 2H), 3.32-3.25 (m, 2H), 1.52-1.45 (m, 4H), 1.16 (s, 3H). |
| 65 | 1H NMR (500 MHz, DMSO-d6) d 11.87-11.24 (m, 1H), 10.29-10.21 (m, 1H), 9.35(s, 1H), 8.16-7.79 (m, 1H), 7.27 (d, J = 8.7 Hz, 1H), 3.99 (s, 3H), 3.85-3.66 (m, 6H), 3.35-3.25 (m, 2H), 2.11-2.00 (m, 4H), 1.79-1.72 (m, 4H), 1.53-1.44 (m, 4H), 1.16 (s, 3H). |
| 68 | 1H NMR (400 MHz, DMSO-d6) delta 11.22-11.18 (m, 1H), 9.64 (s, 1H), 8.54-8.52 (m, 1H), 8.22-8.20 (m, 1H), 7.51 (d, J = 8.2 Hz, 1H), 7.23 (d, J = 8.3 Hz, 1H), 4.01-3.95 (m, 2H), 3.95 (s, 3H), 3.94-3.91 (m, 1H), 3.90 (s, 3H), 3.60-3.52 (m, 2H), 1.87-1.71 (m, 4H). |
| 71 | 1H NMR (500 MHz, DMSO-d6) d 10.98 (s, 1H), 9.64 (s, 1H), 8.93 (s, 1H), 7.55 (d, J = 8.1 Hz, 1H), 7.26 (d, J = 8.3 Hz, 1H), 4.66 (t, J = 5.1 Hz, 2H), 4.02-3.97 (m, 2H), 3.97 (s, 3H), 3.97-3.90 (m, 1H), 3.80 (t, J = 5.3 Hz, 2H), 3.56 (td, J = 11.5, 2.5 Hz, 2H), 3.28 (s, 3H), 1.87-1.74 (m, 4H). |
| 78 | 1H NMR (500 MHz, DMSO-d6) d 11.75 (s, 1H), 9.58 (s, 1H), 8.74 (s, 1H), 7.54 (d, J = 8.2 Hz, 1H), 7.26 (d, J = 8.3 Hz, 1H), 4.04-3.97 (m, 2H), 3.98 (s, 3H), 3.99-3.90 (m, 1H), 3.71-3.54 (m, 2H), 2.73 (s, 3H), 1.87-1.73 (m, 4H). |
| 86 | 1H NMR (400 MHz, DMSO-d6) d 10.80 (s, 1H), 9.39 (s, 1H), 7.63 (d, J = 8.2 Hz, 1H), 7.61-7.58 (m, 2H), 7.49-7.43 (m, 2H), 7.40-7.35 (m, 1H), 7.32 (d, J = 8.2 Hz, 1H), 4.96 (hept, J = 6.3 Hz, 1H), 4.00 (s, 3H), 1.28 (d, J = 6.2 Hz, 6H). |
| 88 | 1H NMR (700 MHz, DMSO-d6) d 11.26 (s, 1H), 9.37 (s, 1H), 7.71 (d, J = 8.1 Hz, 1H), 7.61-7.59 (m, 2H), 7.48-7.45 (m, 2H), 7.40-7.37 (m, 2H), 4.03 (s, 3H), 1.85-1.83 (m, 2H), 1.76-1.74 (m, 2H). |
| 89 | 1H NMR (400 MHz, DMSO-d6) d 10.96-10.90 (m, 1H), 9.62 (s, 1H), 8.88 (s, 1H), 7.71 (d, J = 8.2 Hz, 1H), 7.65-7.60 (m, 2H), 7.51-7.44 (m, 2H), 7.42-7.36 (m, 2H), 4.17 (s, 3H), 4.04 (s, 3H). |
| 90 | 1H NMR (500 MHz, DMSO-d6) d 11.02 (s, 1H), 9.62 (s, 1H), 8.95 (s, 1H), 7.71 (d, J = 8.2 Hz, 1H), 7.64-7.61 (m, 2H), 7.50-7.46 (m, 2H), 7.42-7.37 (m, 2H), 4.68-4.65 (m, 2H), 4.04 (s, 3H), 3.82-3.79 (m, 2H), 3.29 (s, 3H). |
| 94 | 1H NMR (400 MHz, DMSO-d6) d 13.38-13.32 (m, 1H), 11.98 (s, 1H), 9.57 (s, 1H), 8.23 (d, J = 2.1 Hz, 1H), 7.73 (d, J = 8.2 Hz, 1H), 7.64-7.60 (m, 2H), 7.50-7.45 (m, 3H), 7.42-7.37 (m, 2H), 4.04 (s, 3H). |
| 102 | 1H NMR (400 MHz, DMSO, ppm): 11.82 (s, 1H), 9.79 (s, 1H), 8.25 (s,1H), 7.65 (t, J = 0.8, 2H), 7.51-7.42 (m, 3H), 4.12 (s, 3H), 2.09-2.19 (m, 1H), 0.92-0.91 (m, 4H). |
| 103 | 1H NMR (400 MHz, DMSO, ppm): 10.19 (s, 1H), 9.40 (s, 1H), 8.04 (s, 1H), 4.67 (s, 1H), 4.03 (s, 3H), 4.01-3.88 (m, 4H), 3.74-3.63 (m, 1H), 3.58-3.45 (m, 2H), 3.19 (t, J = 12.4 Hz, 2H), 2.84 (t, J = 2.6 Hz, 1H), 2.33 (d, J = 2.7 Hz, 2H), 1.88 (dd, J = 12.4, 4.2 Hz, 2H), 1.78 (d, J = 12.6 Hz, 2H), 1.66 (td, J = 12.8, 4.4 Hz, 2H), 1.54 (d, J = 13.3 Hz, 2H). |
| 104 | 1H NMR (400 MHz, DMSO, ppm): 10.15 (s,1H), 9.40 (s, 1H), 8.04 (s, 1H), 4.56 (t, J = 5.4 Hz, 1H), 4.03 (s, 3H), 3.98 (dd, J = 11.2, 4.1 Hz, 2H), 3.74 (dd, J = 11.9, 6.9 Hz, 2H), 3.66 (d, J = 11.9 Hz, 1H), 3.53 (d, J = 2.2 Hz, 2H), 3.27 (d, J = 10.3 Hz, 2H), 3.19 (d, J = 5.5 Hz, 2H), 1.88 (dd, J = 12.4, 4.2 Hz, 2H), 1.79-1.76 (m, 2H), 1.55-1.40 (m, 2H), 1.31-1.17 (m, 2H), 0.92 (s, 3H). |
| 105 | 1H NMR (400 MHz, DMSO-d6) d 11.66 (s, 1H), 9.58 (s, 1H), 8.23 (s, 1H), 7.70 (d, J = 8.1 Hz, 1H), 7.65-7.59 (m, 2H), 7.51-7.44 (m, 2H), 7.42-7.35 (m, 2H), 4.03 (s, 3H), 2.54 (s, 3H). |
| 106 | 1H NMR (400 MHz, DMSO, ppm): 11.74 (s, 1H), 9.81 (s, 1H), 8.09 (s, 1H), 4.07 (s, 3H), 4.00-3.96 (m, 2H), 3.71-3.65 (m, 1H), 3.56-3.50 (m, 2H), 2.11-2.08 (m, 1H), 1.92-1.76 (m, 4H), 0.91-0.95 (m, 4H). |
| 107 | 1H NMR (500 MHz, DMSO-d6) d 9.62-9.55 (m, 1H), 9.09 (s, 1H), 7.46 (d, J = 8.1 Hz, 1H), 7.00 (d, J = 8.1 Hz, 1H), 3.92 (s, 3H), 3.80 (dt, J = 12.6, 4.0 Hz, 2H), 3.33-3.26 (m, 2H), 3.01 (t, J = 7.6 Hz, 2H), 1.67-1.60 (m, 2H), 1.54-1.45 (m, 4H), 1.33 (h, J = 7.3 Hz, 2H), 1.16 (s, 3H), 0.91 (t, J = 7.4 Hz, 3H). |
| 108 | 1H NMR (500 MHz, DMSO-d6) d 10.02-9.82 (m, 1H), 9.19 (s, 1H), 7.36 (d, J = 8.0 Hz, 1H), 7.12 (d, J = 8.1 Hz, 1H) 3.91 (s, 3H), 3.80 (dt, J = 13.8, 4.5 Hz, 2H), 3.33-3.24 (m, 2H), 3.04 (t, J = 7.6 Hz, 2H), 1.65-1.58 (m, 2H), 1.52-1.44 (m, 4H), 1.33 (h, J = 7.4 Hz, 2H), 1.15 (s, 3H), 0.90 (t, J = 7.4 Hz, 3H). |
| 110 | 1H NMR (500 MHz, DMSO-d6) d 9.64-9.56 (m, 1H), 9.11 (s, 1H), 7.71 (d, J = 8.2 Hz, 1H), 7.51-7.46 (m, 3H), 7.21-7.15 (m, 2H), 4.01 (s, 3H), 3.79-3.73 (m, 2H), 3.30-3.23 (m, 2H), 1.51-1.42 (m, 4H), 1.14 (s, 3H). |
| 111 | 1H NMR (700 MHz, DMSO-d6) d 9.60-9.51 (m, 1H), 9.08 (s, 1H), 7.60 (d, J = 8.2 Hz, 1H), 7.47-7.41 (m, 2H), 7.29-7.25 (m, 2H), 7.17 (d, J = 8.2 Hz, 1H), 4.01 (s, 3H), 3.74-3.70 (m, 2H), 3.26-3.20 (m, 2H), 1.48-1.41 (m, 4H), 1.13 (s, 3H). |
| 112 | 1H NMR (700 MHz, DMSO-d6) d 9.91 (s, 1H), 9.37-9.36 (m, 1H), 9.20 (s, 1H), 8.94-8.92 (m, 1H), 8.89-8.87 (m, 1H), 8.15 (dd, J = 8.2, 5.6 Hz, 1H), 8.02 (d, J = 8.3 Hz, 1H), 7.29 (d, J = 8.3 Hz, 1H), 4.11-4.04 (m, 2H), 4.05 (s, 3H), 3.23-3.18 (m, 2H), 1.91-1.87 (m, 2H), 1.85-1.80 (m, 2H), 1.65 (s, 3H). |
| 113 | 1H NMR (700 MHz, DMSO-d6) d 11.12 (s, 1H), 9.67 (s, 1H), 8.29 (d, J = 9.1 Hz, 1H), 7.73 (d, J = 8.1 Hz, 1H), 7.64-7.62 (m, 2H), 7.51-7.47 (m, 2H), 7.41-7.39 (m, 2H), 4.18 (s, 3H), 4.05 (s, 3H). |
| 114 | 1H NMR (500 MHz, DMSO-d6) d 9.98-9.94 (m, 1H), 9.28 (s, 1H), 8.62-8.61 (m, 1H), 8.56-8.54 (m, 1H), 8.15-8.14 (m, 1H), 7.82 (d, J = 8.3 Hz, 1H), 7.78 (td, J = 7.7, 1.8 Hz, 1H), 7.33-7.30 (m, 1H), 7.23 (d, J = 8.4 |

| No. | NMR |
|---|---|
| | Hz, 1H), 7.14-7.12 (m, 1H), 5.51 (s, 2H), 4.36 (s, 1H), 3.96 (s, 3H), 3.84-3.78 (m, 2H), 3.32-3.25 (m, 2H), 1.52-1.45 (m, 4H), 1.16 (s, 3H). |
| 115 | 1H NMR (400 MHz, DMSO-d6) d 10.05-10.02 (m, 1H), 9.24 (s, 1H), 8.80 (q, J = 4.8 Hz, 1H), 8.70-8.67 (m, 1H), 8.29-8.27 (m, 1H), 7.85 (dd, J = 5.0, 1.8 Hz, 1H), 7.76 (d, J = 8.2 Hz, 1H), 7.35 (d, J = 8.3 Hz, 1H), 4.35 (s, 1H), 4.02 (s, 3H), 3.85-3.77 (m, 2H), 3.34-3.25 (m, 2H), 2.86 (d, J = 4.8 Hz, 3H), 1.53-1.44 (m, 4H), 1.16 (s, 3H). |
| 116 | 1H NMR (400 MHz, DMSO-d6) d 9.95-9.92 (m, 1H), 9.29 (s, 1H), 8.55-8.54 (m, 1H), 8.22-8.21 (m, 1H), 7.81 (d, J = 8.3 Hz, 1H), 7.23 (d, J = 8.4 Hz, 1H), 5.35-5.28 (m, 1H), 4.36-4.29 (m, 3H), 4.24-4.16 (m, 2H), 3.96 (s, 3H), 3.85-3.77 (m, 2H), 3.34-3.26 (m, 2H), 1.53-1.45 (m, 4H), 1.43 (s, 9H), 1.16 (s, 3H). |
| 117 | 1H NMR (500 MHz, DMSO-d6) d 10.00-9.95 (m, 1H), 9.20 (s, 1H), 7.58 (d, J = 8.2 Hz, 1H), 7.37-7.33 (m, 1H), 7.28 (d, J = 8.3 Hz, 1H), 7.16-7.13 (m, 2H), 6.97-6.94 (m, 1H), 4.36 (s, 1H), 4.15-4.12 (m, 2H), 3.99 (s, 3H), 3.84-3.78 (m, 2H), 3.70-3.67 (m, 2H), 3.33-3.32 (m, 3H), 3.32-3.25 (m, 2H), 1.52-1.44 (m, 4H), 1.16 (s, 3H). |
| 118 | 1H NMR (500 MHz, DMSO-d6) d 10.00-9.95 (m, 1H), 9.19 (s, 1H), 7.56 (d, J = 8.2 Hz, 1H), 7.53-7.51 (m, 1H), 7.51-7.48 (m, 1H), 7.45-7.41 (m, 1H), 7.33-7.30 (m, 1H), 7.29 (d, J = 8.3 Hz, 1H), 4.56 (s, 2H), 4.36 (s, 1H), 3.99 (s, 3H), 3.83-3.78 (m, 2H), 3.61-3.59 (m, 2H), 3.51-3.48 (m, 2H), 3.32-3.25 (m, 3H), 1.52-1.44 (m, 4H), 1.15 (s, 3H). |
| 119 | 1H NMR (700 MHz, DMSO-d6) d 9.96 (s, 1H), 9.29 (s, 1H), 8.45 (s, 1H), 8.08 (s, 1H), 7.78 (d, J = 8.2 Hz, 1H), 7.22 (d, J = 8.4 Hz, 1H), 4.37 (s, 1H), 4.32 (t, J = 5.5 Hz, 2H), 3.96 (s, 3H), 3.84-3.79 (m, 4H), 3.55-3.53 (m, 2H), 3.44-3.41 (m, 2H), 3.36-3.27 (m, 2H), 3.21 (s, 3H), 1.52-1.46 (m, 4H), 1.16 (s, 3H). |
| 120 | 1H NMR (400 MHz, DMSO-d6) d 11.60 (s, 1H), 9.57 (s, 1H), 7.61 (d, J = 8.1 Hz, 1H), 7.49-7.43 (m, 2H), 7.34 (d, J = 8.2 Hz, 1H), 7.32-7.25 (m, 2H), 4.03 (s, 3H), 2.16-2.09 (m, 1H), 0.91-0.85 (m, 4H). |
| 121 | 1H NMR (400 MHz, DMSO-d6) d 11.67 (s, 1H), 9.66 (s, 1H), 9.21-9.19 (m, 1H), 8.89-8.86 (m, 1H), 8.82 (dt, J = 8.2, 1.8 Hz, 1H), 8.13 (dd, J = 8.2, 5.6 Hz, 1H), 7.94 (d, J = 8.2 Hz, 1H), 7.44 (d, J = 8.3 Hz, 1H), 4.06 (s, 3H), 2.13 (quint, J = 6.3 Hz, 1H), 0.91 (d, J = 6.1 Hz, 4H). |
| 122 | 1H NMR (400 MHz, DMSO-d6) d 11.78 (s, 1H), 9.76 (s, 1H), 8.17-8.05 (m, 1H), 7.31 (d, J = 8.7 Hz, 1H), 4.01 (s, 3H), 3.88-3.73 (m, 4H), 2.18-2.04 (m, 5H), 1.79-1.74 (m, 4H), 0.92 (d, J = 6.1 Hz, 4H). |
| 123 | 1H NMR (500 MHz, DMSO-d6) d 11.65 (s, 1H), 9.60 (s, 1H), 7.66 (d, J = 8.1 Hz, 1H), 7.51-7.45 (m, 1H), 7.36 (d, J = 8.2 Hz, 1H), 7.33-7.26 (m, 2H), 4.04 (s, 3H), 2.15-2.10 (m, 1H), 0.92-0.86 (m, 4H). |
| 124 | 1H NMR (400 MHz, DMSO-d6) d 11.62 (s, 1H), 9.59 (s, 1H), 7.65 (d, J = 8.1 Hz, 1H), 7.38-7.25 (m, 4H), 4.03 (s, 3H), 2.17-2.09 (m, 1H), 0.93-0.85 (m, 4H). |
| 125 | 1H NMR (500 MHz, DMSO-d6) d 11.73 (s, 1H), 9.55 (s, 1H), 8.23 (s, 1H), 7.72 (d, J = 8.1 Hz, 1H), 7.53-7.47 (m, 2H), 7.41 (d, J = 8.2 Hz, 1H), 7.35-7.28 (m, 2H), 4.05 (s, 3H), 2.54 (s, 3H). |
| 126 | 1H NMR (400 MHz, DMSO-d6) delta 11.61-11.58 (m, 1H), 9.62 (s, 1H), 7.67-7.61 (m, 3H), 7.33 (d, J = 8.3 Hz, 1H), 7.32-7.25 (m, 2H), 4.02 (s, 3H), 2.17-2.10 (m, 1H), 0.94-0.86 (m, 4H). |
| 127 | 1H NMR (400 MHz, DMSO-d6) d 11.60 (s, 1H), 9.63 (s, 1H), 9.28-9.21 (m, 2H), 7.48 (d, J = 8.2 Hz, 1H), 7.24 (d, J = 8.3 Hz, 1H), 5.99-5.96 (m, 1H), 3.98 (s, 3H), 3.81-3.74 (m, 2H), 3.36-3.29 (m, 2H), 2.91-2.85 (m, 2H), 2.17-2.09 (m, 1H), 0.93-0.86 (m, 4H). |
| 128 | 1H NMR (400 MHz, DMSO-d6) delta 11.70 (s, 1H), 9.55 (s, 1H), 8.23 (s, 1H), 7.71 (d, J = 8.1 Hz, 1H), 7.39 (d, J = 8.2 Hz, 1H), 7.39-7.27 (m, 3H), 4.05 (s, 3H), 2.54 (s, 3H). |
| 129 | 1H NMR (400 MHz, DMSO-d6) delta 11.73 (s, 1H), 9.53 (s, 1H), 8.24 (s, 1H), 7.68 (d, J = 8.1 Hz, 1H), 7.51-7.44 (m, 2H), 7.39 (d, J = 8.2 Hz, 1H), 7.34-7.27 (m, 2H), 4.04 (s, 3H), 2.54 (s, 3H). |
| 130 | 1H NMR (400 MHz, DMSO-d6) delta 11.66 (s, 1H), 9.60 (s, 1H), 8.23 (s, 1H), 7.54 (d, J = 8.2 Hz, 1H), 7.26 (d, J = 8.3 Hz, 1H), 4.02-3.97 (m, 2H), 3.96 (s, 3H), 3.96-3.88 (m, 1H), 3.56 (td, J = 11.4, 2.7 Hz, 2H), 2.54 (s, 3H), 1.87-1.72 (m, 4H). |
| 131 | 1H NMR (400 MHz, DMSO-d6) delta 11.72 (s, 1H), 9.58 (s, 1H), 8.24 (s, 1H), 7.71 (d, J = 8.2 Hz, 1H), 7.69-7.63 (m, 2H), 7.37 (d, J = 8.3 Hz, 1H), 7.33-7.27 (m, 2H), 4.03 (s, 3H), 2.54 (s, 3H). |
| 132 | 1H NMR (400 MHz, DMSO-d6) delta 11.67 (s, 1H), 9.58 (s, 1H), 8.23 (s, 1H), 7.52 (d, J = 8.1 Hz, 1H), 7.25 (d, J = 8.2 Hz, 1H), 6.05-6.02 (m, 1H), 4.26 (q, J = 2.8 Hz, 2H), 3.98 (s, 3H), 3.86 (t, J = 5.4 Hz, 2H), 2.67-2.62 (m, 2H), 2.54 (s, 3H). |
| 133 | 1H NMR (500 MHz, DMSO-d6) d 10.12-9.94 (m, 1H), 9.50-9.42 (m, 1H), 9.40-9.33 (m, 1H), 9.30 (s, 1H), 8.60 (s, 1H), 8.30 (s, 1H), 7.82 (d, J = 8.3 Hz, 1H), 7.25 (d, J = 8.4 Hz, 1H), 5.53 (quint, J = 7.6 Hz, 1H), 4.43-4.36 (m, 4H), 3.96 (s, 3H), 3.85-3.78 (m, 2H), 3.33-3.26 (m, 2H), 1.53-1.44 (m, 4H), 1.16 (s, 3H). |
| 134 | 1H NMR (400 MHz, DMSO-d6) delta 11.82-11.76 (m, 1H), 9.55 (s, 1H), 8.75 (s, 1H), 7.51 (d, J = 8.1 Hz, 1H), 7.25 (d, J = 8.2 Hz, 1H), 6.04-6.01 (m, 1H), 4.26 (q, J = 2.7 Hz, 2H), 3.98 (s, 3H), 3.86 (t, J = 5.4 Hz, 2H), 2.72 (s, 3H), 2.67-2.61 (m, 2H). |
| 135 | 1H NMR (400 MHz, DMSO-d6) d 11.22 (s, 1H), 9.62 (s, 1H), 8.54-8.53 (m, 1H), 8.22-8.21 (m, 1H), 7.49 (d, J = 8.2 Hz, 1H), 7.23 (d, J = 8.2 Hz, 1H), 6.04-6.01 (m, 1H), 4.26 (q, J = 2.7 Hz, 2H), 3.97 (s, 3H), 3.91 (s, 3H), 3.86 (t, J = 5.4 Hz, 2H), 2.68-2.62 (m, 2H). |
| 136 | 1H NMR (400 MHz, DMSO-d6) d 11.72 (s, 1H), 10.03 (s, 1H), 9.64 (s, 1H), 9.15 (s, 1H), 7.53 (d, J = 8.1 Hz, 1H), 7.26 (d, J = 8.3 Hz, 1H), 6.06-6.03 (m, 1H), 4.27 (q, J = 2.7 Hz, 2H), 3.99 (s, 3H), 3.87 (t, J = 5.4 Hz, 2H), 2.69-2.63 (m, 2H). |
| 137 | 1H NMR (400 MHz, DMSO-d6) d 10.84 (s, 1H), 9.40 (s, 1H), 8.88-8.80 (m, 3H), 7.54 (d, J = 8.1 Hz, 1H), 7.26 (d, J = 8.2 Hz, 1H), 6.04-6.00 (m, 1H), 4.26 (q, J = 2.7 Hz, 2H), 3.97 (s, 3H), 3.85 (t, J = 5.4 Hz, 2H), 2.66-2.61 (m, 2H), 1.83-1.78 (m, 2H), 1.50-1.45 (m, 2H). |
| 138 | 1H NMR (400 MHz, DMSO-d6) d 11.83 (s, 1H), 9.64 (s, 1H), 9.24-9.21 (m, 1H), 8.92-8.88 (m, 1H), 8.84-8.80 (m, 1H), 8.26 (s, 1H), 8.15-8.10 (m, 1H), 8.00 (d, J = 8.3 Hz, 1H), 7.49 (d, J = 8.4 Hz, 1H), 4.08 (s, 3H), 2.54 (s, 3H). |
| 139 | 1H NMR (500 MHz, DMSO-d6) d 10.55-10.47 (m, 1H), 9.68 (s, 1H), 7.80 (s, 1H), 7.51 (d, J = 8.1 Hz, 1H), 7.25 (d, J = 8.3 Hz, 1H), 6.06-6.03 (m, 1H), 4.26 (q, J = 2.7 Hz, 2H), 3.98 (s, 3H), 3.86 (t, J = 5.4 Hz, 2H), 2.67-2.62 (m, 2H). |
| 140 | 1H NMR (400 MHz, DMSO-d6) d 11.80 (s, 1H), 9.56 (s, 1H), 8.80 (s, 1H), 7.52 (d, J = 8.2 Hz, 1H), 7.26 (d, J = 8.2 Hz, 1H), 6.05-6.02 (m, 1H), 4.26 (q, J = 2.7 Hz, 2H), 4.07 (dd, J = 8.2, 7.0 Hz, 1H), 3.99 (s, 3H), 3.96-3.79 (m, 6H), 2.68-2.62 (m, 2H), 2.47-2.37 (m, 1H), 2.21-2.12 (m, 1H). |
| 141 | 1H NMR (400 MHz, DMSO-d6) d 11.58 (s, 1H), 9.68 (s, 1H), 7.54 (d, J = 8.3 Hz, 1H), 7.23 (d, J = 8.3 Hz, 1H), 6.99-6.97 (m, 1H), 5.12-5.08 (m, 2H), 4.80-4.76 (m, 2H), 3.99 (s, 3H), 2.17-2.10 (m, 1H), 0.94-0.86 (m, 4H). |
| 142 | 1H NMR (400 MHz, DMSO-d6) delta 11.42-11.39 (m, 1H), 9.61 (s, 1H), 8.73-8.72 (m, 1H), 8.54-8.44 (m, 3H), 7.51 (d, J = 8.1 Hz, 1H), 7.25 (d, J = 8.2 Hz, 1H), 7.14-7.12 (m, 1H), 6.05-6.02 (m, 1H), 4.26 (q, J = 2.8 Hz, 2H), 4.15 (q, J = 5.7 Hz, 2H), 3.98 (s, 3H), 3.86 (t, J = 5.4 Hz, 2H), 2.67-2.62 (m, 2H). |
| 143 | 1H NMR (500 MHz, DMSO-d6) d 13.32-13.16 (m, 1H), 11.16 (s, 1H), 9.01 (s, 1H), 7.50 (d, J = 8.2 Hz, 1H), 7.30 (d, J = 8.2 Hz, 1H), 6.06-6.03 (m, 1H), 4.42 (q, J = 7.1 Hz, 2H), 4.26 (q, J = 2.7 Hz, 2H), 4.04 (s, 3H), 3.86 (t, J = 5.4 Hz, 2H), 2.67-2.61 (m, 2H), 1.36 (t, J = 7.1 Hz, 3H). |

| No. | NMR |
|---|---|
| 144 | 1H NMR (400 MHz, DMSO-d6) d 10.55-10.49 (m, 1H), 9.34 (s, 1H), 7.50 (d, J = 8.1 Hz, 1H), 7.23 (d, J = 8.3 Hz, 1H), 6.03-6.00 (m, 1H), 4.25 (q, J = 2.7 Hz, 2H), 3.96 (s, 3H), 3.85 (t, J = 5.5 Hz, 2H), 3.08-2.68 (m, 6H), 2.66-2.60 (m, 2H), 1.61-1.57 (m, 2H), 1.31-1.27 (m, 2H). |
| 145 | 1H NMR (400 MHz, DMSO-d6) d 10.83 (s, 1H), 9.68-9.59 (m, 1H), 9.39 (s, 1H), 7.51 (d, J = 8.2 Hz, 1H), 7.24 (d, J = 8.3 Hz, 1H), 6.04-6.00 (m, 1H), 4.26 (q, J = 2.7 Hz, 2H), 3.97 (s, 3H), 3.85 (t, J = 5.4 Hz, 2H), 3.52 (d, J = 5.7 Hz, 2H), 2.81 (d, J = 4.9 Hz, 6H), 2.65-2.60 (m, 2H), 1.60-1.56 (m, 2H), 1.25-1.21 (m, 2H). |
| 146 | 1H NMR (400 MHz, DMSO-d6) d 11.57 (s, 1H), 9.48 (s, 1H), 7.56 (d, J = 8.1 Hz, 1H), 7.28 (d, J = 8.3 Hz, 1H), 6.06-6.03 (m, 1H), 4.27 (q, J = 2.7 Hz, 2H), 4.00 (s, 3H), 3.87 (t, J = 5.4 Hz, 2H), 2.86 (s, 3H), 2.68-2.63 (m, 2H). |
| 147 | 1H NMR (500 MHz, DMSO-d6) d 11.59 (s, 1H), 9.63 (s, 1H), 7.66 (d, J = 8.2 Hz, 1H), 7.37-7.33 (m, 1H), 7.32 (d, J = 8.3 Hz, 1H), 7.18-7.14 (m, 2H), 6.97-6.94 (m, 1H), 4.16-4.12 (m, 2H), 4.02 (s, 3H), 3.70-3.67 (m, 2H), 3.32 (s, 3H), 2.17-2.10 (m, 1H), 0.93-0.85 (m, 4H). |
| 148 | 1H NMR (500 MHz, DMSO-d6) d 11.68-11.64 (m, 1H), 9.58 (s, 1H), 8.23 (s, 1H), 7.71 (d, J = 8.2 Hz, 1H), 7.39-7.35 (m, 2H), 7.19-7.17 (m, 2H), 6.99-6.96 (m, 1H), 4.16-4.14 (m, 2H), 4.03 (s, 3H), 3.70-3.67 (m, 2H), 3.33 (s, 3H), 2.54 (s, 3H). |
| 149 | 1H NMR (500 MHz, DMSO-d6) d 10.58-10.51 (m, 1H), 9.34 (s, 1H), 7.68 (d, J = 8.2 Hz, 1H), 7.61-7.58 (m, 2H), 7.48-7.44 (m, 2H), 7.40-7.36 (m, 1H), 7.36 (d, J = 8.2 Hz, 1H), 4.01 (s, 3H), 3.09-2.85 (m, 6H), 1.61-1.58 (m, 2H), 1.31-1.28 (m, 2H). |
| 150 | 1H NMR (500 MHz, DMSO-d6) d 10.87-10.85 (m, 1H), 9.69-9.61 (m, 1H), 9.40 (s, 1H), 7.69 (d, J = 8.2 Hz, 1H), 7.61-7.58 (m, 2H), 7.48-7.44 (m, 2H), 7.40-7.36 (m, 1H), 7.37 (d, J = 8.3 Hz, 1H), 4.02 (s, 3H), 3.53 (d, J = 5.7 Hz, 2H), 2.81 (d, J = 4.8 Hz, 6H), 1.61-1.57 (m, 2H), 1.25-1.22 (m, 2H). |
| 151 | 1H NMR (500 MHz, DMSO-d6) d 11.82-11.77 (m, 1H), 9.56 (s, 1H), 8.76 (s, 1H), 7.71 (d, J = 8.2 Hz, 1H), 7.39-7.35 (m, 2H), 7.19-7.16 (m, 2H), 6.99-6.96 (m, 1H), 4.16-4.14 (m, 2H), 4.03 (s, 3H), 3.70-3.67 (m, 2H), 3.33 (s, 3H), 2.73 (s, 3H). |
| 152 | 1H NMR (500 MHz, DMSO-d6) d 11.61-11.59 (m, 1H), 9.49 (s, 1H), 7.75 (d, J = 8.2 Hz, 1H), 7.40-7.36 (m, 2H), 7.20-7.17 (m, 2H), 6.99-6.96 (m, 1H), 4.17-4.14 (m, 2H), 4.04 (s, 3H), 3.70-3.68 (m, 2H), 3.33 (s, 3H), 2.87 (s, 3H). |
| 153 | 1H NMR (500 MHz, DMSO-d6) d 10.03-9.95 (m, 1H), 9.36 (d, J = 0.7 Hz, 1H), 9.35-9.32 (m, 1H), 8.54-8.52 (m, 1H), 8.50 (d, J = 0.7 Hz, 1H), 8.05-7.98 (m, 2H), 7.98 (d, J = 8.3 Hz, 1H), 7.40-7.36 (m, 1H), 7.27 (d, J = 8.4 Hz, 1H), 3.99 (s, 3H), 3.87-3.80 (m, 2H), 3.35-3.27 (m, 2H), 1.54-1.46 (m, 4H), 1.17 (s, 3H). |
| 154 | 1H NMR (400 MHz, DMSO-d6) d 11.81 (s, 1H), 9.65 (s, 1H), 8.60 (d, J = 8.8 Hz, 1H), 8.25 (s, 1H), 8.19 (d, J = 8.3 Hz, 1H), 8.11 (d, J = 8.8 Hz, 1H), 7.52 (d, J = 8.4 Hz, 1H), 4.09 (s, 3H), 2.82 (s, 3H), 2.55 (s, 3H). |
| 156 | 1H NMR (400 MHz, DMSO-d6) d 11.64 (s, 1H), 9.65 (s, 1H), 8.86 (s, 2H), 7.78 (d, J = 8.2 Hz, 1H), 7.38 (d, J = 8.1 Hz, 1H), 4.03 (s, 3H), 3.99 (s, 3H), 2.17-2.10 (m, 1H), 0.94-0.86 (m, 4H). |
| 157 | 1H NMR (700 MHz, DMSO-d6) d 11.72 (s, 1H), 9.71 (s, 1H), 8.97 (s, 1H), 8.49 (s, 1H), 8.25 (s, 1H), 8.05 (d, J = 8.3 Hz, 1H), 7.91 (t, J = 59.1 Hz, 1H), 7.35 (d, J = 8.3 Hz, 1H), 4.02 (s, 3H), 2.55 (s, 3H). |
| 158 | 1H NMR (700 MHz, DMSO-d6) d 10.03-10.00 (m, 1H), 9.32 (s, 1H), 8.90 (s, 1H), 8.45 (s, 1H), 7.92 (d, J = 8.3 Hz, 1H), 7.90 (t, J = 59.1 Hz, 1H), 7.26 (d, J = 8.3 Hz, 1H), 4.37 (s, 1H), 3.98 (s, 3H), 3.84-3.80 (m, 2H), 3.32-3.27 (m, 2H), 1.52-1.46 (m, 4H), 1.16 (s, 3H). |
| 160 | 1H NMR (400 MHz, DMSO-d6) delta 10.79-10.66 (m, 1H), 9.71 (s, 1H), 8.37-8.17 (m, 2H), 7.69 (d, J = 8.2 Hz, 1H), 7.64-7.60 (m, 2H), 7.50-7.45 (m, 2H), 7.42-7.36 (m, 2H), 4.04 (s, 3H). |
| 161 | 1H NMR (400 MHz, DMSO-d6) d 11.66 (s, 1H), 9.66 (s, 1H), 7.74-7.48 (m, 1H), 7.23 (d, J = 8.7 Hz, 1H), 4.01-3.95 (m, 2H), 3.96 (s, 3H), 3.83 (t, J = 5.7 Hz, 2H), 3.82-3.69 (m, 4H), 2.26-2.16 (m, 2H), 2.17-2.10 (m, 1H), 0.94-0.87 (m, 4H). |

EXAMPLE 2: PREPARATION OF THE COMPOUNDS OF THE PRESENT INVENTION AND ANALYTICAL METHODS

All solvents used were commercially available and were used without further purification. Reactions were typically run using anhydrous solvents under an inert atmosphere of nitrogen. Flash column chromatography was generally carried out using Silica gel 60 (0.035-0.070 mm particle size).

All NMR experiments were recorded either on Bruker Mercury Plus 400 NMR Spectrometer equipped with a Bruker 400 BBFO probe at 400 MHz for proton NMR or on Bruker Mercury Plus 300 NMR Spectrometer equipped with a Bruker 300 BBFO probe at 300 MHz for proton NMR. All deuterated solvents contained typically 0.03% to 0.05% v/v tetramethylsilane, which was used as the reference signal (set at ppm=0.00 for both 1H and 13C).

LC-MS analyses were performed on a SHIMADZU LC-MS machine consisting of an UFLC 20-AD system and LCMS 2020 MS detector or an Agilent Technologies 1200 series. The column used and the conditions are described in the different HPLC methods. The column temperature was at 40° C. with the flow rate stated. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

1. N-[8-methoxy-5-(oxan-4-yl)quinoxalin-2-yl]-1-(2-methoxyethyl)-1H-pyrazole-4-carboxamide a. 1-Bromo-4-methoxy-2,3-dinitro-benzene Into a 250-mL 3-necked round-bottom flask was placed 1-bromo-4-methoxy-2-nitrobenzene (50.0 g, 205 mmol) in sulfuric acid (100 ml). Nitric acid (24 mL, 530 mmol) was added dropwise with stirring at 0° C. The solution was stirred for 1 h at room temperature and quenched with 1000 ml of ice water. The solution was extracted twice with 1000 ml of ethyl acetate, the combined organic layers were dried over anhydrous sodium sulfate and concentrated to dryness. The crude material was recrystallized from ethyl acetate/hexane (2:3) to result in 20.0 g (32%) of 1-bromo-4-methoxy-2,3-dinitrobenzene as a yellow solid. Melting point: 150-153° C. 1H NMR (400 MHz, DMSO-d6) ppm=8.19 (d, J=9.3 Hz, 1H), 7.70 (d, J=9.3 Hz, 1H), 4.02 (s, 3H). HPLC/MS (purity) 91%. Rt 1.73 min (method A). [M+H]+ 276.8, 278.9.

General Procedure for Suzuki Reactions b. 4-(4-Methoxy-2,3-dinitro-phenyl)-3,6-dihydro-2H-pyran Into a 350-ml pressure tank reactor purged and maintained with an inert atmosphere of argon, was placed 1-bromo-4-methoxy-2,3-dinitrobenzene, 91% (15.7 g, 51.4 mmol), 2-(3,6-dihydro-2H-pyran-4-yl)-4,4,5,5-tetramethyl-1,3,2-dioxaborolane, 95% (13.7 g, 61.7 mmol), Pd(dppf)Cl2 dichloromethane complex, 95% (4.42 g, 5.14 mmol), potassium carbonate (8.53 g, 61.7 mmol, dissolved in water (12 ml)), ethanol (31.6 ml) and toluene (316 ml). The mixture was stirred for 1 h at 100° C., cooled to room temperature and concentrated to dryness under vacuum. The residue was purified by column chromatography (ethyl acetate/petrol ether: 1/1) to yield in 13.0 g (86%) of 4-(4-methoxy-2,3-dinitrophenyl)-3,6-dihydro-2H-pyran as an orange solid. HPLC/MS (purity) 95%. Rt 1.17 min (method B). [M+H]+ 281.2.

c. 3-Methoxy-6-(tetrahydro-pyran-4-yl)-benzene-1,2-diamine

Into a 250-ml round-bottom flask was placed Palladium/carbon, 10% (4.00 g, 3.76 mmol), methanol (100 ml) and 4-(4-methoxy-2,3-dinitrophenyl)-3,6-dihydro-2H-pyran, 95% (10.5 g, 33.9 mmol). The mixture was stirred for 15 h at 35° C. under a hydrogen atmosphere. The solids were filtered off and discarded. The filtrate was evaporated to dryness and the residue was purified by column chromatography (ethyl acetate/hexane, 70/30) to yield in 4.51 g (58%) of 3-methoxy-6-(oxan-4-yl)benzene-1,2-diamine as a yellow solid. Melting point: 116-117° C. 1H NMR (400 MHz, Chloroform-d) 6.67 (d, J=8.5 Hz, 1H), 6.45 (d, J=8.5 Hz, 1H), 4.18-4.09 (m, 2H), 3.86 (s, 3H), 3.65-3.53 (m, 2H), 3.46 (s, 4H), 2.82-2.64 (m, 1H), 1.93-1.73 (m, 4H). HPLC/MS (purity) 97%. Rt 1.01 min (method C). [M+H]+ 223.1.

General Procedure for Cyclisation to Quinoxaline Ring d. 8-Methoxy-5-(tetrahydro-pyran-4-yl)-1H-quinoxalin-2-one

3-Methoxy-6-(tetrahydro-pyran-4-yl)-benzene-1,2-diamine, 97% (3.41 g, 15.8 mmol) was dissolved in methanol (80 ml), ethyl glyoxylate, 50% solution in toluene (9.64 ml, 94.7 mmol) was added and the mixture was stirred at 80° C. for 2 h. The reaction mixture was evaporated to dryness and the crude material was triturated with ethyl acetate. The solid formed was filtered off and purified by flash chromatography (ethyl acetate/cyclohexane, gradient) to yield in 1.62 g (31%) of a colorless solid. HPLC/MS (purity) 80%. Rt 1.79 min (method D). [M+H]+ 261.1.

General Procedure to Introduce Chlorine e. 2-Chloro-8-methoxy-5-(tetrahydro-pyran-4-yl)-quinoxaline

8-Methoxy-5-(tetrahydro-pyran-4-yl)-1H-quinoxalin-2-one, 80% (1.62 g, 4.98 mmol) was dissolved in phosphoryl chloride (27.1 g, 177 mmol) at room temperature and the mixture was stirred at 105° C. for 3 h. After cooling to room temperature mixture was partitioned between saturated aqueous NaHCO3 solution and dichloromethane and stirred additional 1 h at RT. The organic layer was separated and the aqueous phase was extracted three times with dichloromethane. The combined organic layer were dried over sodium sulfate, filtered and the filtrate was evaporated to dryness to give 1.74 g (100%) of the title compound as a yellow solid. HPLC/MS (purity) 80%. Rt 2.36 min (method D). [M+H]+ 279.1.

General Procedure to Synthesize Amino-Quinoxalines f. 8-Methoxy-5-(tetrahydro-pyran-4-yl)-quinoxalin-2-ylamine

In a high-pressure tube 2-chloro-8-methoxy-5-(tetrahydro-pyran-4-yl)-quinoxaline, 80% (1.74 g, 4.98 mmol) was dissolved THF (20 ml). To this mixture ammonia solution in water, 32% (60 ml) and copper(I)iodide (500 mg, 2.62 mmol) were added, the vessel was sealed and the mixture was stirred at 140° C. for 4 h (max. 21 bar pressure). After cooling to room temperature the mixture was evaporated to dryness and purified by flash chromatography (ethyl acetate/cyclohexane, gradient) to yield in 1.00 g (60%) of a colorless solid. HPLC/MS (purity) 79%. Rt 1.71 min (method D). [M+H]+ 260.1.

General Procedure for Amide Formation g. N-[8-methoxy-5-(oxan-4-yl)quinoxalin-2-yl]-1-(2-methoxyethyl)-1H-pyrazole-4-carboxamide 8-Methoxy-5-(tetrahydro-pyran-4-yl)-quinoxalin-2-ylamine, 79% (100 mg, 0.305 mmol), 1-(2-methoxyethyl)-1H-pyrazole-4-carboxylic acid (67.4 mg, 0.396 mmol), N-(3-dimethylaminopropyl)-N'-ethylcarbodiimide hydrochloride (75.9 mg, 0.396 mmol), 1-hydroxybenzotriazole hydrate (53.5 mg, 0.396 mmol) were dissolved in N,N-dimethylformamide (5.00 ml). N-Ethyldiisopropylamine (0.13 ml, 0.762 mmol) was added at room temperature and the mixture stirred at room temperature for 3 days. The reaction mixture was evaporated to dryness and purified by flash chromatography with acetonitrile/water and the prepurified fractions again with dichloromethane/water to yield in 6.00 mg (5%) of the title compound as a light beige solid. 1H NMR (500 MHz, DMSO-d6) ppm=11.20 (s, 1H), 9.65 (s, 1H), 8.58-8.57 (m, 1H), 8.24-8.23 (m, 1H), 7.51 (d, J=8.2 Hz, 1H), 7.24 (d, J=8.2 Hz, 1H), 4.33 (t, J=5.2 Hz, 2H), 4.02-3.97 (m, 2H), 3.96 (s, 3H), 3.96-3.90 (m, 1H), 3.72 (t, J=5.2 Hz, 2H), 3.56 (td, J=11.5, 2.5 Hz, 2H), 3.26 (s, 3H), 1.87-1.73 (m, 4H). HPLC/MS (purity) 100%. Rt 2.26 min (method D). [M+H]+ 272.1

2. 4-Hydroxy-N-[8-methoxy-5-(pyridin-4-yl)quinoxalin-2-yl]-4-methylpiperidine-1-carboxamide h. 4-(4-Methoxy-2,3-dinitro-phenyl)pyridine

Into a 350-ml pressure tank reactor purged and maintained with an inert atmosphere of argon was placed 1-bromo-4-methoxy-2,3-dinitrobenzene, 95% (5.00 g, 17.2 mmol), 4-(tetramethyl-1,3,2-dioxaborolan-2-yl)pyridine, 95% (4.44 g, 20.6 mmol), Pd(dppf)Cl2 dichloromethane complex, 90% (1.56 g, 1.72 mmol), potassium carbonate (2.99 g, 20.6 mmol, dissolved in water (2 ml)), ethanol (10 ml) and toluene (100 ml). The mixture was stirred for 15 h at 100° C. and after cooling evaporated to dryness. The residue was purified by column chromatography (ethyl acetate/hexane, 80/20) to yield in 4.01 g (81%) of 4-(4-methoxy-2,3-dinitrophenyl)pyridine as a yellow solid. HPLC/MS (purity) 95%. Rt 0.90 min (method E). [M+H]+ 276.1.

General Procedure for Nitro Group Reduction i. 3-Methoxy-6-pyridin-4-yl-benzene-1,2-diamine

Into a 250-ml round-bottom flask was placed Palladium/carbon, 10% (2.13 g, 19.9 mmol), methanol (60 ml) and 4-(4-methoxy-2,3-dinitrophenyl)pyridine, 95% (4.00 g, 13.8 mmol). The mixture was stirred for 15 h under a hydrogen atmosphere at RT. The solids were filtered off and discarded. The filtrate was evaporated to dryness and the residue was purified by column chromatography (ethyl acetate/MeOH, 95/5) to yield in 2.0 g (52%) of 3-methoxy-6-(pyridin-4-yl) benzene-1,2-diamine as a yellow solid. 1H NMR (400 MHz, DMSO-d6) 8.57 (d, J=1.7 Hz, 2H), 7.42 (d, J=1.7 Hz, 2H), 6.46 (d, J=8.4 Hz, 2H), 4.33 (s, 4H), 3.78 (s, 3H). Melting point: 165-166° C. HPLC/MS (purity) 91%. Rt 0.64 min (method A). [M+H]+ 216.0.

j. 8-Methoxy-5-pyridin-4-yl-1H-quinoxalin-2-one

3-Methoxy-6-pyridin-4-yl-benzene-1,2-diamine, 91% (1.77 g, 7.48 mmol) and 3-methoxy-6-pyridin-4-yl-benzene-1,2-diamine, 93% (2.00 g, 8.64 mmol) were dissolved in methanol (80 ml), then ethyl glyoxylate, 50% solution in toluene (9.85 mL, 96.7 mmol) were added at room temperature and the reaction mixture was stirred at 80° C. for 3 h. The mixture was evaporated to dryness and the residue was triturated with ethyl acetate to give a precipitation that—after filtration—was further purified flash chromatography dichloromethane/ethanol, gradient) to yield in 1.80 g (44%) of the title compound as a colorless solid. HPLC/MS (purity) 100%. Rt 1.43 min (method D). [M+H]+ 254.1.

k. 2-Chloro-8-methoxy-5-pyridin-4-yl-quinoxaline

8-Methoxy-5-pyridin-4-yl-1H-quinoxalin-2-one (1,800 g, 7,107 mmol) was dissolved in phosphoryl chloride (32.7 g, 213 mmol) at room temperature and the mixture was stirred at 105° C. for 3 h. After cooling to room temperature mixture was partitioned between saturated aqueous NaHCO3 solution and dichloromethane and stirred additional 1 h at RT. The precipitate was filtered off to give 870 mg (34%) of the title compound as a yellow solid. HPLC/MS (purity) 75%. Rt 1.89 min (method D). [M+H]+ 254.1.

l. 8-Methoxy-5-pyridin-4-yl-quinoxalin-2-ylamine

In a high pressure tube 2-chloro-8-methoxy-5-pyridin-4-yl-quinoxaline, 75% (870 mg, 2.40 mmol) was dissolved THF (20 ml). To this mixture ammonia solution in water, 32% (50 ml) and copper(I)iodide (229 mg, 1.20 mmol) were added, the vessel was sealed and the mixture was stirred at 140° C. for 5 h (max. 21 bar pressure). After cooling to room temperature the mixture was evaporated to dryness and purified by flash chromatography (ethyl acetate/cyclohexane, gradient) to yield in 140 mg (23%) of a colorless solid. HPLC/MS (purity) 100%. Rt 1.33 min (method D). [M+H]+ 253.1.

General Procedure for Urea Formation m. 4-hydroxy-N-[8-methoxy-5-(pyridin-4-yl)quinoxalin-2-yl]-4-methylpiperidine-1-carboxamide 8-Methoxy-5-pyridin-4-yl-quinoxalin-2-ylamine (140 mg, 0.555 mmol) and 1,1'-carbonyldiimidazole (117 mg, 0.721 mmol) were suspended in dichloromethane (4 ml) and stirred at 70° C. for 20 h. 4-Methylpiperidin-4-ol (83.1 mg, 0.721 mmol) was then added at 70° C. and the mixture was stirred for additional 3 h at 70° C. The reaction mixture was evaporated to dryness and directly purified by flash chromatography (water/acetonitrile, gradient). A few drops of 1 N HCl solution was added to the product containing wells to yield in 21.0 mg (9%)—after evaporation to dryness—of the hydrochloride salt of the title compound as a yellow solid. 1H NMR (500 MHz, DMSO-d6) ppm=10.14 (s, 1H), 9.30 (s, 1H), 8.97-8.94 (m, 2H), 8.42-8.39 (m, 2H), 7.97 (d, J=8.3 Hz, 1H), 7.43 (d, J=8.4 Hz, 1H), 4.06 (s, 3H), 3.82 (dt, J=13.4, 4.3 Hz, 2H), 3.34-3.26 (m, 2H), 1.54-1.44 (m, 4H), 1.16 (s, 3H). HPLC/MS (purity) 100%. Rt 1.76 min (method D). [M+H]+ 394.2.

3. 4-Hydroxy-N-[5-methoxy-8-phenylpyrido[3,4-b]pyrazin-3-yl]-4-methylpiperidine-1-carboxamide n. 5-Bromo-2-methoxy-3-nitropyridin-4-amine A mixture of fuming nitric acid (109 ml) and concentrated sulfuric acid (160 mL) was added dropwise to a round bottom flask containing 5-bromo-2-methoxypyridin-4-amine (36.00 g, 177 mmol) with stirring at 0° C. The mixture was stirred for 12 h at room temperature and quenched with ice water (400 ml). The mixture was extracted with DCM (4 times with 500 ml each). The organic phases were combined, washed with brine, dried over anhydrous Na2SO4 and filtered. The filtrate was concentrated under reduced pressure and the residue was purified by flash chromatography (EtOAc/petrol ether, gradient) to yield 5-bromo-2-methoxy-3-nitropyridin-4-amine as a yellow solid (5.54 g, 13%). MS: m/z=249.8 [M+H]+. 1H NMR (300 MHz, DMSO-d6) δ 8.11 (s, 1H), 7.14 (s, 1H), 3.88 (s, 3H).

o. 2-Methoxy-3-nitro-5-phenylpyridin-4-amine

To a solution of 5-bromo-2-methoxy-3-nitropyridin-4-amine (4.95 g, 20.0 mmol) in dioxane (174 ml) was added phenylboronic acid (2.48 g, 20.4 mmol), Pd(dppf)Cl2CH2Cl2 (652 mg, 0.80 mmol), potassium carbonate (5.92 g, 42.9 mmol), and water (37 ml) at room temperature. After bubbling nitrogen into the mixture for 5 minutes, the mixture was stirred for 16 h at 80° C. The solids were filtrated off. The filtrate was concentrated under reduced pressure and the residue was purified by flash chromatography (EtOAc/petrol ether, gradient) to yield 2-methoxy-3-nitro-5-phenylpyridin-4-amine as a yellow solid (3.96 g, 81%). MS: m/z=246.3 [M+H]+.

p. 2-Methoxy-5-phenylpyridine-3,4-diamine

To a solution of 2-methoxy-3-nitro-5-phenylpyridin-4-amine (3.96 g, 16.2 mmol) in MeOH (138 ml) was placed Palladium/carbon, 10% (515 mg, 4.84 mmol). The mixture was stirred for 16 h at room temperature under H2 atmosphere. When the reaction was done, the solids were filtrate out. The filtrate was concentrated under vacuum to yield 2-methoxy-5-phenylpyridine-3,4-diamine as a yellow solid (3.37 g, 97%). MS: m/z=216.3 [M+H]+.

q. 5-Methoxy-8-phenylpyrido[3,4-b]pyrazin-3-ol

To a solution of 2-methoxy-5-phenylpyridine-3,4-diamine (3.37 g, 15.6 mmol) in methanol (181 ml) was added ethyl 2-oxoacetate (10.86 g, 106 mmol) at room temperature. The mixture was stirred for 3 h at 80° C. After cooling to room temperature, it was concentrated under reduced pressure and the residue was purified by flash chromatography (EtOAc/petrol ether, gradient). Two regio-isomers were collected and the first fraction was identified as 5-methoxy-8-phenylpyrido[3,4-b]pyrazin-3-ol as a yellow solid (750 mg, 19%). MS: m/z=254.0 [M+H]+.

r. 5-Methoxy-8-phenylpyrido[3,4-b]pyrazin-3-yl 4-methylbenzene-1-sulfonate

To a solution of 5-methoxy-8-phenylpyrido[3,4-b]pyrazin-3-ol (750 mg, 2.97 mmol) in dichloromethane (24 ml) was added 4-methylbenzene-1-sulfonyl chloride (616 mg, 3.25 mmol), 4-dimethylaminopyridine (39 mg, 0.28 mmol), and triethylamine (414 mg, 4.14 mmol) at room temperature. The solution was stirred for 2 h at room temperature and then quenched with water (50 ml). The mixture was extracted with dichloromethane (3 times with 150 ml) and the organic phases were combined, washed with brine and dried over anhydrous Na2SO4. The solvent was removed under reduced pressure and the residue was purified by flash chromatography (EtOAc/petrol ether, gradient) to yield 5-methoxy-8-phenylpyrido[3,4-b]pyrazin-3-yl 4-methylbenzene-1-sulfonate as a green solid (806 mg, 67%). MS: m/z=408.2 [M+H]+.

s. 5-Methoxy-8-phenylpyrido[3,4-b]pyrazin-3-amine

To a solution of 5-methoxy-8-phenylpyrido[3,4-b]pyrazin-3-yl 4-methylbenzene-1-sulfonate (806 mg, 1.97 mmol) in dioxane (85 ml) was added tert-butyl carbamate (463 mg, 3.94 mmol), Pd(OAc)2 (47 mg, 0.2 mmol), XPhos (198 mg, 0.39 mmol), and Cs2CO3 (966 mg, 2.97 mmol). After bubbling nitrogen into the mixture for 5 minutes, the mixture was stirred for 16 h at 100° C. When the reaction was done, the solids were filtrated off. The filtrate was concentrated under reduced pressure and the residue was purified by flash chromatography (EtOAc/petrol ether, gradient) to yield 5-methoxy-8-phenylpyrido[3,4-b]pyrazin-3-amine as a black solid (185 mg, 37%). MS: m/z=253.3 [M+H]+.

t. Phenyl N-[5-methoxy-8-phenylpyrido[3,4-b]pyrazin-3-yl]

To a solution of 5-methoxy-8-phenylpyrido[3,4-b]pyrazin-3-amine (120 mg, 0.48 mmol) in THF (50 ml) was added sodium carbonate (252 mg, 2.38 mmol), phenyl chloroformate (744 mg, 4.76 mmol), and pyridine (188 mg, 2.38 mmol) at room temperature. The mixture was stirred for 6 h at 50° C. When the reaction was done, the solids were filtered out. The filtrate was concentrated under reduced pressure to yield phenyl N-[5-methoxy-8-phenylpyrido[3,4-b]pyrazin-3-yl]carbamate as a white solid (300 mg, crude). MS: m/z=373.2 [M+H]+.

u. 4-Hydroxy-N-[5-methoxy-8-phenylpyrido[3,4-b]pyrazin-3-yl]-4-methylpiperidine-1-carboxamide To a solution of phenyl N-[5-methoxy-8-phenylpyrido[3,4-b]pyrazin-3-yl]carbamate (100 mg, crude) in THF (10 ml) was added 4-methylpiperidin-4-ol (31 mg, 0.27 mmol), and diisopropylethylamine (34.0 mg, 0.27 mmol) at room temperature. The solution was stirred for 12 h at 60° C. After cooling to the room temperature, the reaction was quenched by the addition of water (20 ml). The mixture was extracted with DCM (3 times with 50 ml). The organic phases were combined, washed with brine, dried over anhydrous Na2SO4 and filtered. The filtrate was concentrated under reduced pressure and the residue was purified by prep-HPLC under the following conditions: Column, XBridge Prep C18 OBD Column, 19×150 mm 5 um; MeCN in water (with 10 mmol/l NH4HCO3+0.1% NH3.H2O), 30% to 50% gradient in 8 min; Detector, UV 254/220 nm to yield in 4-hydroxy-N-[5-methoxy-8-phenylpyrido[3,4-b]pyrazin-3-yl]-4-methylpiperidine-1-carboxamide as a yellow solid (30.0 mg, 47% for 2 steps). HPLC: 99.3% purity, room temperature=4.14 min. MS: m/z=394.3 [M+H]+. 1H NMR (400 MHz, DMSO-d6) δ 10.22 (s, 1H), 9.38 (s, 1H), 8.19 (s, 1H), 7.68-7.60 (m, 2H), 7.54-7.38 (m, 3H), 4.37 (s, 1H), 4.10 (s, 3H), 3.87-3.76 (m, 2H), 3.34-3.24 (m, 2H), 1.56-1.42 (m, 4H), 1.16 (s, 3H).

HPLC Methods:

Method A:
Shimadzu LCMS-2020; Column: Poroshell HPH-C18, 3.0×50 mm, 2.7 μm; mobile phase A: Water/5 mM NH4HCO3, mobile phase B: acetonitrile; flow rate: 1.0 mL/min; Gradient: 10% B to 95% B in 2.2 min, hold 1.0 min; wave length: 254 nm Method B:
Shimadzu LCMS-2020; Column: Poroshell HPH-C18, 3.0×50 mm, 2.7 μm; mobile phase A: Water/5 mM NH4HCO3, mobile phase B: acetonitrile; flow rate: 1.3 mL/min; Gradient: 10% B to 95% B in 2.1 min, hold 0.6 min; wave length: 254 nm Method C:
Shimadzu LCMS-2020; Column: Shim-pack XR-ODS, 3.0×50 mm, 2.2 μm; mobile phase A: Water/0.05% TFA, mobile phase B: acetonitrile/0.05% TFA; flow rate: 1.2 mL/min; Gradient: 5% B to 100% B in 2.2 min, hold 1.0 min; wave length: 254 nm Method D:
Agilent Technologies 1200 series; column: Chromolith Performance RP18e; 100×3 mm; mobile phase AA: water/0.1% TFA, mobile phase B: acetonitrile/0.1% TFA; Gradient: 1% B for 0.2 min, 1% B to 100% B in 3.8 min, hold 0.4 min; flow rate: 2 mL/min, wave length: 220 nm Method E:
Shimadzu LCMS-2020; Column: Shim-pack XR-ODS, 3.0×50 mm, 2.2 μm; mobile phase A: Water/0.05% TFA, mobile phase B: acetonitrile/0.05% TFA; flow rate: 1.2 mL/min; Gradient: 5% B to 100% B in 2.0 min, hold 0.5 min; wave length 254 nm

EXAMPLE 3: TESTING COMPOUNDS OF THE PRESENT INVENTION FOR INHIBITORY ACTIVITIES AGAINST HUMAN ADENOSINE RECEPTORS IN RECOMBINANT CELLS

The functional activities of human $A_{2A}$, $A_{2B}$, $A_1$ and $A_3$ receptors were determined by quantification of cAMP, being the second messenger for adenosine receptors. For this purpose recombinant HEK293 cells, expressing either human $A_{2A}$ or $A_{2B}$ receptors (both Gs coupled were seeded into 394-well microtiter plates, test compounds and agonist (NECA) were added. After a 15 min incubation, HTRF reagents (cAMP dynamic 2, Cis Bio) were added and the cellular cAMP levels were determined using the ENVISION (Perkin Elmer) plate reader.

For human $A_1$ and $A_3$ receptors, recombinant CHO cells, expressing either $A_1$ or A3-receptor, were used. As both receptors couple to Gi proteins, the assay protocol was adapted:

Cells were seeded into 384-well plates, forskolin, test compounds and agonists (CPA for $A_1$- and IB-MECA for $A_3$-receptor) were added. After 30 min incubation, HTRF reagents (cAMP dynamic 2, Cis Bio) were added and the cellular cAMP levels were determined using the ENVISION (Perkin Elmer) plate reader.

Obtained raw data were normalized against the inhibitor control and the neural control (DMSO) and the normalized data were fitted using GeneData software.

The compounds of the present invention show a high selectivity for adenosine $A_{2A}$ and $A_{2B}$ receptors over adenosine $A_1$ and $A_3$ receptors (see e.g. the data of some examples of the compounds of the present invention in table 4)

Particularly, in contrast to the known adenosine $A_{2A}$ receptor antagonist Tozadenant and similar benzothiazole derivatives, the compounds of the present invention surprisingly show an $A_{2A}/A_{2B}$ dual activity (see table 4) which is preferred for the treatment and/or prevention of hyperproliferative and infectious diseases and disorders as it is disclosed above or the compounds of the present invention show at least a high $A_{2A}$ inhibitory activity together with the other surprising advantages disclosed herein leading to a high efficacy in the treatment and/or prevention of hyperproliferative and infectious diseases and disorders.

TABLE 4

| No. | Functional A2A receptor activity, HEK293, cAMP, IC50 [µM] | Functional A2B receptor activity, HEK293, cAMP, IC50 [µM] | Functional A1 receptor activity, CHO, cAMP, IC50 [µM] | Functional A3 receptor activity, CHO, cAMP, IC50 [µM] |
|---|---|---|---|---|
| 1 | B | D | D | D |
| 2 | B | D | D | D |
| 5 | B | D | D | D |
| 10 | B | D | C | D |
| 13 | B | D | D | D |
| 14 | B | D | D | D |
| 15 | B | D | D | |
| 16 | B | D | D | D |
| 17 | B | D | D | D |
| 18 | B | | D | |
| 20 | A | D | D | |
| 21 | B | C | C | D |
| 23 | B | D | D | D |
| 27 | B | D | C | D |
| 28 | B | D | C | D |
| 29 | B | C | D | D |
| 30 | B | D | D | |
| 31 | A | C | D | D |
| 32 | B | D | D | D |
| 34 | B | C | C | D |
| 36 | A | C | C | D |
| 37 | A | D | D | D |
| 38 | B | D | D | D |
| 39 | B | D | D | D |
| 40 | B | D | D | D |
| 42 | A | C | D | D |
| 43 | B | D | D | C |
| 44 | A | C | C | D |
| 45 | A | B | B | C |
| 46 | B | C | D | C |
| 47 | A | B | B | D |
| 48 | A | B | C | D |
| 50 | A | D | D | D |
| 51 | A | D | D | |
| 52 | A | C | C | D |
| 56 | A | D | D | |
| 60 | B | D | D | |
| 62 | B | D | C | |
| 64 | B | D | D | |
| 68 | A | D | D | |
| 78 | A | C | D | |
| 86 | A | C | D | D |
| 88 | B | D | D | C |
| 102 | A | B | C | C |
| 103 | A | D | D | |
| 104 | A | | | |
| 105 | A | B | C | C |
| 106 | A | B | C | D |

TABLE 4-continued

| No. | Functional A2A receptor activity, HEK293, cAMP, IC50 [µM] | Functional A2B receptor activity, HEK293, cAMP, IC50 [µM] | Functional A1 receptor activity, CHO, cAMP, IC50 [µM] | Functional A3 receptor activity, CHO, cAMP, IC50 [µM] |
|---|---|---|---|---|
| 108 | B | D | D | |
| 109 | A | D | C | |
| 112 | B | | D | |
| 114 | B | D | C | |
| 115 | B | | | |
| 116 | B | D | C | |
| 117 | B | D | D | |
| 118 | B | D | D | D |
| 119 | B | D | D | |
| 120 | A | B | C | C |
| 121 | B | C | C | C |
| 122 | B | | D | D |
| 123 | A | B | C | C |
| 124 | A | D | C | C |
| 125 | B | | C | |
| 126 | A | B | C | C |
| 128 | B | | D | C |
| 129 | A | B | | |
| 130 | A | B | D | |
| 131 | A | B | C | C |
| 132 | A | B | C | |
| 134 | A | B | C | D |
| 135 | A | B | B | |
| 136 | A | B | C | D |
| 137 | A | D | C | |
| 138 | B | B | A | D |
| 139 | B | D | D | |
| 140 | A | B | C | |
| 141 | B | B | C | C |
| 142 | A | D | D | |
| 143 | B | D | D | |
| 144 | B | | D | |
| 145 | B | | D | |
| 146 | B | | D | |
| 147 | A | B | C | C |
| 148 | A | B | C | D |
| 149 | B | | D | C |
| 151 | B | D | C | D |
| 152 | B | | | D |
| 156 | B | D | C | D |
| 158 | B | | D | |
| 159 | B | B | C | |
| 160 | B | B | D | |
| 161 | B | | D | |

A means $IC_{50}$ value is < 10 nM, B means $IC_{50}$ value is < 100 nM, C means $IC_{50}$ value is < 1 µM, D means $IC_{50}$ value is > 1 µM.

EXAMPLE 4: TESTING THE EFFECTS OF THE COMPOUNDS OF THE PRESENT INVENTION AGAINST ENDOGENOUS HUMAN $A_{2A}$ RECEPTOR

The endogenous functional activity of the Gs-coupled human $A_{2A}$ receptor was measured in T cells, where this receptor is highly expressed. Determination of receptor activity was done by quantification of cAMP, which is a second messenger for adenosine receptors.

In short, human pan T cells were isolated from human PBMC (MACS Pan T Cell Isolation Kit, Miltenyi Biotec) that have been derived from fresh whole blood. The T cells were seeded in 384-well microtiter plates and treated with test compounds. After 10 min incubation at room temperature, the $A_{2A}$ adenosine receptor agonist CGS-21680 was added, and the plates were incubated for another 45 min. Finally, HTRF reagents (cAMP Femto Kit, CisBio) were added to the wells, and after 1 h cellular cAMP levels were determined using the ENVISION (Perkin Elmer) plate reader.

The obtained raw data were normalized against the inhibitor control and the neutral control (DMSO) and the normalized data were fitted using Genedata Screener software.

The compounds of the present invention show that they are able to inhibit the $A_{2A}$ receptor expressed in human T cells which incubated with the $A_{2A}$ adenosine receptor agonist CGS-21680 (as measured by quantification of cAMP), which is preferred for the treatment and/or prevention of hyperproliferative and infectious diseases and disorders as it is disclosed above. Therefore, the compounds of the present invention surprisingly are able to prevent immunosuppression and thus are able to support anti-tumor T cell induced inhibition of tumor growth, reduction or destruction of metastases and prevention of neovascularization.

EXAMPLE 5: TESTING THE PHARMACOKINETIC PROPERTIES OF THE COMPOUNDS OF THE PRESENT INVENTION IN RAT AND MOUSE

The objective of the study was to obtain information on the pharmacokinetic properties of the compounds of the present invention in female Wistar rats/mice following single intravenous and oral administration.
Material and Methods:
Animal Experiments (In-Life Phase)

Female Wistar rats/mice (n=6) received either a single intravenous (bolus) injection or an oral administration (by gavage) of the tested compound. Doses of 0.2 and 10 mg/kg (per compound) were given intravenously and per os, respectively, as a solution in DMSO (0.2%)/PEG 200 (40%)/water for iv administration and as a suspension in Methocel (0.5%)/Tween 20 (0.25%) in water for oral dosing. Consecutive blood samples were taken sub-lingually under isoflurane inhalation from 3 animals per route of administration after 0.1 (only iv), 0.25 (only po), 0.5, 1, 2, 4, 6 and 24 h and were further processed to obtain plasma. Also, urine and feces samples of 3 rats per route of administration were collected over the time interval from 0-24 h and were pooled for analysis.
Bioanalytics:

The concentrations of the compounds in plasma, feces were quantified using an UPLC method with tandem mass spectrometric detection (LC-MS/MS) previously developed at the 'Institute of Drug Metabolism and Pharmacokinetics'. The LCMS/MS system consisted of a Waters Acquity UPLC coupled to an AB Sciex mass spectrometer API 5500 Q-trap. The UPLC separation was carried out on a reversed phase column (HSS T3, 1.8 µM, 2.1×50 mm) using a mobile phase gradient with 0.1% formic acid and acetonitrile as eluents. The detection of the compounds was performed using multiple reaction monitoring in the positive ionization mode. Plasma samples were spiked with internal standard (20 µl) and the analyte was extracted from the matrix using tertiary-butyl methyl ether (tBME). The organic phase was evaporated to dryness under a stream of nitrogen. The residue was dissolved in acetonitrile/0.1% formic acid for LC-MS/MS analysis. Feces samples were homogenized with 4-times their volume of an ethanol/water mixture (4:1, v/v). Aliquots of the aqueous-ethanolic extracts were spiked with internal standard, diluted with acetonitrile/water (1:1, v/v) and directly injected into the LC-MS/MS system.
Pharmacokinetic Evaluation:

Pharmacokinetic parameters $C_{max}$ and $t_{max}$ were taken from the observed data. Area under the curve (AUC), clearance (CL), volume (V), half-life ($t_{1/2}$), F and all dose-normalized values were calculated using the custom-made software 'DDS-TOX'. 'DDS-TOX' values were evaluated for several compounds and shown comparable to the values given by the validated software WinNonLin. AUC values were calculated by non-compartmental analysis using the linear up/log down method. Numerical data for mean plasma concentrations and derived pharmacokinetic parameters were rounded to 3 significant digits for presentation. Oral bioavailability and excretion data—expressed as % of dose—are displayed using 2 significant digits.

In comparison with the known adenosine $A_{2A}$ receptor antagonist Tozadenant and similar benzothiazole derivatives, the compounds of the present invention surprisingly show better pharmacokinetic properties in mouse as the animal model relevant for cancer (see table 6), which is preferred for the treatment and/or prevention of hyperproliferative and infectious diseases and disorders as it is disclosed above.

TABLE 6

| | | | | | | |
|---|---|---|---|---|---|---|
| | | PK data in mouse | | | | |
| Name, No. | Structure | CL [L/h/kg] | t1/2 [h] | Vss [L/kg] | Feces iv [%] | CMax (iv) @ 1 mg/kg [ng/ml] |
| Tozadenant | | 88.68 | 0,184 | 2,03 | 23 @ 0.2 | 337 |

TABLE 6-continued
PK data in mouse
| Name, No. | Structure | CL [L/h/kg] | t1/2 [h] | Vss [L/kg] | Feces iv [%] | CMax (iv) @ 1 mg/kg [ng/ml] |
|---|---|---|---|---|---|---|
| 2 | 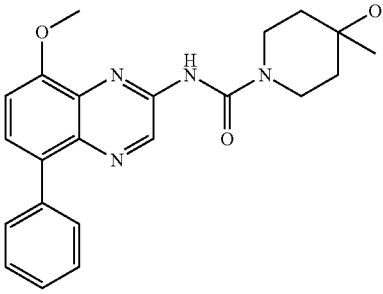 | 0.339 | 2.37 | 1.13 | 12.5 @ 0.2 | 732 |
| 5 | 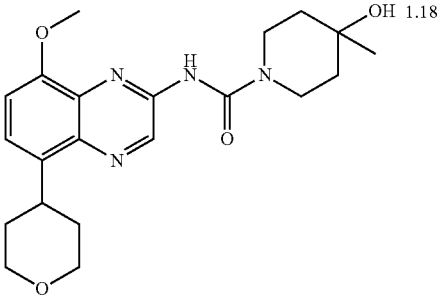 | 1.18 | 0.92 | 1.24 | 4.2 @ 0.2 | 908 |
| 10 | 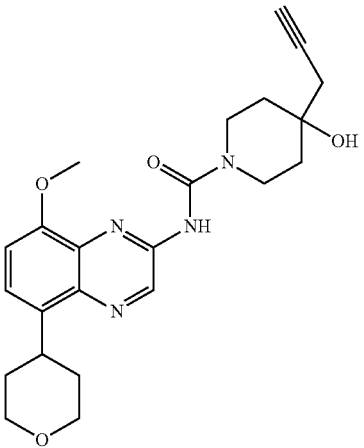 [SMILES: C#CCC1(O)CCN(C(=O)Nc2cnc3c(C4CCOCC4)ccc(OC)c3n2)CC1] | 1.09 | 0.55 | 0.811 | 1.8 @ 0.2 | 1 090 |

TABLE 6-continued

PK data in mouse

| Name, No. | Structure | CL [L/h/kg] | t1/2 [h] | Vss [L/kg] | Feces iv [%] | CMax (iv) @ 1 mg/kg [ng/ml] |
|---|---|---|---|---|---|---|
| 20 | (structure) | 1.55 | 0.338 | 0.715 | <1 @ 0.2 | 1 220 |
| 27 | (structure) | 0.227 | 2.56 | 0.82 | 6.2 @ 0.2 | 983 |

EXAMPLE 6: TESTING THE EFFECT OF THE COMPOUNDS OF THE PRESENT INVENTION ON MOUSE T CELLS

Background:

Adenosine (Ado) in tumor microenvironment can inhibit T cell activity by signaling through $A_{2A}$ receptors and suppress cytokine secretion by T cells. $A_{2A}$ specific agonists like CGS-21680 does similar job of inhibition of T cell cytokine secretion in vitro and in vivo. Potential $A_{2A}$ antagonists or $A_{2A}/A_{2B}$ dual antagonists can rescue T cells from this inhibition. Herein, we describe the in vitro system we established using Pan T cells from mouse spleens to screen potential $A_{2A}$ antagonists or $A_{2A}/A_{2B}$ dual antagonists for their activity. The method described involves the use of CD3/CD28 pre-coated beads to stimulate Pan T cells purified from mouse splenocytes, combined with the addition of $A_{2A}$ agonist along with potential $A_{2A}$ or $A_{2A}/A_{2B}$ dual antagonists to evaluate potentiation of T cell cytokine production.

Assay Description:

Briefly, mouse Pan T cells are purified from spleens of BALB/c mice using Pan T cell isolation kit Mouse II (MACS Miltenyi biotech Cat #Order no. 130-095-130) according to manufacturer's protocol. The purified T cells are seeded in Nunc™ 96-Well Polystyrene Round Bottom Microwell Plates in RPMI medium with 10% heat inactivated fetal bovine serum. The cells are rested at 37° C. for 1 h before activating with CD3/CD28 pre-coated beads (Dynabeads™ Mouse T-Activator CD3/CD28; Cat #11456D). After 30 min the cells are treated with varying doses of test antagonist(s). The cells are incubated for additional 30 min at 37° C. before treating with $A_{2A}$ agonist CGS-21680 (1 μM) or neutral control (DMSO). After 24 h incubation IL-2 levels in the supernatants and after 48 h incubation IFN-γ levels in the supernatants are measured by ELISAs according to manufacturer's protocol (R&D systems Cat #DY402 (IL-2); DY485 (IFN-γ)). Once the concentrations are calculated, the difference of cytokine concentration of DMSO control and agonist alone control is calculated (called Δ) and the percentage of rescue by each concentration of antagonist is calculated by using Microsoft Excel. These percentages of cytokine rescue in a dose dependent manner of antagonist is plotted in GraphPad Prism software and $IC_{50}$ is calculated.

In contrast to the known adenosine $A_{2A}$ receptor antagonist Tozadenant, the compounds of the present invention show that they are able to rescue T cells from inhibition and are able to prevent the suppression of cytokine secretion as induced by adenosine or $A_{2A}$ specific agonists like CGS-2168 (see table 7), which is preferred for the treatment and/or prevention of hyperproliferative and infectious diseases and disorders as it is disclosed above. Therefore, the compounds of the present invention surprisingly are able to prevent immunosuppression and thus are able to support anti-tumor T cell induced inhibition of tumor growth, reduction or destruction of metastases and prevention of neovascularization.

TABLE 7

| No. | Name | Structure | Mouse T-Cell IL-2 [nM] | Mouse IFN-γ [nM] |
|---|---|---|---|---|
|  | Tozadenant |  | NA (< 50% rescue) | NA (< 50% rescue) |
| 2 | 4-Hydroxy-4-methyl-piperidine-1-carboxylic acid (8-methoxy-5-phenyl-quinoxalin-2-yl)-amide | 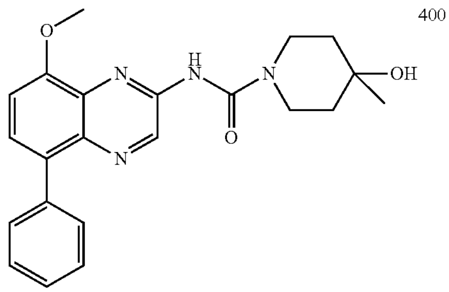 | 400 | 600 |
| 27 | 4-Hydroxy-4-methyl-piperidine-1-carboxylic acid (5-methoxy-8-phenyl-pyrido[3,4-b]pyrazin-3-yl)-amide | 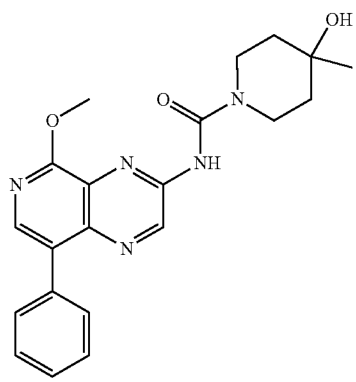 [SMILES: COc1ncc(-c2ccccc2)c2ncc(NC(=O)N3CCC(C)(O)CC3)nc12] | 375 | 333 |

EXAMPLE 7: INJECTION VIALS

A solution of 100 g of a compound of the present invention and 5 g of disodium hydrogenphosphate in 3 l of bidistilled water is adjusted to pH 6.5 using 2 N hydrochloric acid, filtered under sterile conditions, transferred into injection vials, lyophilised under sterile conditions and sealed under sterile conditions. Each injection vial contains 5 mg of a compound of the present invention.

EXAMPLE 8: SOLUTION

A solution is prepared from 1 g of a compound of the present invention, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation.

EXAMPLE 9: AMPOULES

A solution of 1 kg of a compound of the present invention in 60 l of bidistilled water is filtered under sterile conditions, transferred into ampoules, lyophilised under sterile conditions and sealed under sterile conditions. Each ampoule contains 10 mg of a compound of the present invention.

The invention claimed is:
1. A compound of formula I,

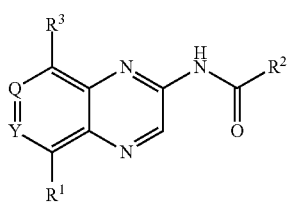

I wherein
Q, Y are independently of one another CH or N,
$R^1$ is Hal or linear or branched alkyl having 1-10 C atoms which is unsubstituted or mono-, di- or trisubstituted by R⁴ and in which 1-4 C atoms may be replaced, independently of one another, by O, S, SO, SO₂, NH, NCH₃, —OCO—, —NHCONH—, —NHCO—, —NR⁵SO₂R⁶—, —COO—, —CONH—, —NCH₃CO—, —CONCH₃—, —C≡C— groups and/or —CH═CH— groups, and/or 1-10 H atoms may be replaced by F and/or Cl, or mono- or bicyclic cyclic alkyl having 3-7 C atoms which is unsubstituted or mono-, di- or trisubstituted by R⁴ and in which 1-4 C atoms may be replaced, independently of one another, by O, S, SO, SO₂, NH, NCH₃, —OCO—, —NHCONH—, —NHCO—, —NR⁵SO₂R⁶—, —COO—, —CONH—, —NCH₃CO—, —CONCH₃—, —C≡C— groups and/or by —CH═CH— groups and/or 1-10 H atoms may be replaced by F and/or Cl, or mono- or bicyclic heteroaryl, heterocyclyl, aryl or cyclic alkylaryl containing 3 to 14 carbon atoms and 0-4 heteroatoms, independently selected from the group consisting of N, O and S, which is unsubstituted or mono-, di- or trisubstituted by R⁴, R² is linear or branched alkyl having 1-10 C atoms which is unsubstituted or mono-, di- or trisubstituted by R⁴ and in which 1-4 C atoms may be replaced, independently of one another, by O, S, SO, SO₂, NH, NCH₃, —OCO—, —NHCONH—, —NHCO—, —NR⁵SO₂R⁶—, —COO—, —CONH—, —NCH₃CO—, —CONCH₃—, —C≡C— groups and/or —CH═CH— groups, and/or 1-10 H atoms may be replaced by F and/or Cl, or cyclic alkyl having 3-7 C atoms which is unsubstituted or mono-, di- or trisubstituted by R⁴ and in which 1-4 C atoms may be replaced, independently of one another, by O, S, SO, SO₂, NH, NCH₃, —OCO—, —NHCONH—, —NHCO—, —NR⁵SO₂R⁶—, —COO—, —CONH—, —NCH₃CO—, —CONCH₃—, —C≡C— groups and/or by —CH═CH— groups and/or 1-11 H atoms may be replaced by F and/or Cl, or mono- or bicyclic heteroaryl, heterocyclyl, aryl or cyclic alkylaryl containing 3 to 14 carbon atoms and 0-4 heteroatoms, independently selected from the group consisting of N, O and S, which is unsubstituted or mono-, di- or trisubstituted by R⁴, R³ is linear or branched alkyl or O-alkyl having 1-6 C atoms or cyclic alkyl having 3-6 C atoms, which is unsubstituted or mono-, di- or trisubstituted by H, ═S, ═NH, ═O, OH, cyclic alkyl having 3-6 C atoms, COOH, Hal, NH₂, SO₂CH₃, SO₂NH₂, CN, CONH₂, NHCOCH₃, NHCONH₂ or NO₂, R⁴ is H, R⁵, ═S, ═NR⁵, ═O, OH, COOH, Hal, NH₂, SO₂CH₃, SO₂NH₂, CN, CON H₂, NHCOCH₃, NHCONH₂, NO₂, or linear or branched alkyl having 1-10 C atoms which is unsubstituted or mono-, di- or trisubstituted by R⁵ and in which 1-4 C atoms may be replaced, independently of one another, by O, S, SO, SO₂, NH, NCH₃, —OCO—, —NHCONH—, —NHCO—, —NR⁵SO₂R⁶—, —COO—, —CONH—, —NCH₃CO—, —CONCH₃—, —C≡C— groups and/or —CH═CH— groups, and/or 1-10 H atoms may be replaced by F and/or Cl, or mono- or bicyclic cyclic alkyl having 3-7 C atoms which is unsubstituted or mono-, di- or trisubstituted by R⁵ and in which 1-4 C atoms may be replaced, independently of one another, by O, S, SO, SO₂, NH, NCH₃, —OCO—, —NHCONH—, —NHCO—, —NRSO₂R⁴—, —COO—, —CONH—, —NCH₃CO—, —CONCH₃—, —C≡C— groups and/or by —CH═CH— groups and/or 1-10 H atoms may be replaced by F and/or Cl, or mono- or bicyclic heteroaryl, heterocyclyl, aryl or cyclic alkylaryl containing 3 to 14 carbon atoms and 0-4 heteroatoms, independently selected from the group consisting of N, O and S, which is unsubstituted or mono-, di- or trisubstituted by R⁵, R⁵, R⁶ are independently of one another ═S, ═NH, ═O, OH, COOH, Hal, NH₂, SO₂CH₃, SO₂NH₂, CN, CONH₂, NHCOCH₃, NHCONH₂, NO₂ or linear or branched alkyl having 1-10 C atoms in which 1-4 C atoms may be replaced, independently of one another, by O, S, SO, SO₂, NH, NCH₃, —OCO—, —NHCONH—, —NHCO—, —COO—, —CONH—, —NCH₃CO—, —CONCH₃—, —C≡C— groups and/or —CH═CH— groups, and/or 1-10 H atoms may be replaced by F and/or Cl, Hal is F, C, Br, or I, or a physiologically acceptable salt, derivative, solvate, prodrug r stereoisomer thereof.

2. The compound according to claim 1, wherein

R¹ is linear or branched alkyl having 1-10 C atoms which is unsubstituted or mono-, di- or trisubstituted by R⁴ and in which 1-4 C atoms may be replaced, independently of one another, by O, S, SO, SO₂, NH, NCH₃, —OCO—, —NHCONH—, —NHCO—, —NR⁵SO₂R⁶—, —COO—, —CONH—, —NCH₃CO—, —CONCH₃—, —C≡C— groups and/or —CH═CH— groups, and/or 1-10 H atoms may be replaced by F and/or Cl, or one of the following structures:

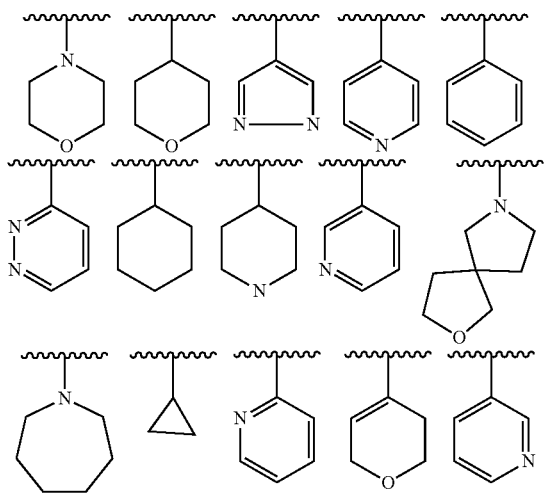

which is unsubstituted or mono-, di- or trisubstituted with R⁴.

3. The compound according to claim 1, wherein

Q is CH or N, and

Y is CH.

4. The compound according to claim 1, wherein R² is one of the following structures:

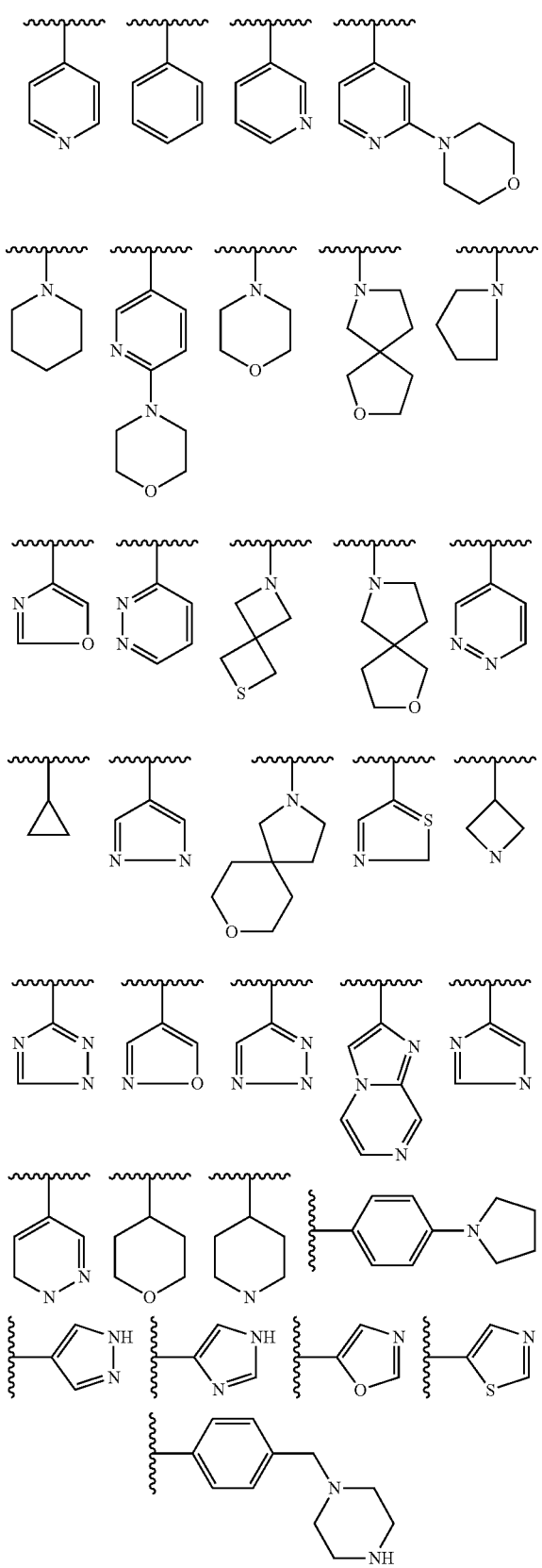

which is unsubstituted or mono-, di- or trisubstituted with R⁵.

5. The compound according to claim 1, wherein R³ one of the following structures

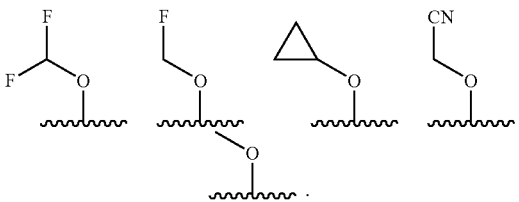

6. The compound according to claim 1, wherein R³ is OMe.

7. A compound selected from the group consisting of:

| No. | IUPAC-Name |
| --- | --- |
| 1 | N-[8-methoxy-5-(oxan-4-yl)quinoxalin-2-yl]-2-oxa-7-azaspiro[4.4]nonane-7-carboxamide |
| 2 | 4-hydroxy-N-[8-methoxy-5-(pyridin-4-yl)quinoxalin-2-yl]-4-methylpiperidine-1-carboxamide |
| 3 | 3-hydroxy-N-[8-methoxy-5-(oxan-4-yl)quinoxalin-2-yl]-3-methylpyrrolidine-1-carboxamide |
| 4 | N-[8-methoxy-5-(oxan-4-yl)quinoxalin-2-yl]-2-methyl-1,3-oxazole-4-carboxamide |
| 5 | 4-(hydroxymethyl)-N-[8-methoxy-5-(oxan-4-yl)quinoxalin-2-yl]-4-methylpiperidine-1-carboxamide |
| 6 | N-[8-methoxy-5-(oxan-4-yl)quinoxalin-2-yl]-2,2-dioxo-2lambda6-thia-6-azaspiro[3.3]heptane-6-carboxamide |
| 7 | 6-methoxy-N-[8-methoxy-5-(oxan-4-yl)quinoxalin-2-yl]pyridazine-3-carboxamide |
| 8 | N-[8-methoxy-5-(oxan-4-yl)quinoxalin-2-yl]-1-(2-methoxyethyl)-1H-pyrazole-4-carboxamide |
| 9 | 4-hydroxy-N-(8-methoxy-5-phenylquinoxalin-2-yl)-4-(prop-2-yn-1-yl)piperidine-1-carboxamide |
| 10 | 3-hydroxy-N-(8-methoxy-5-phenylquinoxalin-2-yl)-3-methylpyrrolidine-1-carboxamide |
| 11 | 4-(hydroxymethyl)-N-(8-methoxy-5-phenylquinoxalin-2-yl)-4-methylpiperidine-1-carboxamide |
| 12 | N-(8-methoxy-5-phenylquinoxalin-2-yl)-8-oxa-2-azaspiro[4.5]decane-2-carboxamide |
| 13 | N-(8-methoxy-5-phenylquinoxalin-2-yl)-2-oxa-7-azaspiro[4.4]nonane-7-carboxamide |
| 14 | N-(8-methoxy-5-phenylquinoxalin-2-yl)-2,2-dioxo-2lambda6-thia-6-azaspiro[3.3]heptane-6-carboxamide |
| 15 | 4-Hydroxy-4-methyl-piperidine-1-carboxylic acid (5-methoxy-8-phenyl-pyrido[3,4-b]pyrazin-3-yl)-amide |
| 16 | 3-Hydroxy-3-methyl-pyrrolidine-1-carboxylic acid (5-methoxy-8-phenyl-pyrido[3,4-b]pyrazin-3-yl)-amide |
| 17 | 4-Hydroxymethyl-4-methyl-piperidine-1-carboxylic acid (5-methoxy-8-phenyl-pyrido[3,4-b]pyrazin-3-yl)-amide |
| 18 | N-[8-methoxy-5-(oxan-4-yl)quinoxalin-2-yl]-8-oxa-2-azaspiro[4.5]decane-2-carboxamide |
| 19 | N-[8-methoxy-5-(oxan-4-yl)quinoxalin-2-yl]acetamide |
| 20 | 2,2,2-trifluoro-N-[8-methoxy-5-(oxan-4-yl)quinoxalin-2-yl]acetamide |
| 21 | 4-Dimethylaminomethyl-N-(5-methoxy-8-phenyl-pyrido[3,4-b]pyrazin-3-yl)-benzamide |
| 22 | 4-Hydroxy-4-prop-2-ynyl-piperidine-1-carboxylic acid (5-methoxy-8-phenyl-pyrido[3,4-b]pyrazin-3-yl)-amide |
| 23 | 4-Methoxymethyl-N-(5-methoxy-8-phenyl-pyrido[3,4-b]pyrazin-3-yl)-benzamide |
| 24 | 1-(2-Methoxy-ethyl)-1H-pyrazole-4-carboxylic acid (5-methoxy-8-phenyl-pyrido[3,4-b]pyrazin-3-yl)-amide |
| 25 | 6-hydroxy-N-[8-methoxy-5-(oxan-4-yl)quinoxalin-2-yl]pyridazine-4-carboxamide |
| 26 | 8-methoxy-5-(oxan-4-yl)quinoxalin-2-amine |
| 27 | (3S)-3-hydroxy-N-[8-methoxy-5-(oxan-4-yl)quinoxalin-2-yl]-3-methylpyrrolidine-1-carboxamide |
| 28 | (3R)-3-hydroxy-N-[8-methoxy-5-(oxan-4-yl)quinoxalin-2-yl]-3-methylpyrrolidine-1-carboxamide |
| 29 | 4-hydroxy-N-[8-methoxy-5-(2-methylphenyl)quinoxalin-2-yl]-4-methylpiperidine-1-carboxamide |
| 30 | N-(8-methoxy-5-phenylquinoxalin-2-yl)-1-(2-methoxyethyl)-1H-pyrazole-4-carboxamide |

| No. | IUPAC-Name |
|---|---|
| 31 | N-(8-methoxy-5-phenylquinoxalin-2-yl)-2-methyl-1,3-oxazole-4-carboxamide |
| 32 | N-(8-methoxy-5-phenylquinoxalin-2-yl)-1-methyl-1H-pyrazole-4-carboxamide |
| 33 | N-(8-methoxy-5-phenylquinoxalin-2-yl)cyclopropanecarboxamide |
| 34 | N-(8-methoxy-5-phenylquinoxalin-2-yl)-1-methyl-1H-pyrazole-5-carboxamide |
| 35 | N-(8-methoxy-5-phenylquinoxalin-2-yl)-1,3-thiazole-5-carboxamide |
| 36 | N-(8-methoxy-5-phenylquinoxalin-2-yl)-2-methyl-1,3-thiazole-5-carboxamide |
| 37 | N-(8-methoxy-5-phenylquinoxalin-2-yl)-4H-1,2,4-triazole-3-carboxamide |
| 38 | N-[5-(4-fluorophenyl)-8-methoxyquinoxalin-2-yl]-4-hydroxy-4-methylpiperidine-1-carboxamide |
| 39 | 4-Hydroxy-4-methyl-piperidine-1-carboxylic acid [5-methoxy-8-(tetrahydro-pyran-4-yl)-pyrido[3,4-b]pyrazin-3-yl]-amide |
| 40 | N-[8-methoxy-5-(oxan-4-yl)quinoxalin-2-yl]cyclopropanecarboxamide |
| 41 | 4-Hydroxy-4-methyl-piperidine-1-carboxylic acid [8-methoxy-5-(6-methyl-pyridazin-3-yl)-quinoxalin-2-yl]-amide |
| 42 | 1-(2-Methoxy-ethyl)-1H-pyrazole-4-carboxylic acid [8-methoxy-5-(6-methyl-pyridazin-3-yl)-quinoxalin-2-yl]-amide |
| 43 | 1-(2-Methoxy-ethyl)-1H-pyrazole-4-carboxylic acid (8-methoxy-5-pyridin-4-yl-quinoxalin-2-yl)-amide |
| 44 | 1-(2-Methoxy-ethyl)-1H-pyrazole-4-carboxylic acid [5-methoxy-8-(tetrahydro-pyran-4-yl)-pyrido[3,4-b]pyrazin-3-yl]-amide |
| 45 | Isoxazole-4-carboxylic acid (5-methoxy-8-phenyl-pyrido[3,4-b]pyrazin-3-yl)-amide |
| 46 | 4-Hydroxymethyl-4-methyl-piperidine-1-carboxylic acid [8-methoxy-5-(tetrahydro-pyran-4-yl)-quinoxalin-2-yl]-amide |
| 47 | 3-Hydroxy-3-methyl-pyrrolidine-1-carboxylic acid [5-methoxy-8-(tetrahydro-pyran-4-yl)-pyrido[3,4-b]pyrazin-3-yl]-amide |
| 48 | 4-Hydroxy-4-methyl-piperidine-1-carboxylic acid [5-(2-fluoro-phenyl)-8-methoxy-quinoxalin-2-yl]-amide |
| 49 | 4-Hydroxy-4-methyl-piperidine-1-carboxylic acid [5-(4-fluoro-phenyl)-8-methoxy-quinoxalin-2-yl]-amide |
| 50 | 4-Hydroxy-4-methyl-piperidine-1-carboxylic acid [5-(3-fluoro-phenyl)-8-methoxy-quinoxalin-2-yl]-amide |
| 51 | 4-Hydroxy-4-methyl-piperidine-1-carboxylic acid [8-methoxy-5-(2-oxa-7-aza-spiro[4.4]non-7-yl)-quinoxalin-2-yl]-amide |
| 52 | 4-Hydroxy-4-methyl-piperidine-1-carboxylic acid (8-methoxy-5-pyridin-3-yl-quinoxalin-2-yl)-amide |
| 53 | 4-Hydroxy-4-methyl-piperidine-1-carboxylic acid (5-azepan-1-yl-8-methoxy-quinoxalin-2-yl)-amide |
| 54 | 4-Hydroxy-4-methyl-piperidine-1-carboxylic acid (8-methoxy-5-phenyl-pyrido[3,4-b]pyrazin-2-yl)-amide |
| 55 | Isoxazole-4-carboxylic acid [5-methoxy-8-(tetrahydro-pyran-4-yl)-pyrido[3,4-b]pyrazin-3-yl]-amide |
| 56 | 1-Methyl-1H-pyrazole-4-carboxylic acid [8-methoxy-5-(tetrahydro-pyran-4-yl)-quinoxalin-2-yl]-amide |
| 57 | 5-Methyl-isoxazole-4-carboxylic acid [8-methoxy-5-(tetrahydro-pyran-4-yl)-quinoxalin-2-yl]-amide |
| 58 | 5-Cyclopropyl-isoxazole-4-carboxylic acid [8-methoxy-5-(tetrahydro-pyran-4-yl)-quinoxalin-2-yl]-amide |
| 59 | 1-(2-Methoxy-ethyl)-1H-[1,2,3]triazole-4-carboxylic acid [8-methoxy-5-(tetrahydro-pyran-4-yl)-quinoxalin-2-yl]-amide |
| 60 | 1-Methyl-1H-[1,2,3]triazole-4-carboxylic acid [8-methoxy-5-(tetrahydro-pyran-4-yl)-quinoxalin-2-yl]-amide |
| 61 | 1-Cyano-cyclopropanecarboxylic acid [8-methoxy-5-(tetrahydro-pyran-4-yl)-quinoxalin-2-yl]-amide |
| 62 | Cyclopropanesulfonic acid [8-methoxy-5-(tetrahydro-pyran-4-yl)-quinoxalin-2-yl]-amide |
| 63 | [8-Methoxy-5-(tetrahydro-pyran-4-yl)-quinoxalin-2-yl]-carbamic acid isopropyl ester |
| 64 | 2-Methyl-2H-pyrazole-3-carboxylic acid [8-methoxy-5-(tetrahydro-pyran-4-yl)-quinoxalin-2-yl]-amide |
| 65 | Thiazole-5-carboxylic acid [8-methoxy-5-(tetrahydro-pyran-4-yl)-quinoxalin-2-yl]-amide |
| 66 | 2-Methyl-thiazole-5-carboxylic acid [8-methoxy-5-(tetrahydro-pyran-4-yl)-quinoxalin-2-yl]-amide |
| 67 | 1H-[1,2,4]Triazole-3-carboxylic acid [8-methoxy-5-(tetrahydro-pyran-4-yl)-quinoxalin-2-yl]-amide |
| 68 | 2,3-Dimethyl-3H-imidazole-4-sulfonic acid [8-methoxy-5-(tetrahydro-pyran-4-yl)-quinoxalin-2-yl]-amide |
| 69 | Imidazo[1,2-a]pyrazine-2-carboxylic acid [8-methoxy-5-(tetrahydro-pyran-4-yl)-quinoxalin-2-yl]-amide |
| 70 | Azetidine-3-carboxylic acid [8-methoxy-5-(tetrahydro-pyran-4-yl)-quinoxalin-2-yl]-amide |
| 71 | Azetidine-3-carboxylic acid (8-methoxy-5-phenyl-quinoxalin-2-yl)-amide |
| 72 | Imidazo[1,2-a]pyrazine-2-carboxylic acid (8-methoxy-5-phenyl-quinoxalin-2-yl)-amide |
| 73 | 2,3-Dimethyl-3H-imidazole-4-sulfonic acid (8-methoxy-5-phenyl-quinoxalin-2-yl)-amide |
| 74 | (8-Methoxy-5-phenyl-quinoxalin-2-yl)-carbamic acid isopropyl ester |
| 75 | Cyclopropanesulfonic acid (8-methoxy-5-phenyl-quinoxalin-2-yl)-amide |
| 76 | 1-Cyano-cyclopropanecarboxylic acid (8-methoxy-5-phenyl-quinoxalin-2-yl)-amide |
| 77 | 1-Methyl-1H-[1,2,3]triazole-4-carboxylic acid (8-methoxy-5-phenyl-quinoxalin-2-yl)-amide |
| 78 | 1-(2-Methoxy-ethyl)-1H-[1,2,3]triazole-4-carboxylic acid (8-methoxy-5-phenyl-quinoxalin-2-yl)-amide |
| 79 | 5-Cyclopropyl-isoxazole-4-carboxylic acid (8-methoxy-5-phenyl-quinoxalin-2-yl)-amide |
| 80 | 5-Methyl-isoxazole-4-carboxylic acid (8-methoxy-5-phenyl-quinoxalin-2-yl)-amide |
| 81 | 1-Methyl-1H-pyrazole-4-carboxylic acid (8-methoxy-5-phenyl-quinoxalin-2-yl)-amide |
| 82 | 6-Oxo-1,6-dihydro-pyridazine-4-carboxylic acid (8-methoxy-5-phenyl-quinoxalin-2-yl)-amide |
| 83 | 4-Hydroxy-4-methyl-piperidine-1-carboxylic acid (5-butyl-8-methoxy-quinoxalin-2-yl)-amide |
| 84 | 4-Hydroxy-4-methyl-piperidine-1-carboxylic acid [8-methoxy-5-(1-propyl-cyclopropyl)-quinoxalin-2-yl]-amide |
| 85 | 4-Hydroxy-4-methyl-piperidine-1-carboxylic acid [8-methoxy-5-(1-methoxymethyl-cyclopropyl)-quinoxalin-2-yl]-amide |
| 86 | 4-Hydroxy-4-methyl-piperidine-1-carboxylic acid [5-(3-amino-phenyl)-8-methoxy-quinoxalin-2-yl]-amide |
| 87 | 4-Hydroxy-4-methyl-piperidine-1-carboxylic acid (8-methoxy-5-pyridin-2-yl-quinoxalin-2-yl)-amide |
| 88 | 4-Hydroxy-4-methyl-piperidine-1-carboxylic acid (8-methoxy-5-o-tolyl-quinoxalin-2-yl)-amide |
| 89 | 1-Cyano-cyclopropanecarboxylic acid (5-methoxy-8-phenyl-pyrido[3,4-b]pyrazin-3-yl)-amide |
| 90 | Cyclopropanecarboxylic acid (5-methoxy-8-phenyl-pyrido[3,4-b]pyrazin-3-yl)-amide |
| 91 | N-[8-methoxy-5-(oxan-4-yl)quinoxalin-2-yl]-2-oxa-7-azaspiro[4.4]nonane-7-carboxamide |
| 92 | 4-hydroxy-N-[8-methoxy-5-(pyridin-4-yl)quinoxalin-2-yl]-4-methylpiperidine-1-carboxamide |
| 93 | 3-hydroxy-N-[8-methoxy-5-(oxan-4-yl)quinoxalin-2-yl]-3-methylpyrrolidine-1-carboxamide |
| 94 | N-[8-methoxy-5-(oxan-4-yl)quinoxalin-2-yl]-2-methyl-1,3-oxazole-4-carboxamide |
| 95 | 4-(hydroxymethyl)-N-[8-methoxy-5-(oxan-4-yl)quinoxalin-2-yl]-4-methylpiperidine-1-carboxamide |
| 96 | N-[8-methoxy-5-(oxan-4-yl)quinoxalin-2-yl]-2,2-dioxo-2lambda6-thia-6-azaspiro[3.3]heptane-6-carboxamide |
| 97 | 6-methoxy-N-[8-methoxy-5-(oxan-4-yl)quinoxalin-2-yl]pyridazine-3-carboxamide |
| 98 | N-[8-methoxy-5-(oxan-4-yl)quinoxalin-2-yl]-1-(2-methoxyethyl)-1H-pyrazole-4-carboxamide |
| 99 | 4-hydroxy-N-(8-methoxy-5-phenylquinoxalin-2-yl)-4-(prop-2-yn-1-yl)piperidine-1-carboxamide |
| 100 | 3-hydroxy-N-(8-methoxy-5-phenylquinoxalin-2-yl)-3-methylpyrrolidine-1-carboxamide |
| 101 | 4-(hydroxymethyl)-N-(8-methoxy-5-phenylquinoxalin-2-yl)-4-methylpiperidine-1-carboxamide |
| 102 | N-(8-methoxy-5-phenylquinoxalin-2-yl)-8-oxa-2-azaspiro[4.5]decane-2-carboxamide |
| 103 | 4-Hydroxy-4-prop-2-ynyl-piperidine-1-carboxylic acid [5-methoxy-8-(tetrahydro-pyran-4-yl)-pyrido[3,4-b]pyrazin-3-yl]-amide |
| 104 | 4-Hydroxymethyl-4-methyl-piperidine-1-carboxylic acid [5-methoxy-8-(tetrahydro-pyran-4-yl)-pyrido[3,4-b]pyrazin-3-yl]-amide |
| 105 | N-(8-methoxy-5-phenylquinoxalin-2-yl)-2-methyl-1,3-oxazole-5-carboxamide |
| 106 | Cyclopropanecarboxylic acid [5-methoxy-8-(tetrahydro-pyran-4-yl)-pyrido[3,4-b]pyrazin-3-yl]-amide |
| 107 | N-(8-butyl-5-methoxyquinoxalin-2-yl)-4-hydroxy-4-methylpiperidine-1-carboxamide |
| 108 | N-(5-butyl-8-methoxyquinoxalin-2-yl)-4-hydroxy-4-methylpiperidine-1-carboxamide |

| No. | IUPAC-Name |
|---|---|
| 109 | N-[5-(3,6-dihydro-2H-pyran-4-yl)-8-methoxyquinoxalin-2-yl]-4-hydroxy-4-methylpiperidine-1-carboxamide |
| 110 | N-[8-(3-fluorophenyl)-5-methoxyquinoxalin-2-yl]-4-hydroxy-4-methylpiperidine-1-carboxamide |
| 111 | N-[8-(2-fluorophenyl)-5-methoxyquinoxalin-2-yl]-4-hydroxy-4-methylpiperidine-1-carboxamide |
| 112 | 4-hydroxy-N-[5-methoxy-8-(pyridin-3-yl)quinoxalin-2-yl]-4-methylpiperidine-1-carboxamide |
| 113 | 6-methoxy-N-(8-methoxy-5-phenylquinoxalin-2-yl)pyridazine-3-carboxamide |
| 114 | 4-hydroxy-N-(8-methoxy-5-{1-[(pyridin-2-yl)methyl]-1H-pyrazol-4-yl}quinoxalin-2-yl)-4-methylpiperidine-1-carboxamide |
| 115 | 4-{2-[(4-hydroxy-4-methylpiperidine-1-carbonyl)amino]-8-methoxyquinoxalin-5-yl}-N-methylpyridine-2-carboxamide |
| 116 | tert-butyl 3-(4-{2-[(4-hydroxy-4-methylpiperidine-1-carbonyl)amino]-8-methoxyquinoxalin-5-yl}-1H-pyrazol-1-yl)azetidine-1-carboxylate |
| 117 | 4-hydroxy-N-{8-methoxy-5-[3-(2-methoxyethoxy)phenyl]quinoxalin-2-yl}-4-methylpiperidine-1-carboxamide |
| 118 | 4-hydroxy-N-(8-methoxy-5-{3-[(2-methoxyethoxy)methyl]phenyl}quinoxalin-2-yl)-4-methylpiperidine-1-carboxamide |
| 119 | 4-hydroxy-N-(8-methoxy-5-{1-[2-(2-methoxyethoxy)ethyl]-1H-pyrazol-4-yl}quinoxalin-2-yl)-4-methylpiperidine-1-carboxamide |
| 120 | N-[5-(2-fluorophenyl)-8-methoxyquinoxalin-2-yl]cyclopropanecarboxamide |
| 121 | N-[8-methoxy-5-(pyridin-3-yl)quinoxalin-2-yl]cyclopropanecarboxamide |
| 122 | N-[5-(azepan-1-yl)-8-methoxyquinoxalin-2-yl]cyclopropanecarboxamide |
| 123 | N-[5-(2,3-difluorophenyl)-8-methoxyquinoxalin-2-yl]cyclopropanecarboxamide |
| 124 | N-[5-(2,5-difluorophenyl)-8-methoxyquinoxalin-2-yl]cyclopropanecarboxamide |
| 125 | N-[5-(2,3-difluorophenyl)-8-methoxyquinoxalin-2-yl]-2-methyl-1,3-oxazole-5-carboxamide |
| 126 | N-[5-(4-fluorophenyl)-8-methoxyquinoxalin-2-yl]cyclopropanecarboxamide |
| 127 | N-[8-methoxy-5-(1,2,3,6-tetrahydropyridin-4-yl)quinoxalin-2-yl]cyclopropanecarboxamide |
| 128 | N-[5-(2,5-difluorophenyl)-8-methoxyquinoxalin-2-yl]-2-methyl-1,3-oxazole-5-carboxamide |
| 129 | N-[5-(2-fluorophenyl)-8-methoxyquinoxalin-2-yl]-2-methyl-1,3-oxazole-5-carboxamide |
| 130 | N-[8-methoxy-5-(oxan-4-yl)quinoxalin-2-yl]-2-methyl-1,3-oxazole-5-carboxamide |
| 131 | N-[5-(4-fluorophenyl)-8-methoxyquinoxalin-2-yl]-2-methyl-1,3-oxazole-5-carboxamide |
| 132 | N-[5-(3,6-dihydro-2H-pyran-4-yl)-8-methoxyquinoxalin-2-yl]-2-methyl-1,3-oxazole-5-carboxamide |
| 133 | N-{5-[1-(azetidin-3-yl)-1H-pyrazol-4-yl]-8-methoxyquinoxalin-2-yl}-4-hydroxy-4-methylpiperidine-1-carboxamide |
| 134 | N-[5-(3,6-dihydro-2H-pyran-4-yl)-8-methoxyquinoxalin-2-yl]-2-methyl-1,3-thiazole-5-carboxamide |
| 135 | N-[5-(3,6-dihydro-2H-pyran-4-yl)-8-methoxyquinoxalin-2-yl]-1-methyl-1H-pyrazole-4-carboxamide |
| 136 | N-[5-(3,6-dihydro-2H-pyran-4-yl)-8-methoxyquinoxalin-2-yl]-1,2-thiazole-4-carboxamide |
| 137 | 1-amino-N-[5-(3,6-dihydro-2H-pyran-4-yl)-8-methoxyquinoxalin-2-yl]cyclopropane-1-carboxamide |
| 138 | N-[8-methoxy-5-(pyridin-3-yl)quinoxalin-2-yl]-2-methyl-1,3-oxazole-5-carboxamide |
| 139 | 2-amino-N-[5-(3,6-dihydro-2H-pyran-4-yl)-8-methoxyquinoxalin-2-yl]-1,3-thiazole-4-carboxamide |
| 140 | N-[5-(3,6-dihydro-2H-pyran-4-yl)-8-methoxyquinoxalin-2-yl]-5-(oxolan-3-yl)-1,3-thiazole-2-carboxamide |
| 141 | N-[5-(2,5-dihydrofuran-3-yl)-8-methoxyquinoxalin-2-yl]cyclopropanecarboxamide |
| 142 | 5-(aminomethyl)-N-[5-(3,6-dihydro-2H-pyran-4-yl)-8-methoxyquinoxalin-2-yl]furan-3-carboxamide |
| 143 | ethyl 5-({[5-(3,6-dihydro-2H-pyran-4-yl)-8-methoxyquinoxalin-2-yl]carbamoyl}amino)-1,3,4-thiadiazole-2-carboxylate |
| 144 | N'1-[5-(3,6-dihydro-2H-pyran-4-yl)-8-methoxyquinoxalin-2-yl]-N1,N1-dimethylcyclopropane-1,1-dicarboxamide |
| 145 | N-[5-(3,6-dihydro-2H-pyran-4-yl)-8-methoxyquinoxalin-2-yl]-1-[(dimethylamino)methyl]cyclopropane-1-carboxamide |
| 146 | N-[5-(3,6-dihydro-2H-pyran-4-yl)-8-methoxyquinoxalin-2-yl]-5-methyl-1,3,4-thiadiazole-2-carboxamide |
| 147 | N-{8-methoxy-5-[3-(2-methoxyethoxy)phenyl]quinoxalin-2-yl}cyclopropanecarboxamide |
| 148 | N-{8-methoxy-5-[3-(2-methoxyethoxy)phenyl]quinoxalin-2-yl}-2-methyl-1,3-oxazole-5-carboxamide |
| 149 | N'1-(8-methoxy-5-phenylquinoxalin-2-yl)-N1,N1-dimethylcyclopropane-1,1-dicarboxamide |
| 150 | 1-[(dimethylamino)methyl]-N-(8-methoxy-5-phenylquinoxalin-2-yl)cyclopropane-1-carboxamide |
| 151 | N-{8-methoxy-5-[3-(2-methoxyethoxy)phenyl]quinoxalin-2-yl}-2-methyl-1,3-thiazole-5-carboxamide |
| 152 | N-{8-methoxy-5-[3-(2-methoxyethoxy)phenyl]quinoxalin-2-yl}-5-methyl-1,3,4-thiadiazole-2-carboxamide |
| 153 | 4-hydroxy-N-{8-methoxy-5-[1-(pyridin-2-yl)-1H-pyrazol-4-yl]quinoxalin-2-yl}-4-methylpiperidine-1-carboxamide |
| 154 | N-[8-methoxy-5-(6-methylpyridazin-3-yl)quinoxalin-2-yl]-2-methyl-1,3-oxazole-5-carboxamide |
| 155 | N-[8-methoxy-5-(2-methoxypyrimidin-5-yl)quinoxalin-2-yl]-2-methyl-1,3-oxazole-5-carboxamide |
| 156 | N-[8-methoxy-5-(2-methoxypyrimidin-5-yl)quinoxalin-2-yl]cyclopropanecarboxamide |
| 157 | N-{5-[1-(difluoromethyl)-1H-pyrazol-4-yl]-8-methoxyquinoxalin-2-yl}-2-methyl-1,3-oxazole-5-carboxamide |
| 158 | N-{5-[1-(difluoromethyl)-1H-pyrazol-4-yl]-8-methoxyquinoxalin-2-yl}-4-hydroxy-4-methylpiperidine-1-carboxamide |
| 159 | N-[5-(3,6-dihydro-2H-pyran-4-yl)-8-methoxyquinoxalin-2-yl]-1H-imidazole-5-carboxamide |
| 160 | N-(8-methoxy-5-phenylquinoxalin-2-yl)-1H-imidazole-5-carboxamide |
| 161 | N-[8-methoxy-5-(1,4-oxazepan-4-yl)quinoxalin-2-yl]cyclopropanecarboxamide | or a physiologically acceptable salt, derivative, solvate, prodrug or stereoisomer thereof.

8. A process for the preparation of a compound of the formula I according to claim 1, comprising

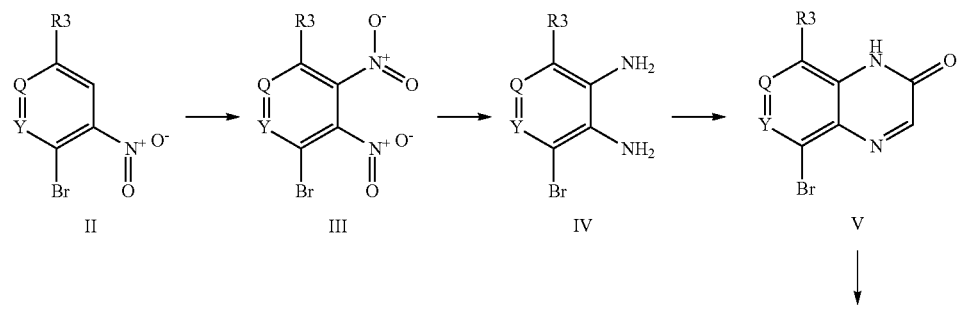

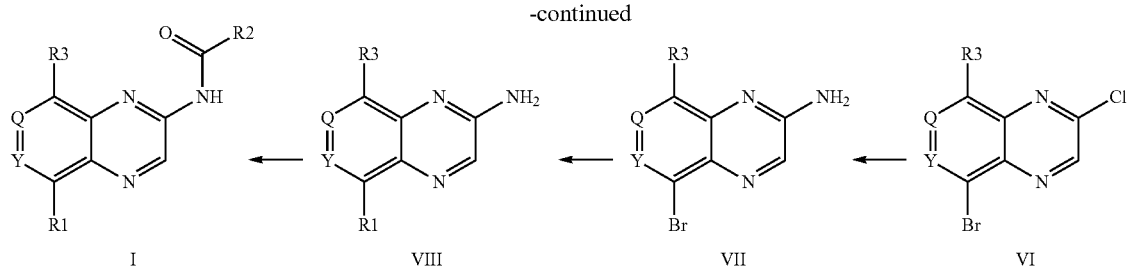

a) a compound of the formula II undergoes a nitration reaction, followed by a reduction to give a compound of formula IV, a compound of formula IV is cyclized to give a compound of formula V, a compound of formula V is chlorinated followed by a copper catalyzed amination reaction to give compound VII, a compound of formula VII is reacted in a Suzuki type reaction to a compound of formula VIII by a catalyst and base, a compound of formula VIII is converted to a compound of formula I by amidation or carbamide formation conditions wherein Q, Y, $R^1$, $R^2$ and $R^3$ have the meanings as disclosed for the compound of formula I,

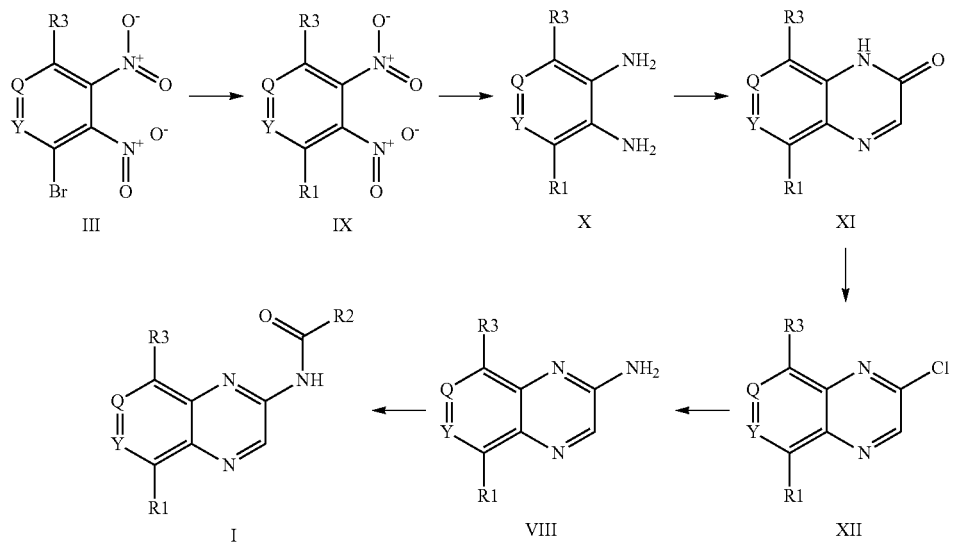

b) a compound of the formula III is reacted with a boronic ester or acid under Suzuki-type reaction conditions to give a compound of formula IX or reacted with an amine in a nucleophilic substitution reaction under increased temperature to form a compound of formula IX, a compound of formula IX is reduced to a compound of formula X and cyclized to a compound of formula XI, a compound of formula XI is chlorinated followed by copper catalyzed amination to give compound VIII and finally compound VIII is reacted to a compound of formula I under amidation or carbamide formation conditions and wherein Q, Y, $R^1$, $R^2$ and $R^3$ have the meanings as disclosed for the compound of formula I,

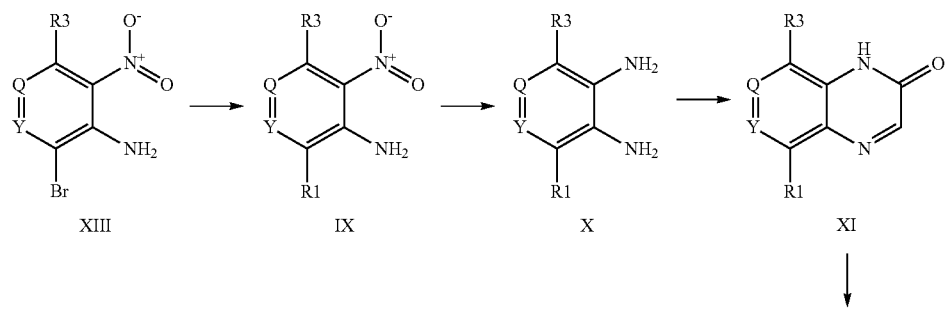

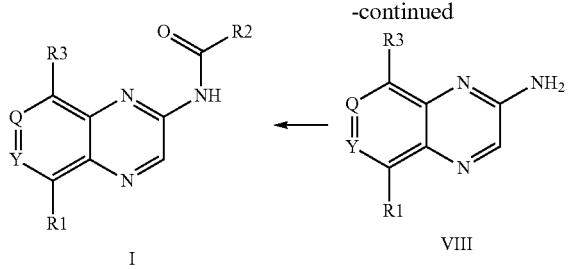

I

-continued

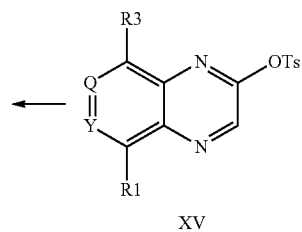

VIII

XV c) a compound of the formula XIII is reacted with a boronic ester or acid under Suzuki-type reaction conditions to give a compound of formula XIV, a compound of formula XIV is reduced to a compound of formula X and cyclized to a compound of formula XI, a compound of formula XI is tosylated followed by metal catalyzed amination to give compound VIII and finally compound VIII is reacted to a compound of formula I under amidation or carbamide formation conditions and wherein Q, Y, $R^1$, $R^2$ and $R^3$ have the meanings as disclosed for the compound of formula I, d) a base of a compound of formula I is converted into one of its salts by treatment with an acid, or e) an acid of a compound of formula I is converted into one of its salts by treatment with a base.

9. A method for inhibiting an adenosine $A_{2A}$ and/or $A_{2B}$ receptor, comprising administering to said receptor a compound of claim 1 or a physiologically acceptable salt, derivative, solvate, prodrug or stereoisomer thereof.

10. A pharmaceutical composition comprising at least one compound according to claim 1 and/or a physiologically acceptable salt, derivative, solvate, prodrug or stereoisomer thereof and at least one excipient and/or adjuvant.

11. The pharmaceutical composition according to claim 10, further comprising at least one further pharmaceutically active compound.

12. A process for the preparation of a pharmaceutical composition according to claim 10, comprising bringing a compound of formula I and/or one of its physiologically acceptable salts, derivatives, solvates, prodrugs or stereoisomers thereof into a dosage form together with a solid, liquid or semi-liquid excipient or adjuvant.

13. A method for the treatment and/or prophylaxis of a physiological and/or pathophysiological state, comprising administering to a subject in need thereof an effective amount of a pharmaceutical composition according to claim 10, wherein an adenosine $A_{2A}$ and/or $A_{2B}$ receptor is inhibited.

14. A method for the treatment and/or prophylaxis of a hyperproliferative or infectious disease or disorder, comprising administering to a subject in need thereof an effective amount of a pharmaceutical composition according to claim 10, wherein an adenosine $A_{2A}$ and/or $A_{2B}$ receptor is inhibited.

15. The method according to claim 14, wherein the hyperproliferative disease or disorder is cancer.

16. The method according to claim 15, wherein the cancer is selected from the group consisting of acute lymphocytic leukemia, chronic lymphocytic leukemia, acute granulocytic leukemia, adrenal cortex cancer, bladder cancer, brain cancer, breast cancer, cervical cancer, cervical hyperplasia, cervical cancer, chorio cancer, chronic granulocytic leukemia, chronic lymphocytic leukemia, colon cancer, endometrial cancer, esophageal cancer, essential thrombocytosis, genitourinary carcinoma, glioma, glioblastoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid leukemia, lymphocytic leukemia, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell cancer, rhabdomyosarcoma, skin cancer, small-cell lung cancer, soft-tissue sarcoma, squamous cell cancer, stomach cancer, testicular cancer, thyroid cancer and Wilms' tumor.

17. The method according to claim 14, wherein the hyperproliferative disease or disorder is selected from the group consisting of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ transplantation, immune hyperproliferation associated with tissue transplantation, an immunoproliferative disease, an immunoproliferative disorder, inflammatory bowel disease, psoriasis, rheumatoid arthritis, systemic lupus erythematosus, vascular hyperproliferation secondary to retinal hypoxia and vasculitis.

18. The method according to claim 14, wherein the infectious disease or disorder is selected from the group consisting of a) virally induced infectious diseases which are caused by retroviruses, hepadnaviruses, herpesviruses, flaviviridae and/or adenoviruses wherein the retroviruses are selected from the group consisting of lentiviruses and oncoretroviruses, wherein the lentivirus is selected from the group consisting of HIV-1, HIV-2, FIV, BIV, SIVs, SHIV, CAEV, VMV and EIAV and the oncoretrovirus is selected from the group consisting of HTLV-I, HTLV-II and BLV, the hepadnavirus is selected from the group consisting of HBV, GSHV and WHV, the herpesvirus is selected from the group consisting of HSV I, HSV II, EBV, VZV, HCMV and HHV 8 and the flaviviridae is selected from the group consisting of HCV, West nile and Yellow Fever, b) bacterial infectious diseases which are caused by Gram-positive bacteria wherein the Gram-positive bacteria are selected from the group consisting of methicillin-susceptible staphylococci, methicillin-resistant staphylococci, *Staphylococcus aureus, Staphylococcus epidermidis, Staphylococcus haemolyticus, Staphylococcus hominis, Staphylococcus saprophyticus*, coagulase-negative staphylococci, glycopeptides-intermediate susceptible *Staphylococcus aureus*, penicillin-susceptible streptococci, penicillin-resistant streptococci, *Streptococcus pneumoniae, Streptococcus pyogenes, Streptococcus agalactiae, Streptococcus avium, Streptococcus bovis, Streptococcus lactis, Streptococcus sanguis*, Streptococci Group C, Streptococci Group G, viridans streptococci, enterococci, vancomycin susceptible strains, vancomycin-resistant strains, *Enterococcus faecalis, Enterococcus faecium, Clostridium difficile, Listeria monocytogenes, Corynebacterium jeikeium, Chlamydia* spp, *C. pneumoniae* and *Mycobacterium tuberculosis*, c) bacterial infectious diseases which are caused by Gram-negative bacteria wherein the Gram-negative bacteria are selected from the group consisting of the Genus Enterobacteriacae, *Escherichia* spp., *Escherichia coli, Klebsiella* spp., *Enterobacter* spp., *Citrobacter* spp., *Serratia* spp., *Proteus* spp., *Providencia* spp., *Salmonella* spp., *Shigella* spp., the genus *Pseudomonas, P. aeruginosa, Moraxella* spp., *M. catarrhalis, Haemophilus* spp. and *Neisseria* spp., d) infectious diseases induced by intracellular active parasites selected from the group consisting of phylum Apicomplexa, Sarcomastigophora, *Trypanosoma, Plasmodia, Leishmania, Babesia, Theileria*, Cryptosporidia, Sacrocystida, Amoebia, Coccidia and Trichomonadia.

19. A kit comprising separate packs of
  a) a compound according to claim 1 or a physiologically acceptable salt, derivative, solvate, prodrug or stereoisomer thereof, and
  b) a further pharmaceutically active compound.

20. The compound according to claim 1 or a pharmaceutically acceptable salt thereof.

21. The compound according to claim 7 or a pharmaceutically acceptable salt thereof.

* * * * *